United States Patent
Bern et al.

(10) Patent No.: US 12,400,846 B2
(45) Date of Patent: Aug. 26, 2025

(54) INTERACTIVE ANALYSIS OF MASS SPECTROMETRY DATA INCLUDING PEAK SELECTION AND DYNAMIC LABELING

(71) Applicant: Protein Metrics, LLC, Cupertino, CA (US)

(72) Inventors: Marshall Bern, San Carlos, CA (US); Yong Joo Kil, Fremont, CA (US)

(73) Assignee: Protein Metrics, LLC, Boston, MA (US)

( * ) Notice: Subject to any disclaimer, the term of this patent is extended or adjusted under 35 U.S.C. 154(b) by 229 days.

(21) Appl. No.: 18/298,327

(22) Filed: Apr. 10, 2023

(65) Prior Publication Data

US 2023/0343569 A1 Oct. 26, 2023

Related U.S. Application Data

(63) Continuation-in-part of application No. 17/240,996, filed on Apr. 26, 2021, now Pat. No. 11,626,274,
(Continued)

(51) Int. Cl.
*H01J 49/00* (2006.01)
*G01N 33/58* (2006.01)
*G01N 33/68* (2006.01)

(52) U.S. Cl.
CPC .......... *H01J 49/0036* (2013.01); *G01N 33/58* (2013.01); *G01N 33/6848* (2013.01)

(58) Field of Classification Search
CPC ........ H01J 49/00; H01J 49/02; H01J 49/0027; H01J 49/0036; H01J 49/26; G01J 3/00; G01J 3/02; G01J 3/12; G01J 3/28; G01J 3/2823; G01J 3/283; G01J 3/2836; G01J 3/284
(Continued)

(56) References Cited

U.S. PATENT DOCUMENTS 4,464,650 A 8/1984 Eastman et al.
4,558,302 A 12/1985 Welch
(Continued)

FOREIGN PATENT DOCUMENTS

GB 2401721 A 11/2004
JP 2004317509 A 11/2004
(Continued)

OTHER PUBLICATIONS

ZNova Decorivolutiori; retrieved from the internet (https://web.archive.org/web/20141106214830/http://www.enovatia.com:80/downloads/manuals/promass/Help/html/prom2cdq.htm); 1 page; on Oct. 6, 2023.
(Continued)

*Primary Examiner* — Jason L McCormack
(74) *Attorney, Agent, or Firm* — Shay Glenn LLP

(57) ABSTRACT

This invention relates to graphical user-interactive displays for use in MS-based analysis of protein impurities, as well as methods and software for generating and using such. One aspect provides a user-interactive display comprising interactive and dynamic selection of one or more masses and concurrent display of peaks (points) corresponding to that predicted mass value across other displays (MS1, deconvolved mass spectrum, mass extracted ion chromatogram, etc.).

20 Claims, 37 Drawing Sheets

Related U.S. Application Data which is a continuation-in-part of application No. 16/773,857, filed on Jan. 27, 2020, now Pat. No. 10,991,558, which is a continuation of application No. 16/052,506, filed on Aug. 1, 2018, now Pat. No. 10,546,736.

(60) Provisional application No. 62/540,031, filed on Aug. 1, 2017.

(58) Field of Classification Search
USPC .................................................. 250/281, 282
See application file for complete search history.

(56) References Cited

U.S. PATENT DOCUMENTS

| | | | |
|---|---|---|---|
| 4,814,764 | A | 3/1989 | Middleton |
| 5,343,554 | A | 8/1994 | Koza et al. |
| 5,910,655 | A | 6/1999 | Skilling |
| 5,995,989 | A | 11/1999 | Gedcke et al. |
| 6,094,627 | A | 7/2000 | Peck et al. |
| 6,393,393 | B1 | 5/2002 | Kawahara |
| 6,535,555 | B1 | 3/2003 | Bordes et al. |
| 6,798,360 | B1 | 9/2004 | Qian et al. |
| 6,906,320 | B2 | 6/2005 | Sachs et al. |
| 7,006,567 | B2 | 2/2006 | Frossard et al. |
| 7,283,684 | B1 | 10/2007 | Keenan |
| 7,283,937 | B2 | 10/2007 | Goldberg |
| 7,297,940 | B2 | 11/2007 | Bem |
| 7,397,961 | B2 | 7/2008 | Keeney et al. |
| 7,400,772 | B1 | 7/2008 | Keenan |
| 7,402,438 | B2 | 7/2008 | Goldberg |
| 7,429,727 | B2 | 9/2008 | Bern |
| 7,496,453 | B2 | 2/2009 | Chau |
| 7,680,670 | B2 | 3/2010 | Lamblin et al. |
| 7,979,258 | B2 | 7/2011 | Goldberg et al. |
| 8,004,432 | B2 | 8/2011 | Kawato |
| 8,023,750 | B2 | 9/2011 | Raveendran et al. |
| 8,077,988 | B2 | 12/2011 | Donoho |
| 8,108,153 | B2 | 1/2012 | Bern |
| 8,428,889 | B2 | 4/2013 | Wright |
| 8,511,140 | B2 | 8/2013 | Gorenstein et al. |
| 8,598,516 | B2 | 12/2013 | Sapargaliyev et al. |
| 8,645,145 | B2 | 2/2014 | Subbaraman et al. |
| 9,385,751 | B2 | 7/2016 | Kletter |
| 9,571,122 | B2 | 2/2017 | Kletter |
| 9,640,376 | B1 | 5/2017 | Becker et al. |
| 9,859,917 | B2 | 1/2018 | Kletter |
| 10,199,206 | B2 | 2/2019 | Becker et al. |
| 10,354,421 | B2 | 7/2019 | Becker et al. |
| 10,510,521 | B2 | 12/2019 | Kil et al. |
| 10,546,736 | B2 | 1/2020 | Bern et al. |
| 10,665,439 | B2 | 5/2020 | Bern |
| 10,879,057 | B2 | 12/2020 | Kil et al. |
| 10,991,558 | B2 | 4/2021 | Bern et al. |
| 11,127,575 | B2 | 9/2021 | Bern |
| 11,276,204 | B1 | 3/2022 | Kletter |
| 11,289,317 | B2 | 3/2022 | Kil et al. |
| 11,346,844 | B2 | 5/2022 | Nichols et al. |
| 11,626,274 | B2 | 4/2023 | Bern et al. |
| 11,640,901 | B2 | 5/2023 | Bern |
| 2002/0068366 | A1 | 6/2002 | LaDine et al. |
| 2003/0031369 | A1 | 2/2003 | Le Pennec et al. |
| 2003/0200032 | A1* | 10/2003 | Keating .......... G16B 40/10 702/19 |
| 2003/0218634 | A1 | 11/2003 | Kuchinsky et al. |
| 2004/0083063 | A1 | 4/2004 | McClure |
| 2004/0102906 | A1 | 5/2004 | Roder |
| 2004/0160353 | A1 | 8/2004 | Cirillo et al. |
| 2005/0047670 | A1 | 3/2005 | Qian et al. |
| 2005/0063864 | A1* | 3/2005 | Sano .............. H01J 49/0031 422/68.1 |
| 2005/0276326 | A1 | 12/2005 | Drezner |
| 2008/0010309 | A1 | 1/2008 | Sugita |
| 2008/0025394 | A1 | 1/2008 | Francois et al. |
| 2008/0260269 | A1 | 10/2008 | Thiagarajan |
| 2009/0012931 | A1 | 1/2009 | Appa et al. |
| 2009/0052528 | A1 | 2/2009 | Jeon et al. |
| 2009/0179147 | A1 | 7/2009 | Milgram et al. |
| 2010/0124785 | A1 | 5/2010 | Bern |
| 2010/0288917 | A1 | 11/2010 | Satulovsky et al. |
| 2010/0288918 | A1 | 11/2010 | Satulovsky |
| 2011/0093205 | A1 | 4/2011 | Bern |
| 2011/0206119 | A1 | 8/2011 | Bivolarsky et al. |
| 2012/0047098 | A1 | 2/2012 | Reem |
| 2012/0245857 | A1 | 9/2012 | Lee et al. |
| 2013/0080073 | A1 | 3/2013 | de Corral |
| 2013/0144540 | A1 | 6/2013 | Bern et al. |
| 2013/0226594 | A1 | 8/2013 | Fuchs et al. |
| 2013/0262809 | A1 | 10/2013 | Wegener |
| 2013/0266067 | A1 | 10/2013 | Song et al. |
| 2013/0275399 | A1 | 10/2013 | Amit et al. |
| 2013/0289892 | A1 | 10/2013 | Satoh |
| 2014/0045273 | A1 | 2/2014 | Cerda et al. |
| 2014/0164444 | A1 | 6/2014 | Bowen et al. |
| 2015/0319268 | A1 | 11/2015 | Callard et al. |
| 2015/0369782 | A1 | 12/2015 | Kageyama |
| 2016/0077926 | A1 | 3/2016 | Mutalik et al. |
| 2016/0180555 | A1 | 6/2016 | Matsuo |
| 2016/0215028 | A1 | 7/2016 | Mutharia et al. |
| 2016/0268112 | A1 | 9/2016 | Yip et al. |
| 2018/0301326 | A1 | 10/2018 | Bern et al. |
| 2020/0413066 | A1 | 12/2020 | Lavaud |
| 2022/0076936 | A1 | 3/2022 | Bern |
| 2022/0207778 | A1 | 6/2022 | Kletter |
| 2022/0291229 | A1 | 9/2022 | Nichols et al. |
| 2022/0301840 | A1 | 9/2022 | Kil et al. |
| 2023/0268168 | A1 | 8/2023 | Bern et al. |
| 2024/0329052 | A1 | 10/2024 | Nichols et al. |

FOREIGN PATENT DOCUMENTS

| | | | |
|---|---|---|---|
| WO | WO2011/127544 | A1 | 10/2011 |
| WO | WO2015/031820 | A1 | 3/2015 |
| WO | WO2015/148941 | A1 | 10/2015 |
| WO | WO2015/189255 | A1 | 12/2015 |

OTHER PUBLICATIONS

Kletter et al.; U.S. Appl. No. 18/460,028 entitled "Data Compression for multidimensional time series data," filed Sep. 1, 2023.

Bern et al.; Parsimonious charge deconvolution for native mass spectrometry. Journal of proteome research; 17(3); pp. 1216-1226; Jan. 29, 2018.

Kim et al.; Comparative analysis of mass spectral similarity measures on peak alignment for comprehensive two-dimensional gas chromatography mass spectrometry; Computational and mathematical methods in medicine; 2013(1); 509761; 12 pages; doi.org/10.1155/2013/509761; Sep. 16, 2013.

Wikipedia; Intra-Frame Coding; Sep. 19, 2019; 2 pages; retrieved from the internet (https://en.wikipedia.org/w/index.php?title=Intra-frame_coding&oldid=916815985) on Aug. 20, 2024.

Zhao et al., An efficient macroblock-based diverse and flexible prediction modes selection for hyperspectral images coding; Signal Processing: Image Communication; 25(9); pp. 697-708; Oct. 1, 2010.

Jeong et al.; Flashdeconv:ultrafast, high-quality feature deconvolution for top-down proteomics; Cell Systems; 10(2); pp. 213-218; doi.org/10,1016/j.cels.2020.01.003; 13 pages; Feb. 2020.

Khelifati et al.; Corad: Correlation-aware compression of massive time series using sparse dictionary coding. In2019 IEEE International Conference on Big Data (Big Data); IEEE; pp. 2289-2298; Dec. 9, 2019.

Klammer et al.; Peptide charge state determination for low-resolution tandem mass spectra; In2005 IEEE Computational Systems Bioinformatics Conference (CSB'05); pp. 175-185; Aug. 8, 2005.

Krokhin et al.; An improved model for prediction of retention times of tryptics peptides in ion pair reversed-phase HPLC: its application

(56) References Cited

OTHER PUBLICATIONS to protein peptide mapping by off-line HPLC-MALDI MS; Molecular and Cellular Proteomics; 3(9); pp. 908-919; Sep. 2004.
Lu et al.; Improved peak detection and deconvolution of native electrospray mass spectra from large protein complexes; Journal of the American Society for Mass Spectrometry; 26(12); pp. 2141-2151; Dec. 2015.
Marty et al.; Bayesian deconvolution of mass and ion mobility spectra: from binary interactions to polydisperse ensembles; Analutical Chemistry; 87(8); pp. 4370-4376; 7 pages; (Author Manuscript); Apr. 2015.
Marty; What can unidec do for you? Mar. 24, 2015 I 28 pages; retrieved from the internet (http://unidec.chem.ox.ac.uk/UniDecTutorial.pdf) on Oct. 25, 2022.
Schreiber et al.; Using PeakView(TM) software with the XIC manager for screening and identification with high confidence based on high resolution and accurate mass LC-MS/MS; AB Sciex; Food & Environmental; (Pub. # 2170811-03); 5 pgs.; Apr. 2, 2011.
Shi et al.; Feature-based image set compression; 2013 IEEE International Conference on Multimedia and Expo (ICME); IEEE; pp. 1-6; Jul. 15, 2013.
Shi et al.; Multi-model prediction for image set compression; 2013 Visual Communications and Image Processing (VCIP); IEEE; pp. 1-6; Nov. 17, 2013.
Thermo Fisher Scientific, Inc.; Thermo Xcaliber: Qualitative Analysis (User Guide); Revision B; 290 pgs.; Sep. 2010.
Valot et al.; MassChroQ: A versatile tool for mass spectrometry quantification; Proteomics; 11(17); 23 pgs.; Sep. 2011.
VanBramer; An Introduction to Mass Spectrometry; Wider University; 38 pgs.; © 1997; (revised) Sep. 2, 1998.
Waters Corporation; Biopharmalynx: A new bioinformatics tool for automated LC/MS peptide mapping assignment: 6 pages retrived May 17, 2018 from the internet (http://www.waters.com/webassets/cms/library/docs/720002754en.pdf); Sep. 2008.
Waters Corporation; MassLynx 4.1 Getting started guide; 71500113203/RevisionA; 96 pages; retrieved May 17, 2018 from the internet (http://turroserver.chem.columbia.edu/group/instrument/HPLC/HPLC%20Getting%20Started.pdf) ; 2005.
Waters Corporation; QuanLynx User's Guide; Version 4.0; 125 pages; retrived May 17, 2018 from the internet ( http://www.waters.com/webassets/cms/support/docs/quanlynx_40.pdf); Feb. 15, 2002.
Wehofsky et al.; Isotopic deconvolution of matrix-assisted laser desorption/ionization mass spectra for substance-class specific analysis of complex samples; European Journal of Mass Spectrometry; 7(1); pp. 39-46; Feb. 1, 2001.
Xu et al.; Deconvolution in mass spectrometry based proteomics; Rapid Communications in Mass Spectrometry; 32(10); pp. 763-774; May 30, 2018.
Yang et al.; Detecting low level sequence variants in recombinant monoclonal antibodies; mAbs 2 (3); pp. 285-298; May/Jun. 2010.
Yang et al.; Hybrid mass spectrometry approaches in glycoprotein analysis and their usage in scoring biosimilarity; Nature Communications; 7(1); pp. 1-10; Nov. 8, 2016.
Ziv et al.; A universal algorithm for sequential data compression; IEEE Trans. on Information Theory; IT-23(3); pp. 337-343; May 1977.
Ziv et al.; Compression of individual sequences via variable-rate coding; IEEE Trans. on Information Theory; IT-24(5); pp. 530-536; Sep. 1978.

\* cited by examiner

Peptides

| Sequence | Mod. Type | XIC Ratio% | Score | z | Obs.m/z |
|---|---|---|---|---|---|
| K.SYSCQiTHEGSTVEK.T | Val->Ile (V) [14... | 0.01 | 375.36 | 2 | 863.8821 |
| K.SYSCQiTHEGSTVEK.T | Val->Ile (V) [14... | 0.01 | 375.36 | 2 | 863.8821 |
| K.SYSCQiTHEGSTVEK.T | Val->Ile (V) [14... | 0.01 | 434.73 | 2 | 863.8843 |
| K.SYSCQiTHEGSTVEK.T | Val->Ile (V) [14... | 0.01 | 338.11 | 2 | 863.8815 |
| K.LTVLdQPK.A | Gly->Asp (G) [... | 0.02 | 415.82 | 2 | 457.2707 |
| K.LTVLdQPK.A | Gly->Asp (G) [... | 0.02 | 378.52 | 2 | 457.2703 |
| K.LTVLdQPK.A | Gly->Asp (G) [... | 0.02 | 381.80 | 2 | 457.2705 |
| K.LTVLdQPK.A | Gly->Asp (G) [... | 0.02 | 415.82 | 2 | 457.2707 |
| K.LTVLdQPK.A | Gly->Asp (G) [... | 0.02 | 341.16 | 2 | 457.2711 |
| K.sSLYLQMNSLR.A | Asn->Ser (N) [... | 2.89 | 36.32 | 2 | 656.3384 |

Wildtype peptides

| Sequence | Start AA | End AA | Score | z | Apex Int. (Posit) | Obs.m/z |
|---|---|---|---|---|---|---|
| K.SYSCQiTHEGSTVEK.T | 642 | 656 | 469.28 | 3 | 1.283e... | 571.58. |
| K.SYSCQiTHEGSTVEK.T | 642 | 656 | 469.28 | 3 | 1.283e... | 571.58. |
| K.SYSCQiTHEGSTVEK.T | 642 | 656 | 504.62 | 3 | 1.283e... | 571.58. |
| K.SYSCQiTHEGSTVEK.T | 642 | 656 | 466.40 | 3 | 1.283e... | 571.58. |
| K.SYSCQiTHEGSTVEK.T | 642 | 656 | 355.48 | 3 | 1.283e... | 571.58. |
| K.SYSCQiTHEGSTVEK.T | 642 | 656 | 273.45 | 3 | 1.283e... | 571.58. |
| K.SYSCQiTHEGSTVEK.T | 642 | 656 | 294.47 | 3 | 1.283e... | 571.58. |
| K.SYSCQiTHEGSTVEK.T | 642 | 656 | 192.76 | 3 | 1.283e... | 571.58. |
| K.SYSCQiTHEGSTVEK.T | 642 | 656 | 110.70 | 3 | 1.283e... | 571.58. |
| K.SYSCQiTHEGSTVEK.T | 642 | 656 | 158.45 | 3 | 1.283e... | 571.58. |
| K.SYSCQiTHEGSTVEK.T | 642 | 656 | 164.04 | 3 | 1.283e... | 571.58. |

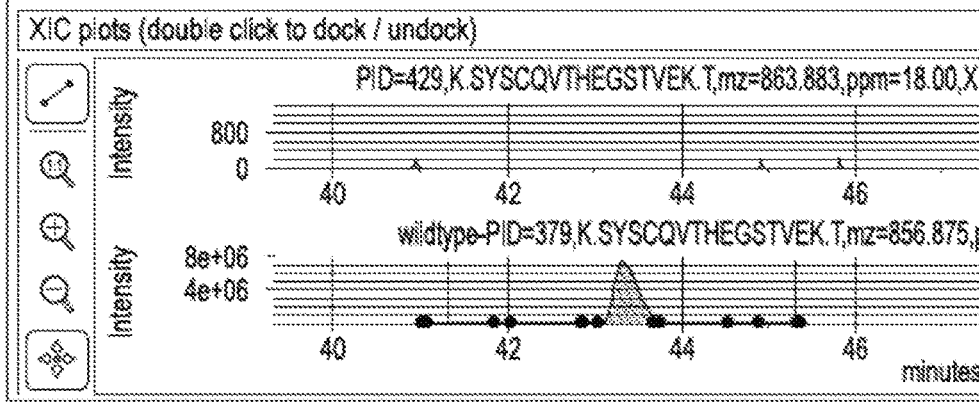

FIG. 6A

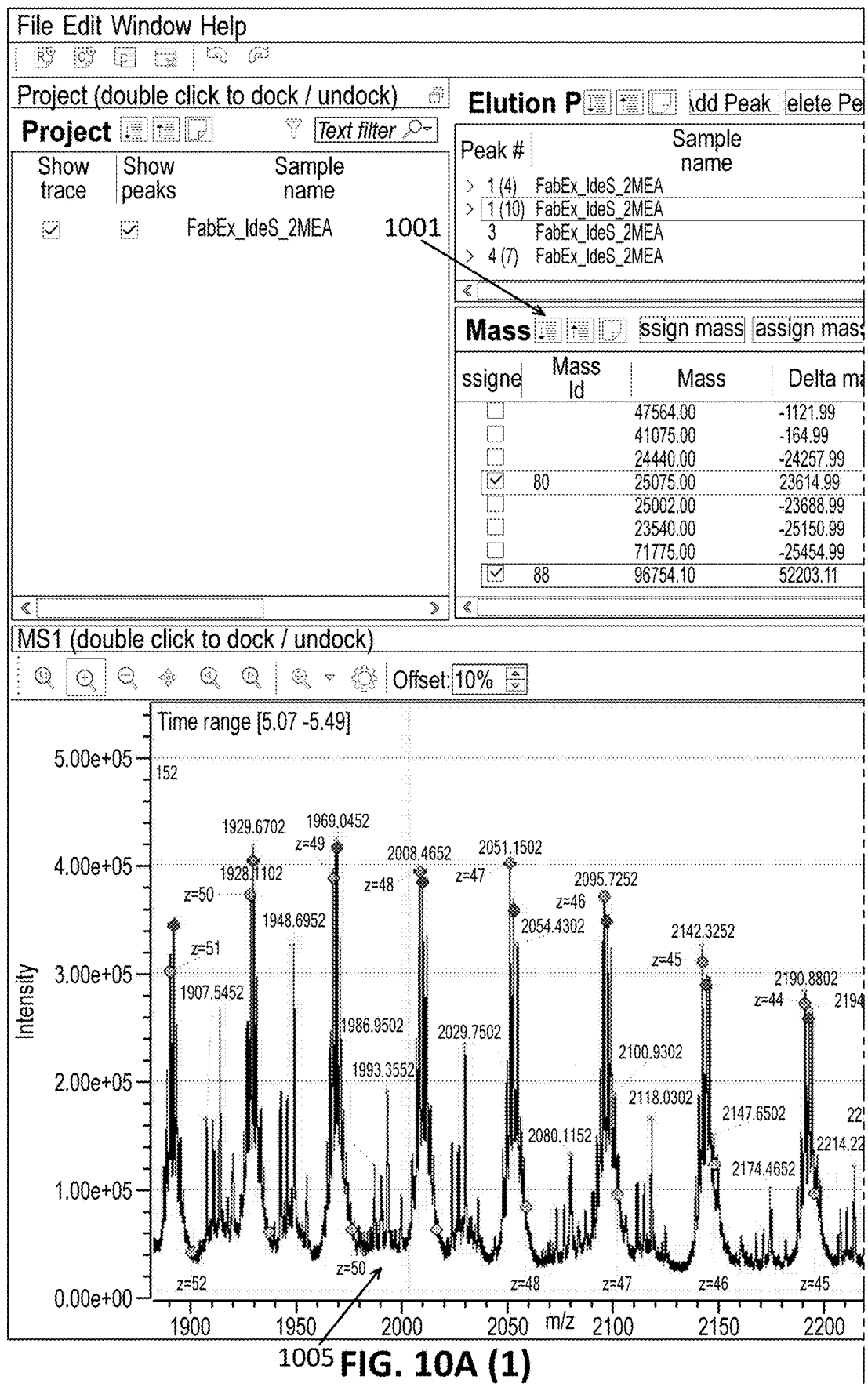
FIG. 10A (1)

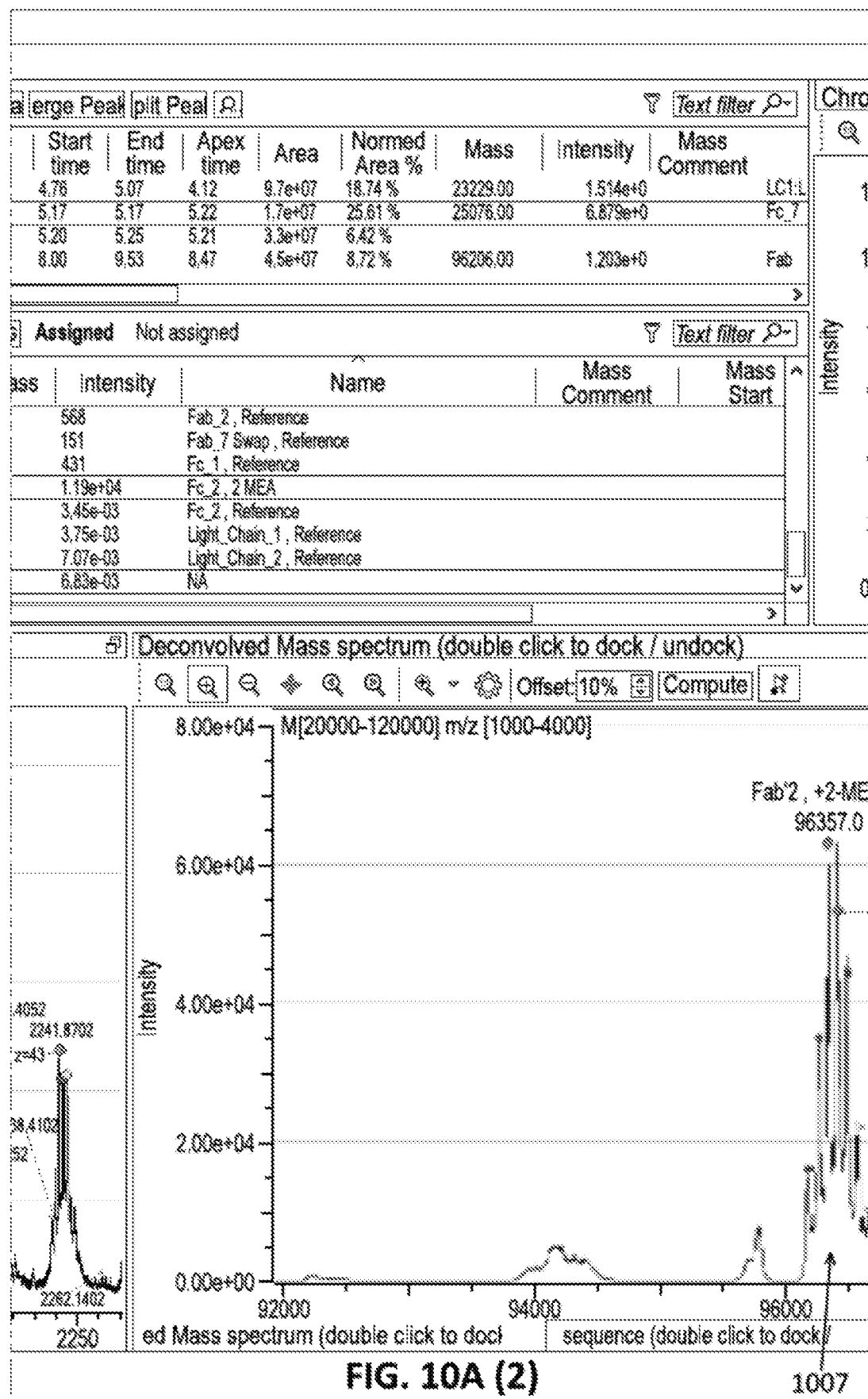
FIG. 10A (2)

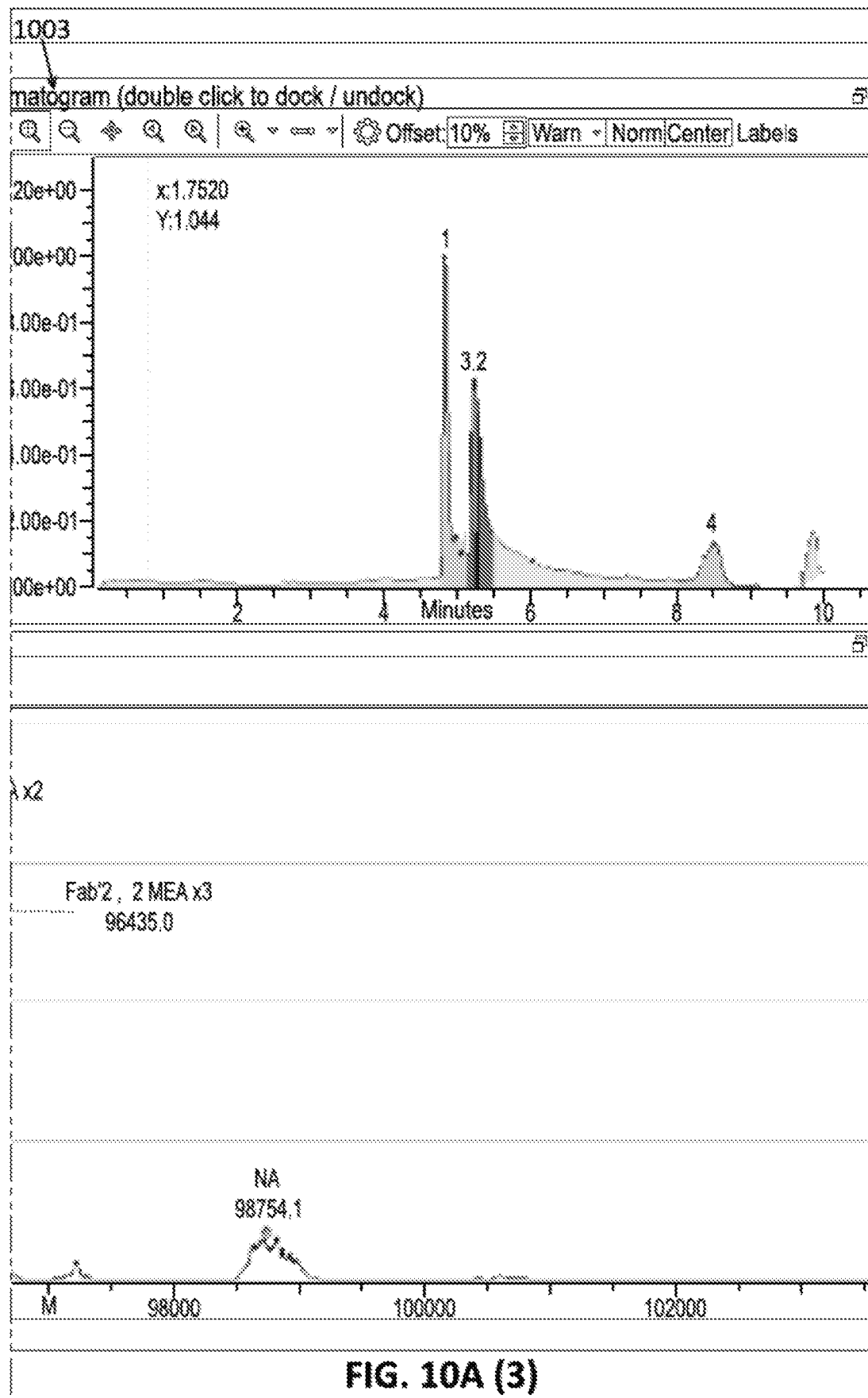
FIG. 10A (3)

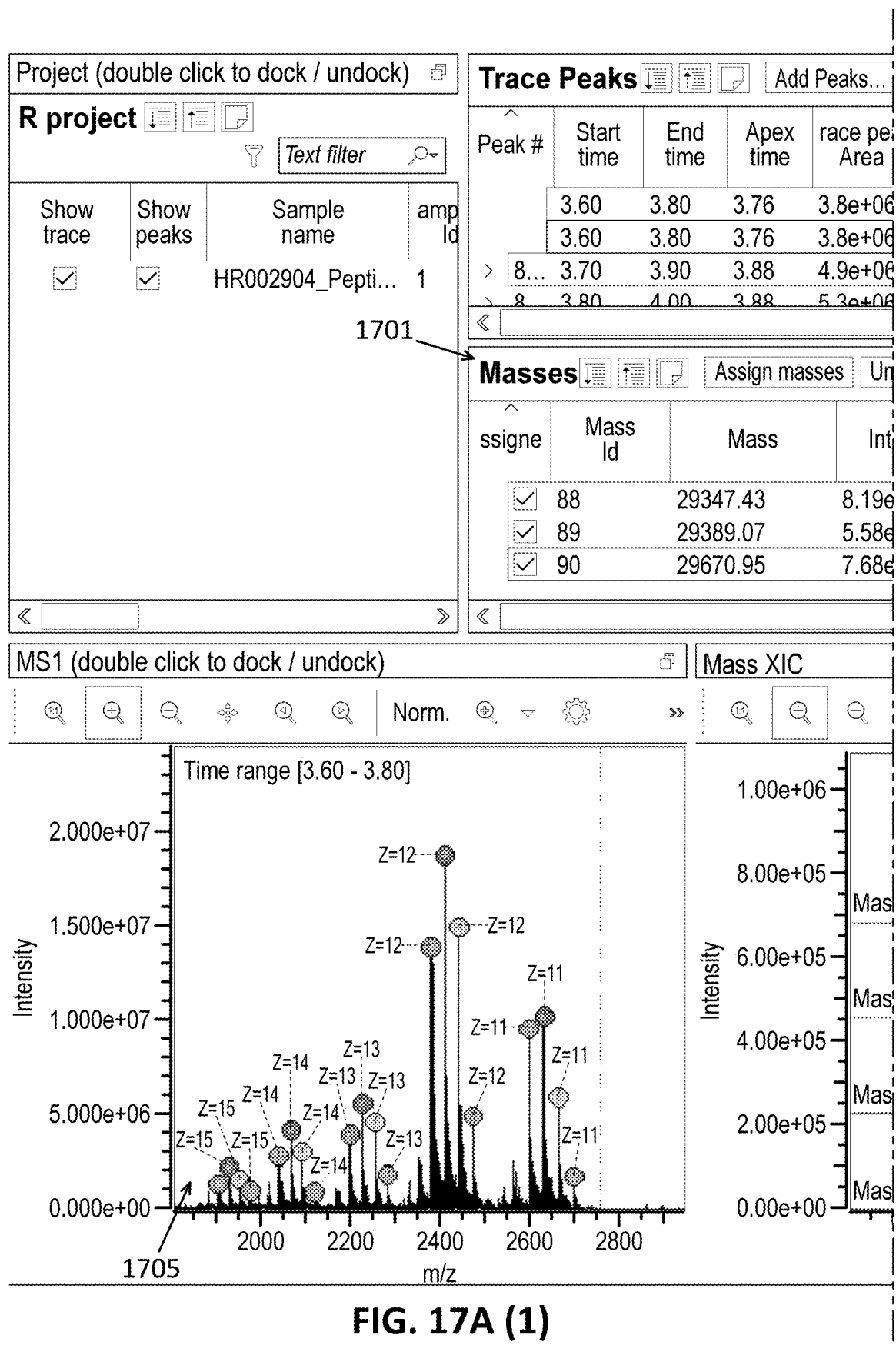
FIG. 17A (1)

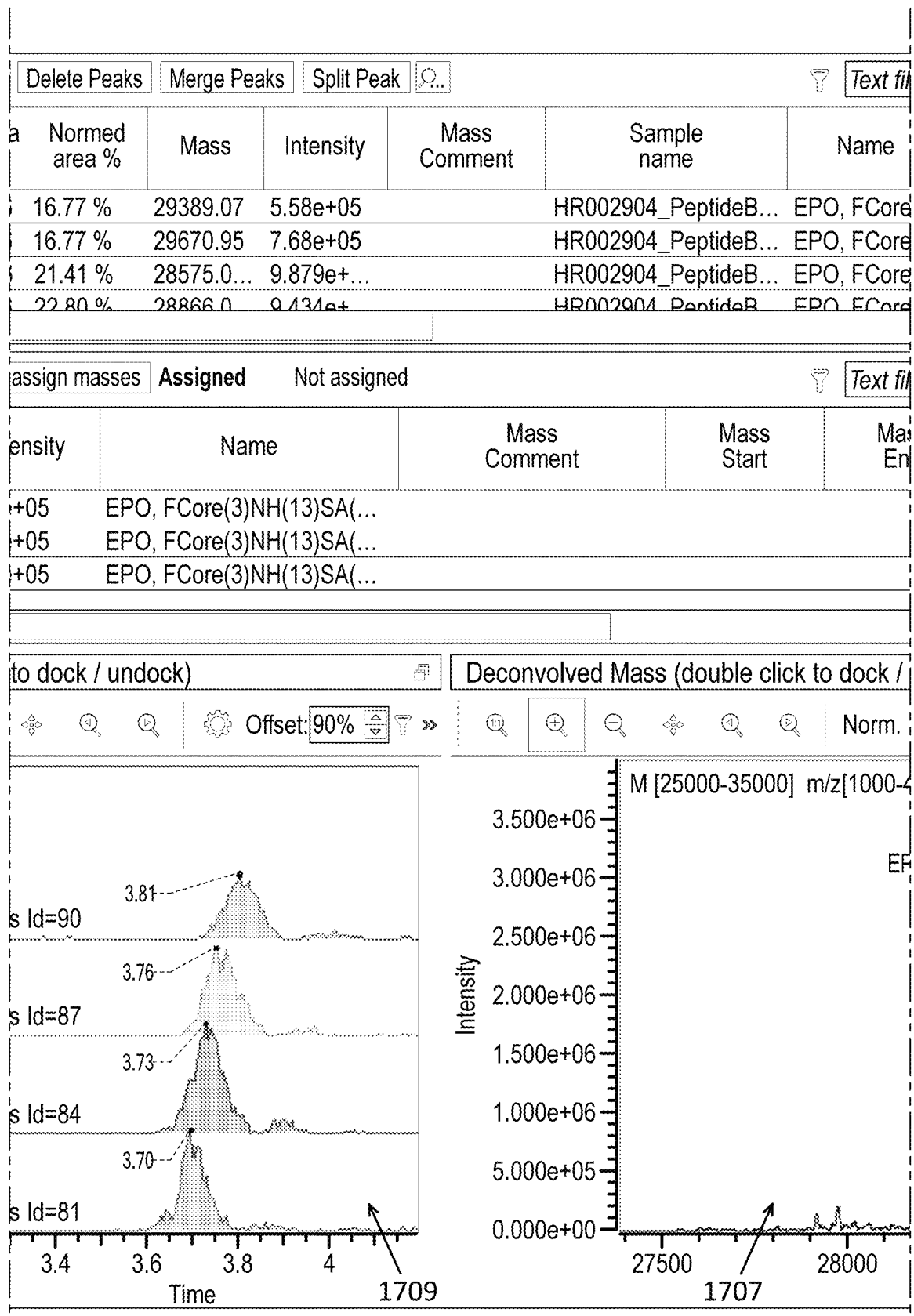
FIG. 17A (2)

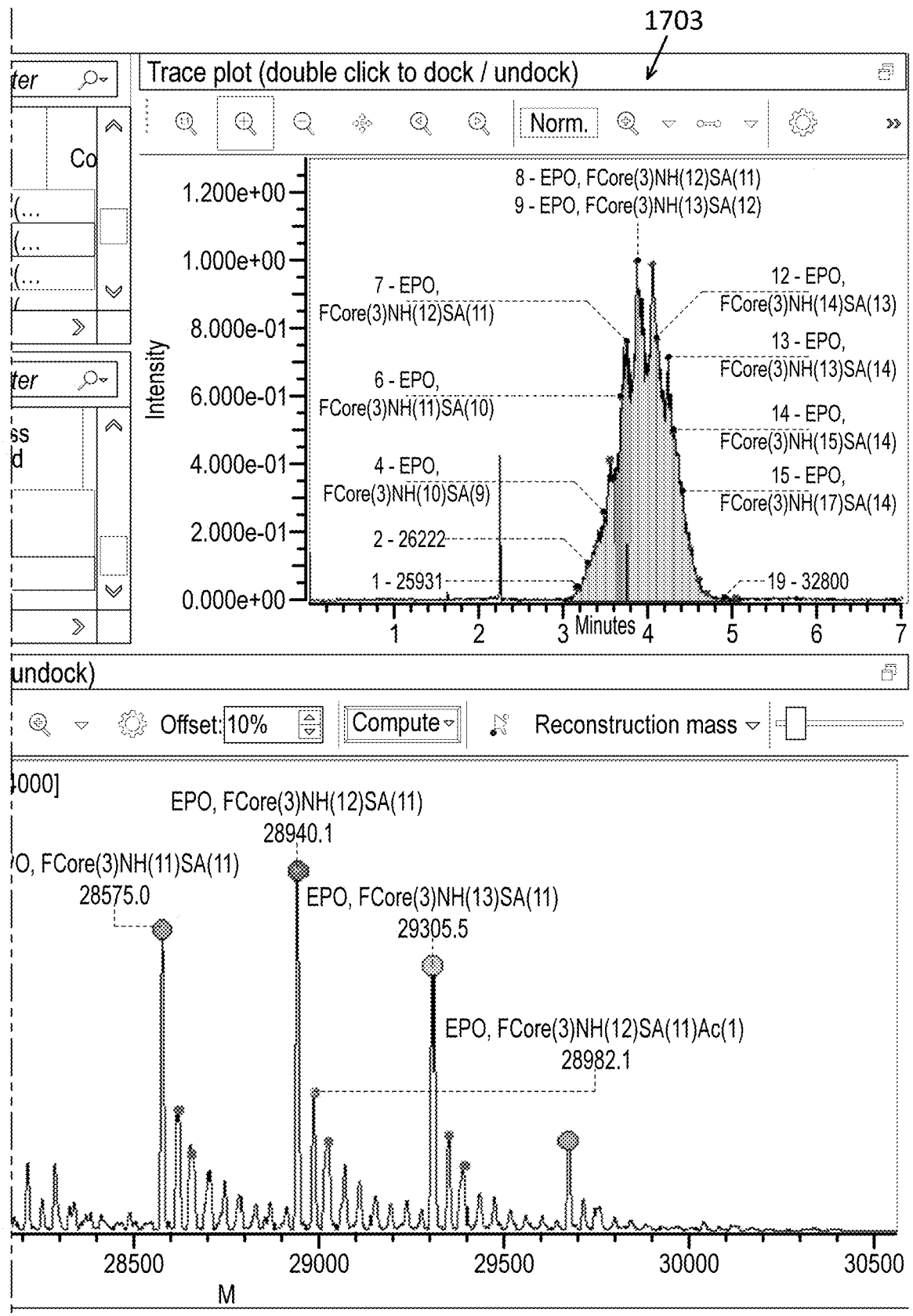
FIG. 17A (3)

INTERACTIVE ANALYSIS OF MASS SPECTROMETRY DATA INCLUDING PEAK SELECTION AND DYNAMIC LABELING

CROSS REFERENCE TO RELATED APPLICATIONS

This patent application is a continuation-in-part of U.S. patent application Ser. No. 17/240,996, titled "INTERACTIVE ANALYSIS OF MASS SPECTROMETRY DATA INCLUDING PEAK SELECTION AND DYNAMIC LABELING," filed on Apr. 26, 2021, now U.S. Pat. No. 11,626,274, which is a continuation-in-part of U.S. patent application Ser. No. 16/773,857, titled "INTERACTIVE ANALYSIS OF MASS SPECTROMETRY DATA INCLUDING PEAK SELECTION AND DYNAMIC LABELING," filed on Jan. 27, 2020, now U.S. Pat. No. 10,991,558, which is a continuation of U.S. patent application Ser. No. 16/052,506, filed Aug. 1, 2018, titled "INTERACTIVE ANALYSIS OF MASS SPECTROMETRY DATA INCLUDING PEAK SELECTION AND DYNAMIC LABELING," now U.S. Pat. No. 10,546,736, which claims priority to U.S. Provisional Patent Application No. 62/540,031, filed Aug. 1, 2017, titled "INTERACTIVE ANALYSIS OF MASS SPECTROMETRY DATA INCLUDING PEAK SELECTION AND DYNAMIC LABELING," each of which is herein incorporated by reference in its entirety.

This application may be related to U.S. patent application Ser. No. 15/583,752, filed May 1, 2017, which is a continuation of U.S. patent application Ser. No. 14/306,020, filed Jun. 16, 2014 (now U.S. Pat. No. 9,640,376), each of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates to graphical user-interactive displays for use in MS-based analysis of protein impurities, as well as methods and software for generating and using such.

BACKGROUND

Due to the complexity of proteins and their biological production, characterization of protein pharmaceuticals ("biologics") poses much more demanding analytical challenges than do small molecule drugs. Biologics are prone to production problems such as sequence variation, misfolding, variant glycosylation, and post-production degradation including aggregation and modifications such as oxidation and deamidation. These problems can lead to loss of safety and efficacy, so the biopharmaceutical industry would like to identify and quantify variant and degraded forms of the product down to low concentrations, plus obtain tertiary structure information. Because of the rapidly increasing power of mass spectrometry (MS), an MS-based platform for comprehensive measurement of almost all the relevant drug's physical characteristics is now conceivable. A crucial piece of such a platform is data analysis software focused to address the needs of the biopharmaceutical industry.

At every stage in the development and manufacture of a protein pharmaceutical, there is a need to characterize recombinantly produced protein molecules. This need arises in new product development, biosimilar (generic) product development, and in quality assurance for existing products. With the first generation of protein drugs just emerging from patent protection, and generic manufacturers rushing to enter the marketplace, assays and regulatory guidelines for biosimilarity have become a matter of some urgency. Over 30 branded biologics with worldwide sales >$50B will come off patent in 2011-2015, and the biosimilars markets is expected to grow to about $4B by 2015.

Quality assurance for monoclonal antibodies, as an example, must consider primary structure, higher order structure, glycosylation and heterogeneity. Primary structure analyses can include total mass (as measured by MS), amino acid sequence (as measured by orthogonal peptide mapping with high resolution MS and MS/MS sequencing), disulfide bridging (as measured by non-reducing peptide mapping), free cysteines (as measured by Ellman's or peptide mapping), and thioether bridging (as measured by peptide mapping, SDS-PAGE, or CGE). Higher order structure can be analyzed using CD spectroscopy, DSC, H-D-exchange, and FT-IR. Glycosylation requires identification of glycan isoforms (by NP-HPLC-ESI-MS, exoglycosidase digestion, and/or MALDI TOF/TOF), sialic acid (by NP-HPLC, WAX, HPAEC, RP-HPLC) and aglycolsylation (by CGE and peptide mapping). Heterogeneity analyses must take into consideration C- and N-terminal modifications, glycation of lysine, oxidation, deamidation, aggregation, disulfide bond shuffling, and amino acid substitutions, insertions and deletions. The large variety of assays and techniques gives some idea of the daunting analytical challenge. As early as 1994, Russell Middaugh of Merck Research Laboratories (Middaugh, 1994) called for a single comparative analysis in which "a number of critical parameters are essentially simultaneously determined". We believe that mass spectrometry (MS) now largely answers this call, because it can cover most of the physicochemical properties required for molecular analysis.

One of the problems with MS-based assays, however, is the lack of high-quality data analysis software. Unlike slow gel-based peptide mapping, which allows human visual comparison, MS generally relies on automatic data analysis, due to the huge numbers of spectra (often >10,000/hour), the high accuracy of the measurements (often in the 1-10 ppm range), and the complexity of spectra (100s of peaks spanning a dynamic range >1000). There are a large number of programs for "easy" MS-based proteomics, for example, SEQUEST, Mascot, X!Tandem, etc., but these programs were not designed for deep analysis of single proteins, and are incapable of difficult analytical tasks such as characterizing mutations, glycopeptides, or metabolically altered peptides. Moreover, the programs just named are all identification tools and must be coupled with other programs such as Rosetta Elucidator (now discontinued), Scaffold, or Thermo Sieve for differential quantification. There are also specialized tools such as PEAKS for de novo sequencing, along with a host of academic tools. The confusing array of software tools poses an obstacle to biotech companies adopting MS-based assays.

The methods and systems described herein free up the time of technical staff for additional projects while reducing staff frustration with the analysis process. Prior to the present methods and systems, sequence variant analysis (SVA) used a cumbersome combination of several existing software tools, supplemented with the use of spreadsheet macros. In contrast, described herein is an integrated approach providing a single user-friendly dashboard where one can identify false positives and quantify true positives efficiently. This gives greater confidence to the user and drastically reduces the time required to distinguish true from false positive identifications. Drug substance analyses are generally on the critical path of development, and projects are often gated by the analysis of a production run. Any time saving that leads to earlier commercialization of a drug brings significant monetary benefits to the company, not to mention the therapeutic benefits of bringing novel treatments to the patients as early as possible.

Described herein are methods and systems (including user interfaces, software, etc.) for interactively allowing a user to distinguish signal from even noisy spectra. Described herein are methods and apparatuses (including systems, devices, user interfaces, software, and the like) that may address the needs discussed above.

SUMMARY OF THE DISCLOSURE

Described herein are graphical user-interactive displays for use in MS-based analysis of protein impurities, as well as methods and software for generating and using such. In particular, described herein are interactive user interfaces that allow the user to select one or more points or regions of a deconvolved mass spectrum, and immediately and interactively show corresponding points (e.g., peaks) corresponding to the selected charged states to look at the deconvolved mass. The peaks may be displayed in a color corresponding to the selected point or region, and may be shown in multiple views. Alternatively or additionally, or other markers may be displayed on or over the spectra (e.g., in the MS1 spectra), and the user may determine if the resulting peaks corresponding to the selected point (e.g., charge state) look reasonable. By allowing interactive highlighting from the deconvolved mass and showing the resulting "peaks" overlaid on the actual, experimentally determined, peaks, (e.g., in a window showing the MS1 spectra, an additional MS window, mass over change spectrum, neutral mass spectrum, etc.), the user may use the resulting map overlay (e.g., peaks) to determine if the resulting pattern is reasonable, given their prior knowledge of the material being examined. For example, by selecting a particular charge, the user may interactively select various points and observe the resulting pattern of markers corresponding to the distribution of the selected charge.

Although the resulting peaks may not be "real" (e.g., may not correspond to a real peak), the display allows the user to examine the pattern distribution on the actual experimental data and distinguish for herself or himself if it is realistic or close to the actual or expected peaks.

For example, a user may highlight a deconvolved mass (from an image or window showing the deconvolved mass, or from a table or listing of the deconvolved mass) and the user interface may immediately and interactively highlight, (e.g., in the MS1 and/or other window(s)), the resulting predicted peaks as colored dots or points on the graphs (e.g., spectra) displayed in each window.

More than one point or region may be selected at any particular time, and additional colored "dots," lines, or other annotations corresponding to each selected point or region may be overlaid on to the images within each window. The resulting highlighted information may be printed or displayed, and/or may be used as part of a report output by the apparatus, including the user interface. The resulting pattern of highlighted positions (e.g., dots) may be calculated by using the mass (e.g., the selected mass); the mass may be divided by the charge, and the m/z calculation may be readily performed (e.g., if a charge 2 has 2 protons, etc. add the mass of a proton and divide). The position of the dots (markers) may be determined and displayed on the one or more window displays. The range of values displayed may be pre-set or user selected. The user interface allowing the interactive selection and marking of resulting peaks is surprisingly helpful in interpreting the data, allowing a user to directly visualize and inspect the data and distinguish real peaks from background, even when the background is otherwise high. Any of these methods and apparatuses may also display charge labels.

For example, a user may select a mass from the list of masses, and highlight the resulting peaks on the deconvolved mass spectrum and any other window, allowing cross-comparison between the windows. This comparison may be done in real time, and interactively, as the user may select and/or deselect one or more points and the resulting peaks may be shown on the data in real time.

One aspect of the methods and apparatuses (including user interfaces) described herein provides a user-interactive display comprising an extracted ion chromatogram (XIC), an MS1 spectrum and an MS2 spectrum, all simultaneously representing a user-selected peptide. Another aspect provides a user interactive display simultaneously presenting paired spectra (XIC, MS1 and/or MS2) for a variant peptide and its corresponding wildtype counterpart.

One aspect of the invention provides non-transitory machine-readable media that store instructions, which, when performed by a machine, cause the machine to perform the methods and operations described herein. For example, non-transitory machine-readable media may store instructions such as and including: (a) receiving a data file comprising mass spectrometry (MS) data for a sample comprising one or a mixture of molecules such as a reference molecule and one or more variant molecules, wherein each variant molecule has a chemical modification relative to the reference molecule, and wherein the MS data comprises a plurality of spectral representations; (b) providing an assembly of molecular identifications, wherein each molecular identification correlates a spectral representation with the reference molecule and a modification state, wherein the modification state describes the chemical modification for a variant molecule relative to the reference molecule and wherein the modification state is null for the reference molecule; (c) selecting a molecular identification based on user-input; and (d) simultaneously displaying a first arrangement of a plurality of spectral representations, wherein a first spectral representation of the first arrangement is correlated to the selected molecular identification and a second spectral representation of the first arrangement is correlated to a first molecular identification having the same reference molecule but different modification state.

An additional aspect of the invention provides methods for displaying mass spectrometry data comprising: (a) receiving a data file comprising mass spectrometry (MS) data for a sample comprising a mixture of molecules comprising a reference molecule and one or more variant molecules, wherein each variant molecule has a chemical modification relative to the reference molecule, and wherein the MS data comprises a plurality of spectral representations; (b) providing an assembly of molecular identifications, wherein each molecular identification correlates a spectral representation with the reference molecule and a modification state, wherein the modification state describes the chemical modification for a variant molecule relative to the reference molecule and wherein the modification state is null for the reference molecule; (c) selecting a molecular identification based on user-input; and (d) simultaneously displaying a first arrangement of a plurality of spectral representations, wherein a first spectral representation of the first arrangement is correlated to the selected molecular identification and a second spectral representation of the first arrangement is correlated to a first molecular identification having the same reference molecule but different modification state.

The reference molecule preferably is a molecule selected from the group consisting of polypeptides, oligonucleotides, lipids, organic polymers, pharmaceutical excipients and growth media components. In a preferred implementation, the sample comprises a protein or protein mixture subjected to digestion by a proteolytic enzyme and the reference molecule is a peptide.

In some implementations, the assembly of molecular identifications is presented in tabular form, wherein each line of the tabular form represents the reference molecule or a single variant molecule, and wherein the step of selecting a molecular identification comprises selecting a line of the tabular form. The assembly of molecular identifications can be populated from results of a computational search of observed spectra with respect to a database or library of recorded spectra. The tabular form can comprise a variety of fields, for example, a field providing the modification state of each peptide or a field providing a validation status of each molecular identification. Examples of suitable modification states include, but are not limited to, modification states selected from the group consisting of unmodified, sequence variant, insertion, deletion, extension, oxidation, deamidation, conjugate, glycation, sulfation, and glycosylation. Examples of suitable validation statuses include, but are not limited to true-positive, false-positive and uncertain.

In some implementations, where the reference molecule is a peptide, the assembly of molecular identifications is a graphical representation of the protein, wherein the graphical representation of the protein comprises an amino acid sequence for the protein and a plurality of markers mapped to the amino acid sequence and representing peptides within the protein, and further wherein the step of selecting a peptide comprises user selection of a marker. Preferably, prior to data acquisition, the protein is subjected to controlled digestion to generate the peptide mixture. Typically the peptide mixture is a product of digestion of the protein with a proteolytic enzyme, however other methods of controlled digestion are contemplated. The peptides can be designated as wildtype or variant. A variant peptide can be modified relative to the corresponding wildtype (reference) peptide by a single amino acid substitution, a double amino acid substitution, oxidation, deamidation, glycosylation, a single amino acid deletion or a single amino acid insertion.

The first spectral representation and second spectral representation may be selected from the group consisting of MS1 spectra, MS2 spectra and extracted ion chromatogram (XIC). In some implementations, the first spectral representation is displayed immediately adjacent (i.e., immediately above, immediately below or immediately beside) the second spectral representation. Alternatively, the first spectral representation and second spectral representation are displayed sharing a single horizontal axis. In some implementations, the arrangement will comprise a third spectral representation correlated to a second molecular identification having the same reference molecule as the selected and first molecular identifications but a different modification state from both the selected and first molecular identifications.

The invention contemplates the inclusion of additional spectral representations in the arrangement, wherein the $n^{th}$ spectral representation is correlated to a $(n-1)^{th}$ molecular identification, wherein every spectral representation in the arrangement is correlated to a molecular identification sharing the same reference molecule, but optionally varying in modification states.

In many implementations, the operation or method will further comprise the step of simultaneously displaying a second arrangement of a plurality of spectral representations, wherein a first spectral representation of the second arrangement is correlated to the selected molecular identification and a second spectral representation of the second arrangement is correlated to the first molecular identification. In a first implementation, the spectral representations of the first arrangement are MS1 spectra, and the spectral representations of the second arrangement are MS2 spectra. In a second implementation, the spectral representations of the first arrangement are MS1 spectra, and the spectral representations of the second arrangement are XIC. In a third implementation, the spectral representations of the first arrangement are MS2 spectra, and the spectral representations of the second arrangement are XIC.

One aspect of the invention provides non-transitory machine-readable media that store instructions, which, when performed by a machine, cause the machine to perform operations comprising: (a) receiving a data file comprising mass spectrometry (MS) data for a sample, comprising a plurality of molecules, preferably a mixture of peptides produced by enzymatic digestion of a protein, wherein the MS data comprise spectra collected across a time range for the sample prior to and after fragmentation; (b) displaying a layout of a plurality of views in a graphical user interface; and (c) controlling the layout of the plurality of views with an user-interactive selector, wherein a single user action selects a molecule and simultaneously updates the plurality of views to display the XIC, MS1 spectrum and MS2 spectrum associated with the selected molecule. The plurality of views comprises: (1) an extracted mass chromatogram (XIC) based on the data file showing a measure of input molecules as a function of time, the chromatogram comprising a plurality of XIC peaks, wherein each peak is associated with one or more molecules, each of which is associated with a plurality of MS1 and MS2 spectra; (2) an MS1 spectrum based on data collected for the sample prior to fragmentation, wherein the spectrum comprises a plurality of MS1 peaks, wherein one or more peaks are each associated with a corresponding MS2 spectrum; and (3) an MS2 spectrum based on data collected for the sample after fragmentation, wherein the spectrum corresponds to a peak in the displayed MS1.

Another aspect of the invention provides a method for displaying a plurality of user-interactive MS-based peptide identifications, the method comprising: (a) receiving a data file comprising mass spectrometry (MS) data for a sample, comprising a plurality of molecules, preferably a mixture of peptides produced by enzymatic digestion of a protein, wherein the MS data comprise spectra collected across a time range for the sample prior to and after fragmentation; (b) displaying a layout of a plurality of views in a graphical user interface; and (c) controlling the layout of the plurality of views with a user-interactive selector, wherein a single user action selects a molecule and simultaneously updates the plurality of views to display the XIC, MS1 spectrum and MS2 spectrum associated with the selected molecule. The plurality of views comprises: (1) an extracted mass chromatogram (XIC) based on the data file showing a measure of input molecule as a function of time, the chromatogram comprising a plurality of XIC peaks, wherein each peak is associated with one or more molecules, each of which is associated with a plurality of MS1 and MS2 spectra; (2) an MS1 spectrum based on data collected for the sample prior to fragmentation, wherein the spectrum comprises a plurality of MS1 peaks, wherein one or more peaks are each associated with a corresponding MS2 spectrum; and (3) an MS2 spectrum based on data collected for the sample after fragmentation, wherein the spectrum corresponds to a peak in the displayed MS1 spectrum.

In some implementations, the user-interactive selector is a list of molecular identifications, preferably peptide indications, in tabular form, wherein each line of the tabular form represents a single molecule from the list, wherein user-selection of a molecule from the list automatically displays the XIC, MS1 spectrum and MS2 spectrum associated with the molecule. In many implementations, each molecular identification in the tabular form correlates a spectral representation (XIC, MS1 spectrum or MS2 spectrum) with a reference molecule and a modification state. Typically the modification state describes the chemical modification for a variant molecule relative to the reference molecule. The modification state would be null for the reference molecule.

Preferably the selected molecule is a peptide. Typically, the peptide is present in a peptide mixture that is a product of digestion of a protein with a proteolytic enzyme, however other methods of controlled digestion are contemplated. The list of peptide identifications can be populated from results of a computational search of observed spectra with respect to a sequence database or library of recorded spectra. In another implementation, the user-interactive selector is a graphical representation of the protein. For example, the graphical representation of the protein can comprise an amino acid sequence for the protein and a plurality of markers mapped to the amino acid sequence and representing peptides within the protein, and further wherein user selection of a marker automatically displays the XIC, MS1 spectrum and MS2 spectrum associated with the peptide represented by the marker. The peptide mapped to the amino acid sequence can be modified relative to the amino acid sequence, and the modification would be graphically depicted on the marker for the peptide. In yet another implementation, the user-interactive selector is an indicator for selecting an XIC peak.

In certain implementations, the data comprising MS data is collected by a tandem mass spectrometer. In other implementations, the MS data is collected as MS1 data prior to fragmentation on a first mass spectrometer and MS2 data after fragmentation on a second mass spectrometer.

In some implementations, the time range is generated in the context of a separation method applied to the sample. The separation method can be, but is not limited to any one of the group consisting of liquid chromatography (LC), gas chromatography, ion mobility, gel electrophoresis and capillary electrophoresis.

Yet another aspect of the invention provides non-transitory machine-readable media that store instructions, which, when performed by a machine, cause the machine to perform operations comprising: (a) receiving a data file comprising mass spectrometry (MS) data for a sample comprising a mixture of a reference molecule and one or more variant molecules, wherein each variant molecule has a chemical modification relative to the reference molecule, and wherein the MS data comprises a plurality of spectral representations; (b) providing an assembly of molecular identifications, wherein each molecular identification correlates a plurality of spectral representations with the reference molecule and a modification state, wherein the plurality of spectral representations comprise an extracted ion chromatogram (XIC), an MS1 spectrum and an MS2 spectrum, and wherein the modification state describes the chemical modification for a variant molecule relative to the reference molecule and wherein the modification state is null for the reference molecule; (c) selecting a molecular identification based on user-input; and (d) displaying an arrangement of a plurality of views in a graphical user interface. The plurality of views comprises: (1) a first XIC correlated to the selected peptide immediately adjacent to a second XIC correlated to a first molecular identification having the same reference molecule as the selected peptide but different modification state; (2) a first MS1 correlated to the selected peptide immediately adjacent to a second MS1 correlated to a first molecular identification having the same reference molecule as the selected peptide but different modification state; and (3) a first MS2 correlated to the selected peptide immediately adjacent to a second MS2 correlated to a first molecular identification having the same reference molecule as the selected peptide but different modification state.

Another aspect of the invention provides a method for displaying mass spectrometry data, the method comprising: (a) receiving a data file comprising mass spectrometry (MS) data for a sample comprising a mixture of a reference molecule and one or more variant molecules, wherein each variant molecule has a chemical modification relative to the reference molecule, and wherein the MS data comprises a plurality of spectral representations; (b) providing an assembly of molecular identifications, wherein each molecular identification correlates a plurality of spectral representations with the reference molecule and a modification state, wherein the plurality of spectral representations comprise an extracted ion chromatogram (XIC), an MS1 spectrum and an MS2 spectrum, and wherein the modification state describes the chemical modification for a variant molecule relative to the reference molecule and wherein the modification state is null for the reference molecule; (c) selecting a molecular identification based on user-input; and (d) displaying an arrangement of a plurality of views in a graphical user interface. The plurality of views comprises: (1) a first XIC correlated to the selected peptide immediately adjacent to a second XIC correlated to a first molecular identification having the same reference molecule as the selected peptide but different modification state; (2) a first MS1 correlated to the selected peptide immediately adjacent to a second MS1 correlated to a first molecular identification having the same reference molecule as the selected peptide but different modification state; and (3) a first MS2 correlated to the selected peptide immediately adjacent to a second MS2 correlated to a first molecular identification having the same reference molecule as the selected peptide but different modification state.

One aspect of the invention provides non-transitory machine-readable media that store instructions, which, when performed by a machine, cause the machine to perform operations comprising: (a) receiving a data file comprising mass spectrometry (MS) data for a sample comprising a peptide mixture of a protein wherein the peptide mixture comprises wildtype peptide and variant peptide, and wherein the MS data comprise spectra collected across a time range for the sample prior to and after fragmentation; (b) providing an assembly of molecular identifications, wherein each peptide identification correlates a peptide with a peak in one or more spectral representations and further wherein each peptide identification categorizes the peptide as a wildtype peptide or a variant peptide, wherein a variant peptide corresponds to a wildtype peptide but is modified relative to that wildtype peptide; (c) selecting a peptide based on user-input; (d) identifying a matched peptide, wherein if the user-selected peptide is a variant peptide, then the matched peptide is the corresponding wildtype peptide, and if the user-selected peptide is a wildtype peptide, then the matched peptide is a corresponding variant peptide; and (e) displaying a layout of a plurality of views in a graphical user interface. The said plurality of views comprises: (1) a first extracted mass chromatogram (XIC) comprising a peak representing the selected peptide and a second XIC comprising a peak representing the matched peptide, wherein each XIC is based on the data file and displays a measure of peptide as a function of time; (2) a first MS1 spectrum comprising a peak representing the selected peptide and a second MS1 spectrum comprising a peak representing the matched peptide, wherein each MS1 spectrum is based on data collected for the sample prior to fragmentation; and (3) a first MS2 spectrum comprising a peak representing the selected peptide and a second MS2 spectrum comprising a peck corresponding to the matched peptide, wherein each MS2 spectrum is based on data collected for the sample after fragmentation.

The software works by the user considering each putative identification of a variant/modification and using all the information interactively brought together by the program to determine if the identification is true or false (validation). The user makes this decision and may also make comments. The software also makes room for one or more reviewer to enter their response and comments. Results (tables and figures) may be exported for report generation and sharing with colleagues. For example, described herein are methods for interactively displaying mass spectrometry data. These methods may also be referred to herein as methods for analyzing (or machine-assisted analysis), including graphical analysis, of mass spectrometry data. For example, a method may include: receiving a data file comprising mass spectrometry (MS) data for a sample comprising a molecule; simultaneously displaying a plurality of visual representations derived from the received data, the plurality of visual representations comprising: a first visual representation comprising estimated or calculated masses from the received data file, a second visual representation comprising a distribution of mass/charge (m/z) values estimated or calculated from the received data file, and a third visual representation comprising a deconvolved mass spectrum estimated or calculated from the received data file; receiving a user-selected mass value from one of the first visual representation, the second visual representation or the third visual representation; and displaying a labeled mark corresponding to the selected mass value on one or both of the first and third visual representations, and simultaneously displaying the labeled mark corresponding to the selected mass on each of a plurality of sites on the distribution of m/z, wherein the labeled mark corresponds uniquely to the user-selected mass value.

Receiving a data file may include receiving the data file electronically, via wired or wireless connection, into a memory accessible by the processor performing or controlling most or all of the other steps. Receiving may include uploading, importing, accessing, etc. The mass spectrometry (MS) data may be a file, database, etc. The MS data may include MS data provided by a mass spectrometer or multiple mass spectrometers. The MS data may include MS information for a single sample comprising a molecule, e.g., one or more molecules, or for multiple samples.

Simultaneously displaying the visual representations may include displaying at the same or approximately the same time (e.g., on a single screen or multiple screens). The visual representations may be separate windows, as described herein, which may be displayed adjacent (e.g., tiles), overlapping or partially overlapping. In general, as information (e.g., markers, the time range and other scaling) is modified, automatically and/or by the user on one of the visual representations (e.g., windows or displays) the other visual displays may be concurrently and/or simultaneously modified. This concurrent display and/or modification between the visual representations is very useful, as it may aid the user in immediately seeing connections between the different visual displays and data types that may otherwise be difficult to understand and see. In particular the updating and modifications performed between the various displays is not necessarily a simple (e.g., 1:1) transfer of information/ modification between the different visual representations. For example, in particular identifying a mass value and marking the corresponding mass/charge (m/z) region in the visual representations of a distribution of m/z values may require the method and/or apparatus to interpret the m/z values and determine where to place the marker in the m/z mapping. This is described in greater detail below.

Any appropriate marking may be used. For example, the marking may include a color dot, and/or an annotated colored dot.

The methods and apparatuses described herein are typically interactive. In particular, these methods and apparatuses may be configured to receive user input and selection of one or more mass values in order to coordinate the marking of corresponding values across and between the various visual representations. In some variations, receiving the user-selected mass value may comprise identifying a mass value from a user-selected region of the second visual representation or the third visual representation. For example, the user may draw, outline, drop, move, expand, etc. a visual area such as a box, circle, oval, rectangle, etc., around a region of the distribution of mass/charge (m/z) values (the second visual representation) or on a region of the visual representation comprising a deconvolved mass spectrum (e.g., the third visual representation). In some variations, the mass values may be selected from the first visual representation comprising the estimated or calculated masses from the received data file. One or more mass values may be selected.

The mass values may be determined from a selected region, e.g., by applying thresholding. For example, the user may manually (or the method/apparatus may automatically, based on pre-set parameter values) determine a fixed (preset) or variable number of mass values to mark between the visual representations. The user may select a region and the method or apparatus may apply a manual or automatically selected threshold so that all masses above the threshold are mass values that are labeled. For example, identifying the mass value from the user selected range may comprise identifying a peak mass value from the user-selected range. The peak mass value may be the highest mass value within the selected range. In some variations the user may manually (or the apparatus/method may automatically) indicate a number of the highest mass values to mark.

For example, receiving the user-selected mass value may comprise identifying a plurality of mass values from a user-selected region of the second visual representation or the third visual representation; and wherein displaying the labeled mark comprises simultaneously displaying a separate labeled mark corresponding to each of the mass values of the plurality of mass values. In some variation the user may modify a default number (e.g., 2, 3, 4, 5, 6, 7, 8, 9, or more, etc.) of mass values from the user-selected range(s).

In some variations, all of the mass values (e.g., mass peaks in a selected region of the deconvolved mass spectrum) may be marked.

For example, receiving the user-selected mass value may comprise receiving a plurality of mass values and wherein displaying the labeled mark comprises simultaneously displaying a separate labeled mark corresponding to each of mass values of the plurality of mass values.

In any of these variations, the point being labeled on the m/z display may be determined from within a range of values. Thus, the x coordinate of the marking location may be modified (adjusted right or left, within an adjustment range) so that it maps to the nearest peak within the adjustment range. The adjustment range (e.g., "range") may depend on the computation used to determine the m/z mapping from the MS data. In some variations the adjustment range is a constant range. The center of the range may be calculated to be the actual value determined for the m/z value(s) for each mass value from the MS data; the range may be +/- a percentage of this value (e.g., +/- about 5%, 2%, 1%, 0.5%, 0.1%, 0.05%, etc.). Note that the m/z marking placement may not always correspond to a peak, but may simply be the highest value within the range. When isotope mapping (e.g., isotope peaks) are known, the placement of the marks may be adjusted using this information. For example, if isotope peaks are known, the method or apparatus may determine the expected charge values from even a single peak; with large masses, multiple charge estates may be used to deduce charge from multiple charge states.

For example, displaying the labeled marks may correspond to displaying the selected mass on the plurality of sites on the distribution of m/z, e.g., identifying a maximum amplitude within a predetermined range (e.g., the adjustment range) in the distribution of m/z and displaying the labeled mark on the maximum amplitude for each site of the plurality of sites.

A method for interactively displaying mass spectrometry data may include: receiving a data file comprising mass spectrometry (MS) data for a sample comprising a molecule; simultaneously displaying a plurality of visual representations derived from the received data, the plurality of visual representations comprising: a first visual representation comprising estimated or calculated masses from the received data file, a second visual representation comprises a distribution of mass/charge (m/z) values estimated or calculated from the received data file, and a third visual representation comprising a deconvolved mass spectrum estimated or calculated from the received data file; receiving a user-selected set of mass values from one of the first visual representation, the second visual representation or the third visual representation, by the user selecting a range and automatically identifying a plurality of mass values from within the range; and displaying a labeled mark corresponding to each mass value of the user-selected set of mass values on one or both of the first and third visual representations, and simultaneously displaying a set of labeled marks corresponding to each of the mass values at a plurality of sites on the distribution of mass/charge (m/z), wherein displaying the set of labeled marks corresponding to each of the selected masses on the plurality of sites on the distribution of m/z comprises identifying a maximum amplitude within a predetermined range in the distribution of m/z and displaying the labeled mark on the maximum amplitude for each site of the plurality of sites.

Any of the methods described herein may be configured as non-transitory machine-readable media that store instructions, which, when performed by a machine, cause the machine to perform the method. Also described herein are systems for performing any of these methods, which may include any of these non-transitory machine-readable media that store the instructions for performing the method.

For example, a non-transitory machine-readable medium that stores instructions, which, when performed by a machine, cause the machine to perform operations comprising: receiving a data file comprising mass spectrometry (MS) data for a sample comprising a molecule; simultaneously displaying a plurality of visual representations derived from the received data, the plurality of visual representations comprising: a first visual representation comprising estimated or calculated masses from the received data file, a second visual representation comprising a distribution of mass/charge (m/z) values estimated or calculated from the received data file, and a third visual representation comprising a deconvolved mass spectrum estimated or calculated from the received data file; receiving a user-selected mass value from one of the first visual representation, the second visual representation or the third visual representation; and displaying a labeled mark corresponding to the selected mass value on one or both of the first and third visual representations, and simultaneously displaying the labeled mark corresponding the selected mass on each of a plurality of sites on the distribution of m/z, wherein the labeled mark corresponds uniquely to the user-selected mass value. As mentioned, displaying the labeled marks corresponding the selected mass on the plurality of sites on the distribution of m/z may comprise identifying a maximum amplitude within a predetermined range in the distribution of m/z and displaying the labeled mark on the maximum amplitude for each site of the plurality of sites.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6A-6C illustrate the dashboard (showing MS2, MS1 and XIC spectra, and Variant Peptide View, Wildtype Peptide View), with a peptide having a putative Val→Ile substitution highlighted.

FIGS. 10A(1)-10A(3) is an example of a dashboard showing multiple windows, including a mass listing from which three masses (two are visible) have been selected, Mass ID 80 and mass ID 88. A thirty second portion of the chromatogram has also been selected, and colored dots representing predicted peak positions using those masses are shown on the MS1 and deconvolved mass spectrum windows.

FIG. 16A shows the colored marker (e.g., dot) on the m/z curve, the dots overlap with each other. FIG. 16B shows the y-position of the colored markers adjusted to reflect a fraction of the m/z peak assigned to the corresponding marker.

FIGS. 17A(1)-17A(3) illustrate another example dashboard showing multiple windows, including a mass extracted ion chromatogram (XIC).

DETAILED DESCRIPTION

Figure 1:
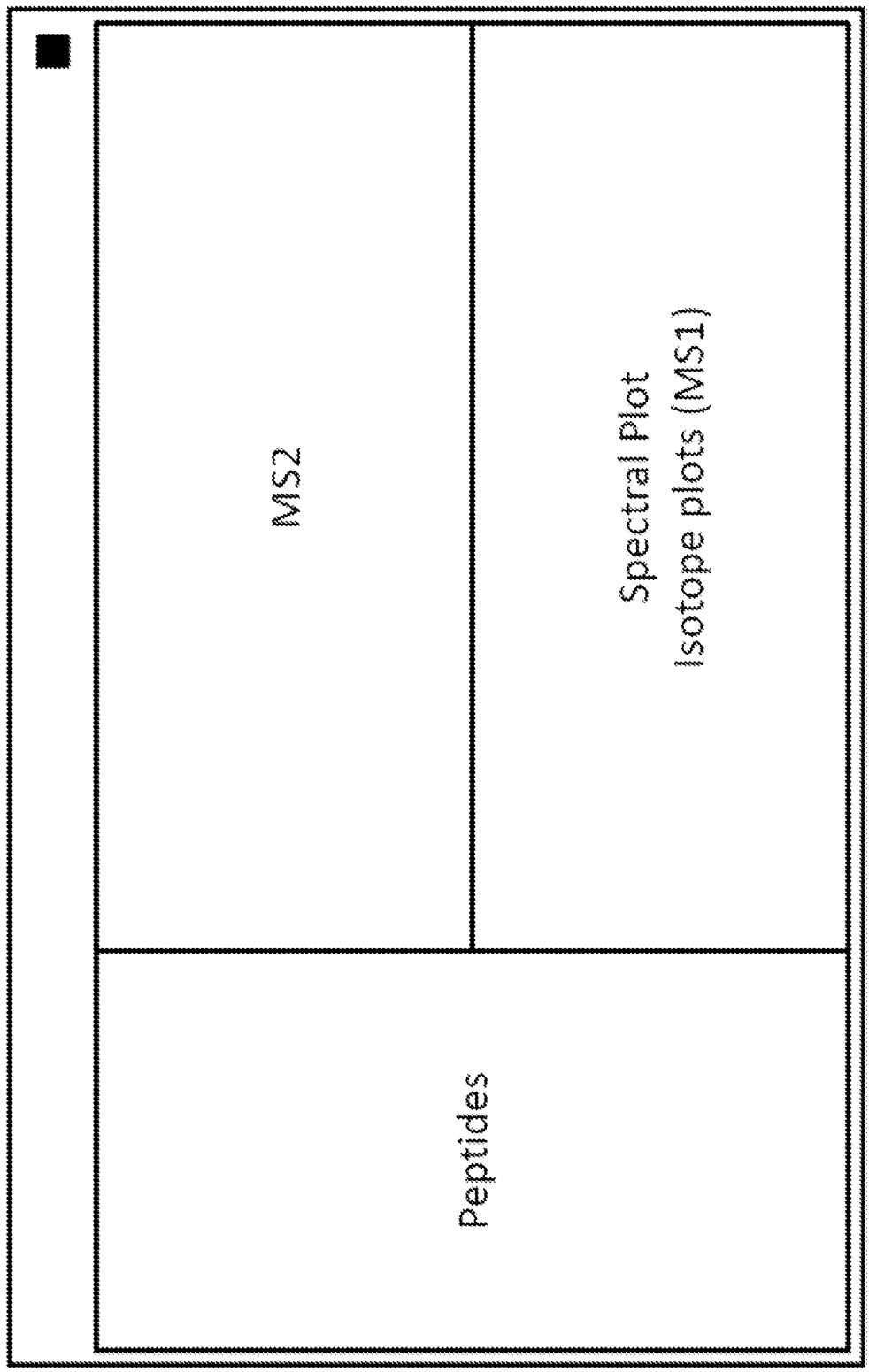
FIG. 1 provides a schematic diagram of the dashboard.

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

As used herein, "sequence variant" refers to any chemical change in a protein, peptide or peptide fragment relative to its wildtype counterpart. Sequence variants can include single or double amino acid substitutions, single amino acid insertions, single amino acid deletions, truncations, as well as oxidation, deamidation, glycosylation, and the like.

As used herein, the term "Mass Spectrometry" (MS) refers to a technique for measuring and analyzing molecules that involves ionizing or ionizing and fragmenting a target molecule, then analyzing the ions, based on their mass/charge ratios (m/z), to produce a mass spectrum that serves as a "molecular fingerprint". There are several commonly used methods to determine the mass to charge ratio of an ion, some measuring the interaction of the ion trajectory with electromagnetic waves, others measuring the time an ion takes to travel a given distance, or a combination of both.

As used herein, the term "sample" is used in its broadest sense, and may include a specimen or culture, of natural or synthetic origin.

As used herein, "protein" refers to a polymer of amino acids (whether or not naturally occurring) linked via peptide bonds. For the purposes of the present disclosure, a protein is the complete product, prior to any enzymatic digestion or fragmentation that is to be subjected to analysis by mass spectrometry.

A "peptide," as used herein, refers to one or more members of the mixture produced by controlled digestion of a protein. Typically, the peptide mixture is a product of digestion of the protein with a proteolytic enzyme, however other methods of controlled digestion are contemplated. It is preferred that the digestion mechanism cleave the protein at positions in response to the presence of specific amino acids. Due to incomplete digestion by the enzyme or other mechanism, the mixture of digestion products (i.e., peptides) can include the undigested protein, which in this situation would also be a peptide.

Finally, as used herein the term "fragment" or "peptide fragment" refers to the products of fragmentation within a mass spectrometer.

The invention described herein provides improved methods and systems for analyzing mass spectrometry data, especially to detect and identify molecular variants, wherein the initial sample contains a mixture of the molecule of interest (the reference molecule) and variant molecules, where the variants differ from the reference molecule by some chemical modification. The molecule of interest can be any molecule susceptible to analysis by mass spectroscopy, including but not limited to, polypeptides, oligonucleotides, lipids, organic polymers, pharmaceutical excipients and growth media components. A non-exclusive list of pharmaceutical excipients (polymers, surfactants, dispersants, solubilizers, bulking agents, etc.) includes, but is not limited to, polyvinylpyrrolidone, polyvinyl acetate, polysorbate, polyethylene glycol, polyvinyl alcohol, polyvinyl alcohol-polyethylene glycol, Poloxamer (polyethylene glycol-block-polypropylene glycol-block-polyethylene glycol), hydrogenate castor oils, and Mygliols. Cell growth media components include nutrients, such as protein, peptides, amino acids, and carbohydrates, as well as gelling components, such as agar, gelatin, carrageenans, alginates, and polyacrylamides. Exemplary modifications include oxidation, deoxidation, deamidation, conjugate, glycation, sulfation, glycosylation, alkylation, dealkylation, polymerization and the like. Preferably the methods and systems are useful for analyzing protein modifications, such as sequence substitutions, insertions or deletions, oxidation, deamination, glycosylation and the like.

The mass spectrometry data is acquired according to conventional methods, which typically consist of i) subjecting the sample to a separation technique, ii) acquiring an MS1 spectrum, iii) successively selecting each precursor ion observed with an intense signal on the MS1 spectrum, iv) successively fragmenting each precursor ion and acquiring its MS2 spectrum, v) interrogating databases through software (i.e., perform a computational search of observed spectra with respect to a database or a library of recorded spectra) to identify one or more molecules having a strong probability of matching the MS2 spectrum observed. In a preferred implementation, the sample is a protein that is first digested using a suitable enzyme to obtain a peptide mixture. Suitable enzymes include, but are not limited to trypsin, endoproteinase Asp-N, endoproteinase Glu-C, and thermolysin. If a protein sample contains wildtype protein and variant protein, the resulting peptide mixture will comprise wildtype peptide and variant peptide. Separation methods suitable for use in conjunction with the methods disclosed herein include, but are not limited to liquid chromatography (LC), gas chromatography, ion mobility, gel electrophoresis and capillary electrophoresis.

More than one type of digestion enzyme may be examined at once, and each may include multiple LC-MS/MS data acquisitions and multiple MS2 searches from any data acquisition. The MS2 data set may be generated using any fragmentation method, including any combination of low-energy CID, beam-type CID, and/or ETD. The quantification of a variant relative to wildtype (WT) is performed by label-free quantification with extracted ion chromatograms (XICs), which, in some implementations, have editable limits of integration.

Typically, the MS data is collected by a tandem mass spectrometer. In other implementations, the MS data is collected as MS1 data prior to fragmentation on a first mass spectrometer and MS2 data after fragmentation on a second mass spectrometer.

The data file(s) containing the MS1 and MS2 spectra can be loaded from a storage medium or received directly from another device (e.g., over a wired or wireless connection). The spectral data may be in any suitable format. In some implementations, the data is in a format proprietary to the manufacturer of the acquiring mass spectrometer, e.g., a .RAW file for a Thermo Fisher Scientific Orbitrap spectrometer. Alternatively, the data is stored or transferred in an open format, such as mzML. For implementations comparing variant and wildtype spectra, the wild type and variant data can be obtained from a single data file or from separate wildtype and variant data files.

The list of molecular identifications can be populated from results of a computational search of observed spectra with respect to a database or library of recorded spectra. Optionally, the system described herein will accept a file containing results of an MS2 search based upon the input MS data. The MS2 search can be performed by software such as Byonic, Mascot, SEQUEST, PEAKS DB, X!Tandem, and the like. Preferably, the search software is capable of identifying variants. For example, a very common search performed by the Mascot software, and that would be appropriate as input for the methods described herein, is the "Error-Tolerant Search". While the utility of the current versions of Sequest nor X!Tandem can be limited because these software packages allow any number of instances of each variant per peptide, these programs are appropriate when searches are limited to fewer than approximately 10 types of variants.

In addition to the spectral representations, the methods and systems described herein require a description of the reference molecule. In the case of a protein, the description would be an amino acid sequence for the protein of interest in the sample. One or more chemical formulae, amino acid sequences, and/or oligonucleotide sequences can be entered manually, loaded from a storage medium or received directly from another device (e.g. over wired or wireless connection). In a preferred implementation, the structure(s) and/or sequence(s) can be automatically loaded from a website, upon entry of a URL.

Figure 2:
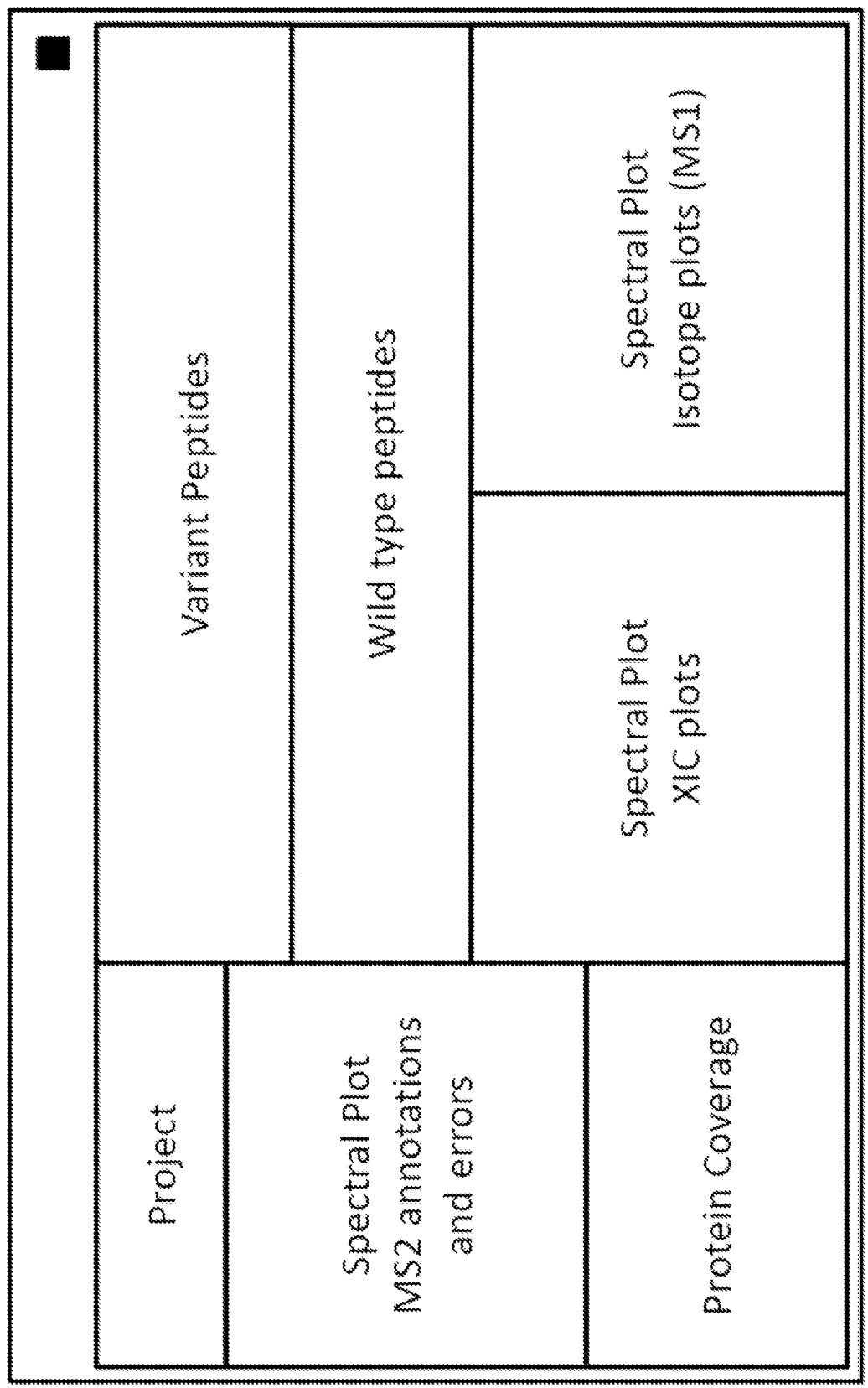
FIG. 2 provides a schematic diagram of the dashboard with four types of views.

The graphical user interface (GUI) or "dashboard" comprises several interactive views. FIGS. 1 and 2 provide example schematic layouts for the dashboard applicable to protein samples. Several spectral representations compose the Spectral Plots V1, optionally including key numerical data. The second view, the Peptide View V2, which is tabular in nature, provides molecular peptide identifications (molecular identifications). The Protein Coverage View or Summary View V3 graphically shows the identified amino acid residues (AAs) in the amino acid sequence filtered on modification type. The Project View V4 shows the data files under study and their characteristics.

The user can rearrange the sizes and even positions of the views to make their own personal layout. In many implementations, the views are dockable; that is, users can detach the view, which can be especially useful when two or more computer monitors are available, and re-attach or rearrange views. In some implementations, each of the views has a bar at the top with the name of the view and, optionally, a message "double click to dock/undock." Custom layouts can be saved and loaded as small files represented by the suffix .ini (or other appropriate suffix in non-Windows operating systems) and can be shared between individuals.

Figure 3A:
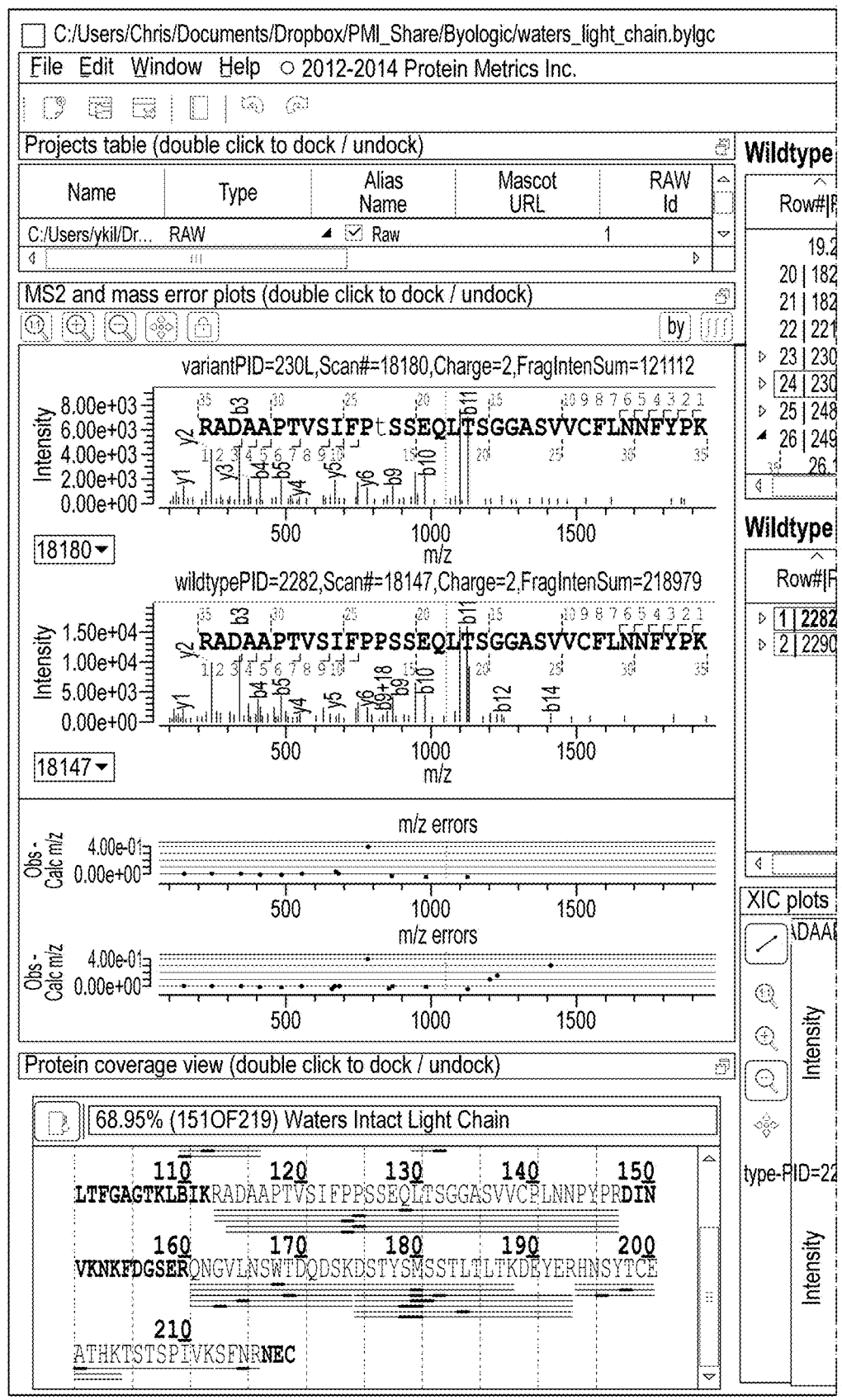
FIGS. 3A-3C illustrate a typical dashboard.
Figure 3B:
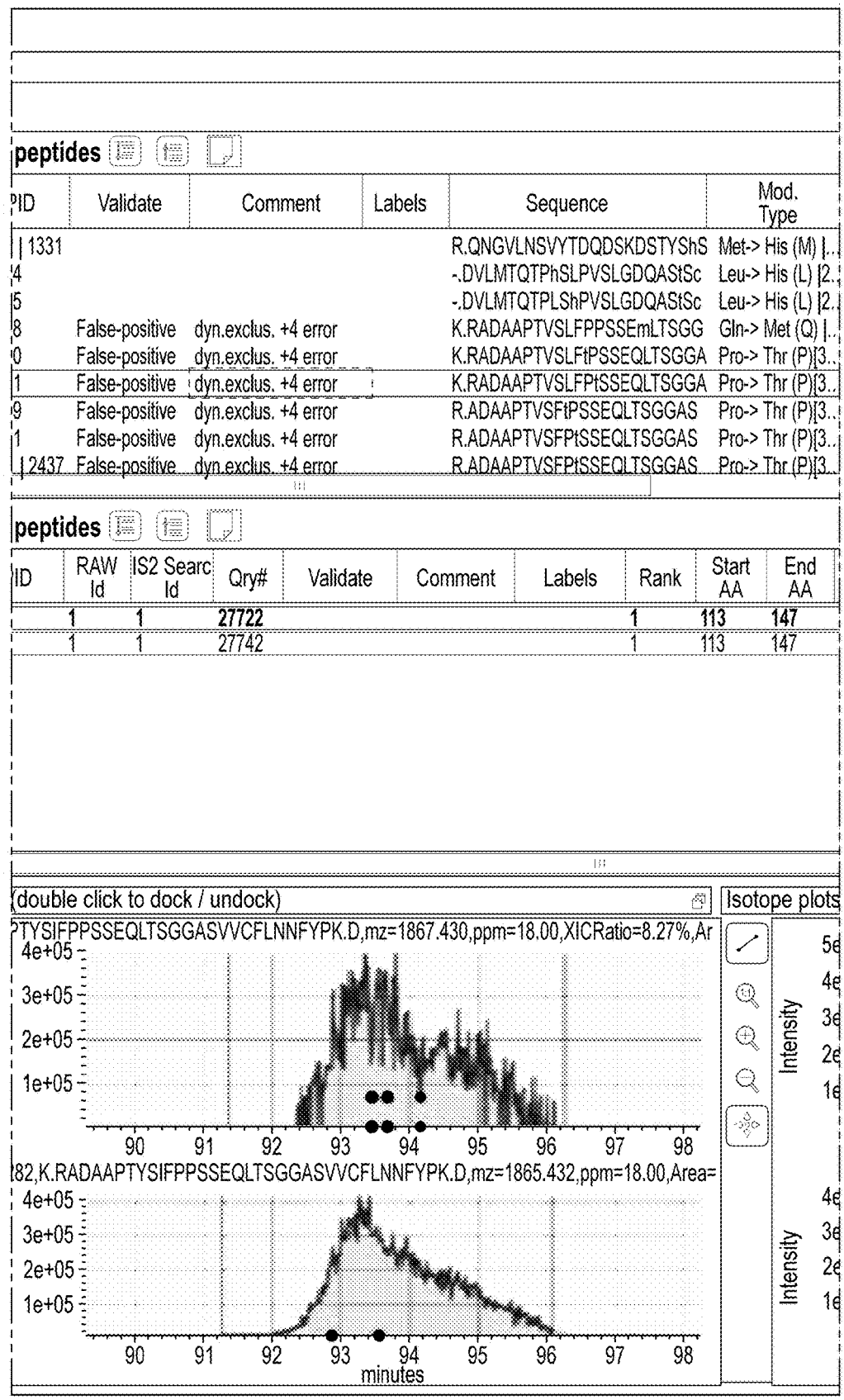
Figure 3C:
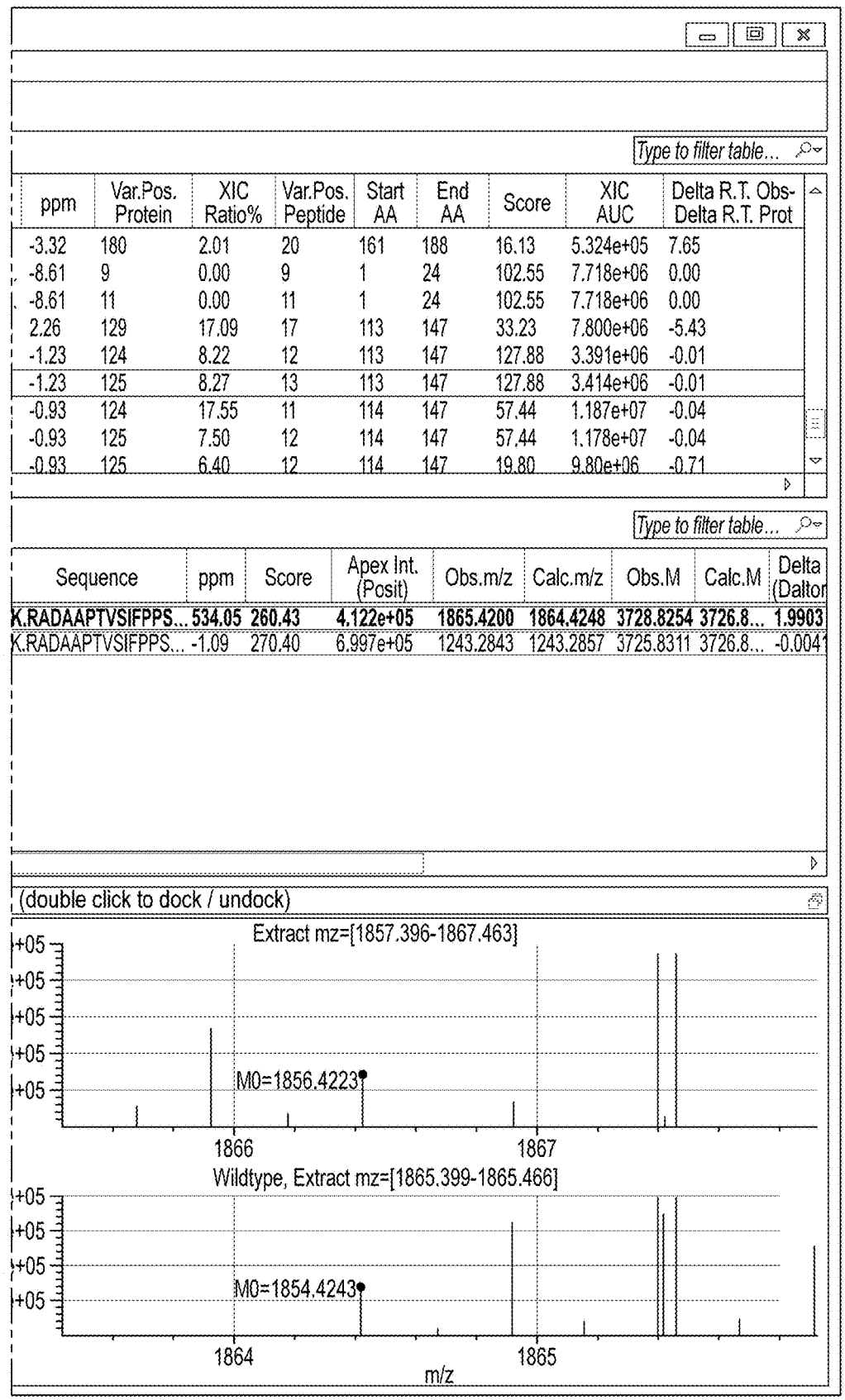

A screen shot of a typical dashboard layout is seen in FIGS. 3A-3C. The full dashboard shows spectral views (V1), peptide tables (V2), Protein Coverage (V3), and project view (V4). It is preferred that a common convention is defined for these views, e.g., where a plot or table relating to the variant or modified form is displayed directly above that for the "wildtype" (reference) form when one exists. Such a convention makes visual comparison of corresponding data easy for the user. All figures in the present disclosure have adopted this convention, i.e., variant above reference (wildtype).

The dashboard allows the user to customize the viewed information in a variety of ways. In a preferred implementation, the dashboard can simultaneously and interactively display an extracted mass chromatogram (XIC), an MS1 spectrum, and an MS2 spectrum based upon selection of a molecular identification by the user. In another preferred implementation the dashboard can simultaneously and interactively display paired spectra (XIC, MS1 and/or MS2) for a reference molecule and one or more variant molecules based upon a user selection of either a reference or variant molecule.

Preferably, the displayed spectra are selected from the group consisting of MS1 spectra, MS2 spectra and extracted ion chromatogram (XIC). When displaying paired spectra, preferably a variant spectrum is displayed immediately above, immediately below or immediately beside the reference spectrum. Alternatively, the variant and wildtype spectra can be displayed sharing a single horizontal axis with the two traces being differentiated by color or line type (bold, dotted, etc.). When sharing the same axis, two spectra can also be differentiated by showing one representation above the x-axis and the second mirrored (or butterflied) below the x-axis.

The spectral representations displayed on the dashboard comprise (a) precursor isotopic pattern (MS1 spectrum), and (b) associated MS2 spectrum. In a preferred implementation, the dashboard will display both MS1 and MS2 spectra for both variant and wildtype. Further, preferably, the MS2 spectra is annotated with associated fragment mass errors relative to the predicted values. In yet another implementation, the dashboard further comprises (c) mass-selected chromatograms (XICs, XIC plot) for both the variant and wildtype, if both forms are represented by MS1 and MS2 spectra. An XIC shows the amount of peptide (typically measured as ion current within a selected m/z range) as a function of chromatographic elution time.

A variety of controls permit the user to manage the spectral plot views. In a preferred implementation, the times of MS2 scans on the m/z of the XIC are indicated by dots or other marks on the XIC plots. The MS2 scan currently active, meaning the one displayed in the MS2 plot (or wildtype or variant), is indicated by a different mark or color. In a preferred implementation, the three different types of plot (MS1, MS2, and XIC) allow panning, zooming, and resetting the level of zoom. The paired plots (e.g., MS2 of wildtype and variant) may be locked together so that the operations of panning, zooming, and resetting apply to both simultaneously.

An MS1 spectrum shows ion intensity as a function of mass-to-charge ratio (m/z) of unfragmented peptide ions. For accurate quantitation, MS1 scans should be acquired often enough that each peptide is sampled multiple times during its elution; one MS1 scan every two seconds is sufficient for most chromatography methods. FIGS. 3A-3C illustrate MS1 data in profile mode, meaning that the spectrum includes m/z measurements with regular spacing and shows peak shapes. The alternative is centroided data, meaning that each peak is replaced by its apex. The methods and systems described herein can be used in conjunction with either profile or centroided MS1 data.

Mass spectrometry instrument software (e.g., XCalibur from Thermo Fisher Scientific) labels each MS2 scan with the perceived m/z of the precursor ion. Conventionally the precursor m/z is the m/z of the monoisotopic molecule (meaning no $^{13}C$ atoms or other minority isotopes), but the instrument software makes errors by labeling the MS2 scan with the m/z of a higher isotope, and these errors can give false variant identifications. A preferred implementation marks the MS2 precursor m/z on the MS1 plot, so that a skilled operator or an error-detection software module can detect errors and reject false variant identifications.

An extracted ion chromatogram (XIC) as explained below can be used to measure quantity by integrating ion intensity over an m/z range and a time range. The integration may be over one or more isotope peaks of the ion. In a preferred implementation, the system uses the most intense isotope peak for the wildtype and the corresponding isotope peak for the variant. The limits of integration over m/z are shown on the MS1 spectrum plot by vertical lines or other marks. The limits are set automatically by the system but can be adjusted manually by a skilled operator in case the automatically set limits do not capture the full peak or capture more peaks from two different ion species.

Figure 4:
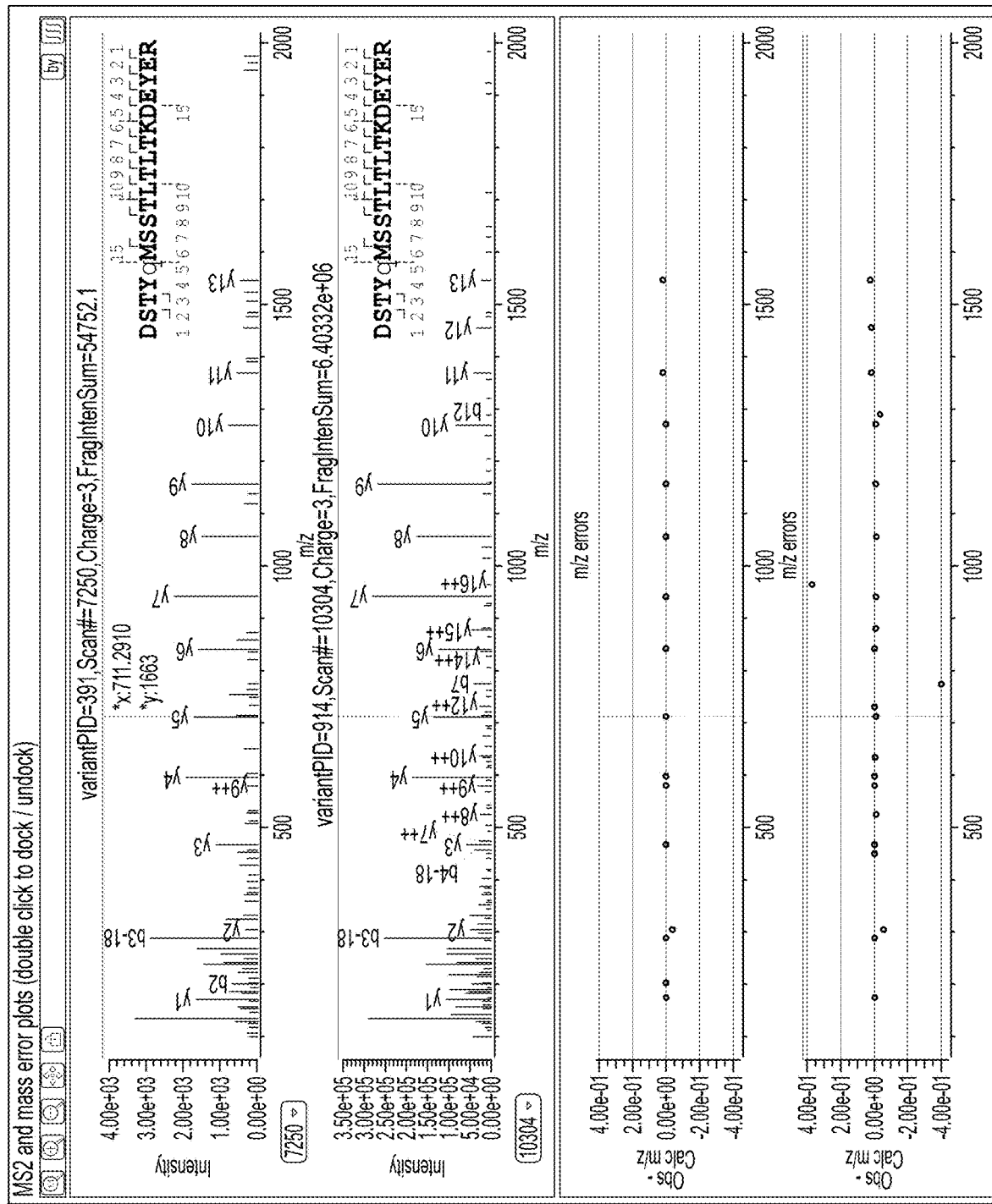
FIG. 4 provides one configuration of the MS2 spectral plot view. The top half shows an annotated MS2 spectra (variant on top, WT on bottom), and the bottom half shows the corresponding residual fragment m/z errors. When the cursor is placed over a peak, an asterisk appears with the exact mass-to-charge ratio (denoted m/z) and intensity displayed for that peak. Note the dotted line connecting the location of the mouse through all 4 plots.

The MS2 spectral plots for the variant and reference molecules are another important feature of the software system. In a preferred implementation, the peaks in these plots are annotated with the product ions (fragments such as b- and y-ions) with calculated m/z values matching the observed m/z values of the peaks. In addition, this plot can include the m/z errors for each fragment peak relative to its predicted m/z value (FIG. 4). A skilled operator can compare reference and variant MS2 spectra and thereby validate true variants and reject false positives. For example, for an amino acid substitution, only those product ions (such as b- or y-ions) containing the misincorporation will show a mass shift, and they should all show the same expected mass shift. A feature that aids comparison of aligned MS2 spectra is a cursor that is movable by the mouse (or other user interface device) and allows alignment of the different b/y (c/z) ions with a dotted line. In some implementations, when the cursor is positioned exactly over a fragment ion, the exact reported m/z and intensity is shown with an asterisk as seen in FIG. 4.

The mass errors should be similar for both MS2 spectra as well, otherwise misidentification is likely. It should be remembered however, that the variant molecule may be at low concentration and hence measured at lower signal-to-noise ratio and this may cause missing fragment ions or larger m/z errors.

In one implementation, the MS2 plots additionally display the amino acid sequence with b/y (c/z) ions mapped in the upper right to quickly show which fragment ions are observed. Preferably, the system will include label and fragment buttons capable of turning on/off these annotations.

In some implementations, the dashboard will also provide an extracted mass chromatogram (also known as an extracted ion chromatogram or "XIC"). There are various aspects to the XIC of a molecule that can help in distinguishing a true from false identification, or whether a variant identification is of sufficient abundance to be relevant. The XIC plot shows the intensity versus chromatography time for the variant (top) and reference (bottom) molecules and their areas in ion counts. When the methods and systems are used in conjunction with both variant and reference spectral representations it is preferred that the XIC plot shows a ratio of XIC areas for variant/reference at the top of the XIC plot. In some implementations, this ratio also is displayed in a data column in the Peptide View (molecule identification table).

Automatic setting of the time window for XIC integration can be made during project creation and those default time limits are visible as two vertical lines for each XIC. These lines can be dragged by the user's mouse to adjust the integration time for individual XICs if needed. The indicators marking the integration time limits are preferably two vertical lines, however other indicators, such as arrows or other marks, can also be used.

Variant and reference molecule elution times are important information for deciding the correctness of a variant identification. An unexpected difference between these elution times can be a sign of an incorrect variant identification. In a preferred implementation, the system predicts elution time shift of the putative variant relative to the reference based upon the chemical structure of the variant and reference molecules. In one implementation, elution time prediction for peptides can be based on the algorithm of Krokhin et al. (Mol. Cell. Proteomics, vol. 3, 908-919 (2004); PMID 15238601, incorporated herein by reference). The molecular identification table (as Peptide View), described in greater detail below, can include columns for observed and predicted elution times of the variant and reference molecules, but the column of the DeltaObserved-DeltaPredicted, that is, the difference of the two differences, is of most importance because this "Delta-delta" tends to minimize the effect of absolute prediction time errors and is a more stable statistic to use as evidence for an incorrect identification due to improbable elution times.

The molecular identifications can be provided in tabular form. In one implementation, a list of peptide identifications in tabular form (the Peptide View), wherein each line of the tabular form represents a single peptide from the list is shown. User selection of a molecular identification from the list can automatically display the XIC, MS1 spectrum and/or MS2 spectrum associated with the molecule. Preferably, selection of a molecule from the list will also automatically display spectra associated with corresponding molecules (reference or variant). The molecular identification table can be populated from results of a computational search of observed spectra with respect to a chemical database (e.g., a sequence database for peptides) or library of recorded spectra.

In some implementations, the molecular identifications can be split into two tables a reference molecule table and variant molecule table. Such an implementation can be particularly useful when analyzing protein variants based on mass spectra collected for an enzymatic digest of a protein preparation of interest. The Variant View provides information on the variant peptide identifications. The Wildtype Peptide View shows the wildtype identifications corresponding to a variant/modification identification. In some implementations, the peptide table is a table of "peptide-spectrum matches (PSMs)", in which peptide identifications are replicated with each peptide associated with a single scan. In another implementation, the peptide in the peptide table is matched to the highest-scoring scan. In this implementation, the peptide can be matched with all scans having a peak corresponding to the peptide sequence (and associated modifications) and optionally the user could drill down to see all scans.

In some implementations, a listed PSM is associated with an MS2 spectrum. A listed peptide is associated with a set of, more or less identical, MS2 spectra. The listed PSM is associated with a peak in an MS1 spectrum that triggered the MS2. This MS1 peak can appear in multiple MS1 scans. By selecting an MS1 peak over multiple scans, and presenting it as a function of time, one generates the XIC. Therefore, by associating the peptide with one or more MS2 spectra, the corresponding MS1 and XIC are also associated.

The data fields, their (customizable) organization, and associated plots are intended to provide the user with the information needed to efficiently make a validation decision and associated annotation for each of the putative variant identifications in the Variant View. There are various strategies and techniques to determine the proper validation status of each of the peptide entries, and these can be refined with experience, and of course depend on the case.

The tabular form can comprise a variety of data fields, for example, a field providing the modification state of each molecule or a field providing a validation status of each peptide identification. Examples of suitable modification states include, but are not limited to, unmodified (wildtype), amino acid substitution, amino acid insertion, amino acid deletion, oxidation, deamidation, and glycosylation. Examples of suitable validation statuses include, but are not limited to, true-positive, false-positive and uncertain. In other implementations, the assembly of peptide identifications is a graphical representation of the protein, wherein the graphical representation of the protein comprises an amino acid sequence for the protein and a plurality of markers mapped to the amino acid sequence and representing peptides within the protein, and further wherein the step of selecting a peptide comprises user selection of a marker.

For Variant View and Wildtype Peptide View, the user can also rearrange and sort columns as well as hide/show columns and adjust their widths for optimum viewing. In an exemplary implementation, this can be done by dragging column headers or right clicking on the heading to pop-up a Header Editor. Alternatively or additionally, a user can rearrange columns by dragging around the row positions, and show or hide specific columns. In a preferred implementation, the Header Editor tool tips are available by hovering the mouse over column headings and icons.

Peptide, or oligonucleotide, entries optionally may be grouped by sequence. In one implementation, this function can be accessed via a "Group By" command on the Menu bar. In Variant Peptide view, for multiple peptides to be grouped together, their identifications must have the same sequence including modification type and position. In Wildtype Peptide View, the wildtype peptides are grouped only if they have the same sequence, observed charge (z), and Raw file ID # (same LC-MS/MS run). In some implementations, above the tabular views, there can be buttons with down (ungroup) and up (group) arrows which cause the display to show or not show multiple occurrences of a given sequence.

The principal action of the user, after examination of the relevant data, is to apply to each putative variant molecule identification a Validation class. In a preferred implementation, the possible options are presented to the user via a drop down menu in a Validate column in the molecular identification table. In one implementation, the choices are True-positive, False-positive, and Uncertain. These values can be changed by the user, so for example, Uncertain might be chosen while the study continues.

In some implementations, the user can also enter written Comments in a field accepting free text. The Comment field can be edited by typing directly into the Comment cell of the Peptide View table or by double-clicking on the cell to open a pop-up box for typing.

The Variant View and Wildtype Peptide View tables can each be filtered, for example using a text box on the upper right hand side of that view. For example, to find all peptides containing a certain amino acid sequence, one can simply filter for peptides containing a specified string of letters. Or if a particular m/z is of interest, one can simply type a number representing that m/z.

In some cases, filters based on characteristics of the putatively identified peptide via MS2 data can be applied. For example, a minimum matching score such as a Mascot Ions score of at least 30, can be chosen. In another implementation, specific to analyses using Mascot search results, a filter based on Minimum alt_rank_score/primary_rank_score can be used. Maximum m/z errors can be used. Often an initial search will include a maximum m/z error, but this secondary filter provides an opportunity to further shrink the acceptable error, if desired. A maximum retention time deviation relative to the wildtype (minutes) can be entered; a large number means the user wishes no filtering of the input data on that basis, although one may still use that information in judging whether the identification is a false or true positive. A minimum XIC ratio (variant/modified form relative to the wildtype) can be set to, for example, 1%, 0.2%, or 0% (no filter). A minimum modification mass shift may be set, for example, setting to 2 will filter out deamidations.

A filter can also be based upon data type associated with each molecule within the table. For example, molecular identifications can be assigned a validation class, such as true-positive, false-positive, uncertain or unassigned. Molecular identifications can also be assigned a modification class. The modification class can specify an amino acid substitution, e.g. Leu→His, or a chemical modification, such as oxidation or deamidation. When applying a peptide type filer, the results can be filtered by a specific class, e.g., oxidation, or by a group of classes, e.g., any amino acid substitution (such as Leu→His or Pro→Thr). In other implementations, the filter can perform a string search on the modification class. For example, one can filter on the search string "oxidation" and select peptides having oxidation or dioxidation as the modification class. Preferably, filter settings can be saved and reloaded for convenience.

The Protein Coverage View is a graphical representation of a protein of interest. For example, the graphical representation of the protein can comprise an amino acid sequence for the protein and a plurality of markers mapped to the amino acid sequence and representing peptides within the protein, and further wherein user selection of a marker automatically displays the XIC, MS1 spectrum and MS2 spectrum associated with the peptide represented by the marker. The peptide mapped to the amino acid sequence can be modified relative to the amino acid sequence, and the modification would be graphically depicted on the marker for the peptide. A similar graphical view is contemplated for other polymeric molecules, e.g., for an oligonucleotide, wherein the amino acid sequence is replaced with a nucleotide sequence.

Figure 5:
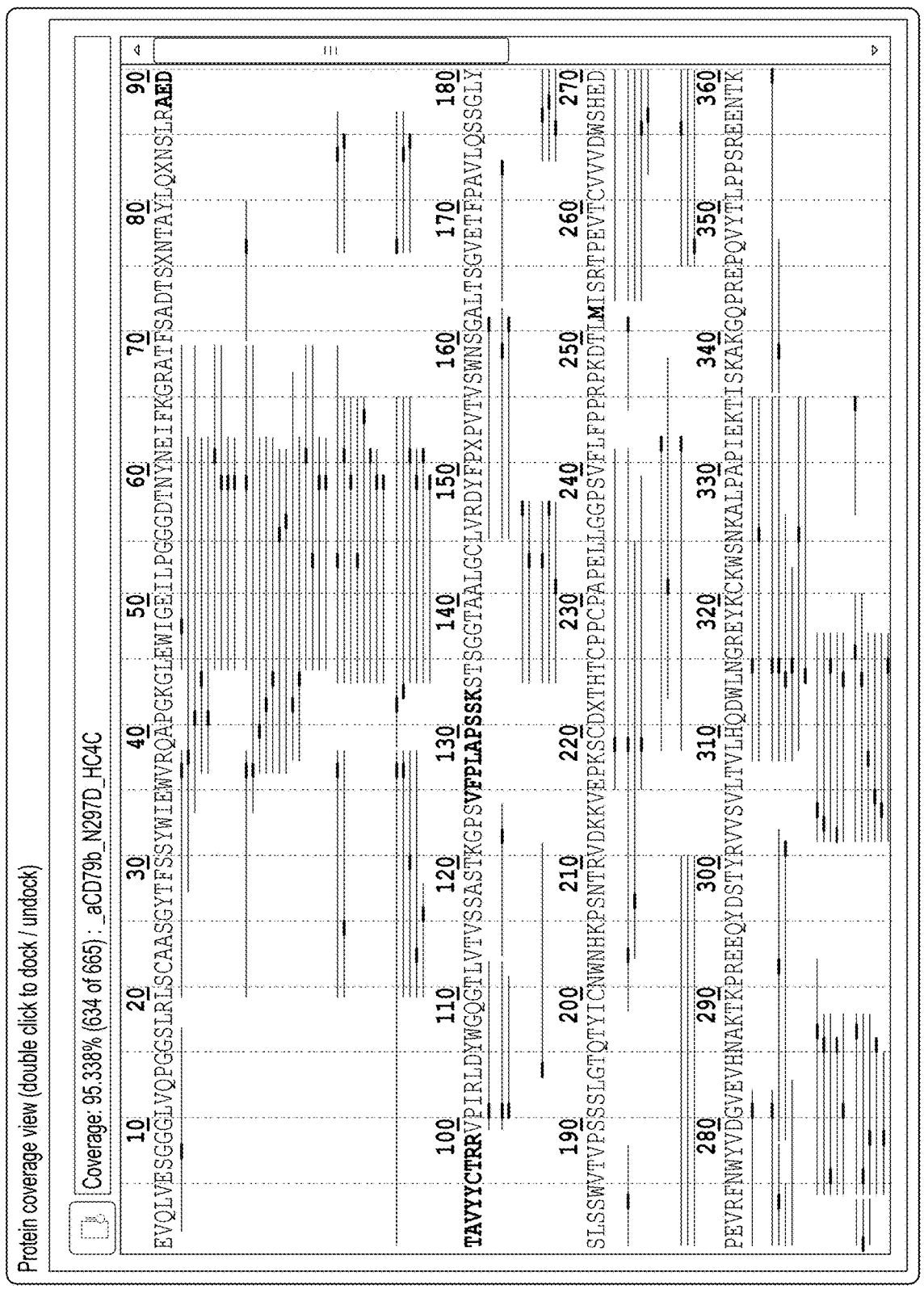
FIG. 5 provides one configuration of the Protein Coverage View, showing the sequence coverage of the putative identifications for the filtered variant/modification type(s). Variant positions within the peptides are highlighted. Results from different digestion enzymes are in different colors, and for a given digestion enzyme different LC-MS runs are separated by a space.

FIG. 5 shows an example of a Protein Coverage View. This exemplary Protein Coverage view shows the sequence coverage of putative peptide identifications. The positions of variants (sequence modification, oxidation, and the like) are highlighted, typically with a contrasting color. In situations where MS data from more than one enzyme digestion is input, the Protein Coverage view will visually distinguish between digestion patterns, typically using distinct colors, but may also distinguish by pattern, depth of color and the like.

In FIG. 5, results from two different digestion enzymes, thermolysin (blue bars) and trypsin (red bars), are illustrated. Variant locations are also indicated by the highlighted AA positions in the bars. Clicking on a bar selects a peptide identification in either the Variant Peptide View or the Wildtype Peptide View and changes the MS1 and MS2 plots accordingly. Conversely, clicking on a listing in one of the Peptide Views changes the highlighted bar and the MS1 and MS2 plots. As with other views described herein, the Protein Coverage View can be undocked from the contiguous dashboard and be moved to cover some part of the rest of the GUI or dragged to a second computer monitor.

In the Protein Coverage view, peptide identification entries optionally may be grouped by sequence. This function can be accessed via a "Group By" command on the Menu bar. In the Protein Coverage View, grouping is based on the same sequence, modification type and position, and Raw ID #.

Finally, the dashboard can comprise a Project View, which provides the user with information relating to source files, export files, and user preference files. Preferably, the Project View identifies the source files in a tabular format. The fields of the tabular format include, but are not limited to, one or more of the following: file name, file type, source URL, Raw ID#, type of preprocessing (e.g., digestion with trypsin or thermolysin), type of search (e.g., fully tryptic or semi-tryptic), search engine (e.g., Mascot or Byonic), and so forth. The user can rearrange and sort columns as well as hide/show columns and adjust their widths for optimum viewing. This can be done by dragging column headers or right clicking on the heading to pop-up a Header Editor. The user can rearrange columns by dragging around the row positions, and show or hide specific columns.

As mentioned above, selecting a peptide identification bar in the Protein Coverage View also makes a selection in the Peptide View, and vice versa. Selecting a variant peptide, either as a bar in the Protein Coverage View or as a listing in the Variant Peptide View, automatically populates the Wildtype Peptide View. Selection of a peptide, variant or wildtype, either as a bar or a listing, automatically populates the XIC plots. Zooming or panning within the variant spectrum plot can be optionally linked with the same actions in the wildtype spectrum plot, and vice versa.

In some implementations, a table within the dashboard will include an Export data button with a spreadsheet icon which enables exporting of a file, preferably a delimited text-based file. A delimited text-based file is any type of text-based file that establishes delimiters between a series of data, such as spreadsheet files, comma-separated value (CSV) text files, tabular text files, and the like. It should be noted that a text-based file can be either a text file or binary file that represents delimited text, such as some spreadsheet files. The export data button can be associated with any tabular view, but most preferably is associated with a Peptide View table. Clicking on the Export data button typically will open a dialog box allowing some choices for the exported table. For example, clicking on the ". . ." button will allow the user to browse to the desired save location and also allow file naming. This is a useful function for making reports and sharing data. The exported table will have the columns and their orderings as in currently active table and thus provides a flexible and customizable table to export.

The spectral plots may be exported as image files for assisting in report generation. In one implementation, the user can right-click from within the plot area to see an "export image" function which if clicked will open a dialog box. From this box the user can change a variety of parameters, such as x, y ranges, aspect ratio and figure overall size, as well as save the image in .pdf, ps. or .png formats. The plot may be zoomed-in as desired.

Alternatively, results can be exported via a pull down command under File on the Menu bar of the dashboard. Depending upon the active view at the time of exportation, the file format can be a text, HTML, spreadsheet, tabular, or image file. For example, peptide tables can be exported in .html or .csv format. Spectral data is preferably exported as image files, such as .png, .ps or .pdf formats.

The subject matter described herein for visual analysis of mass spectrometry data may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a computer program product comprising computer executable instructions embodied in a non-transitory tangible computer readable medium.

Exemplary computer readable media suitable for implementing the subject matter described herein include disk memory devices, chip memory devices, programmable logic devices, and application specific integrated circuits. In addition, a computer program product that implements the subject matter described herein may be located on a single device or computing platform or may be distributed across multiple devices or computing platforms.

Reporting of the results of the analyses may be performed in numerous alternative ways-for instance via a visual display terminal, a paper printout, or, indirectly, by outputting the parameter information to a database on a storage medium for later retrieval by a user, or by a combination of these reporting methods. The reporting step may include reporting either textual or graphical information, or both.

EXAMPLES

A controlled mixture of two human monoclonal antibodies (designated mAb1 and mAb2), was prepared with mAb2 at 1%. The controlled mixture was used as the sample for a 3-hour LC-MS/MS run on Thermo Orbitrap Elite to generate, Orbitrap MS1, CID fragmentation, ion-trap MS2. Several MS2 searches were performed utilizing Byonic (Protein Metrics, Belmont, CA, USA), including searches for the most common amino acid substitutions at most one per peptide, any amino acid substitution at most one per peptide, combinations of substitutions and modifications, and a wild card search (any mass delta within +/− 210 Da).

Figure 6B:
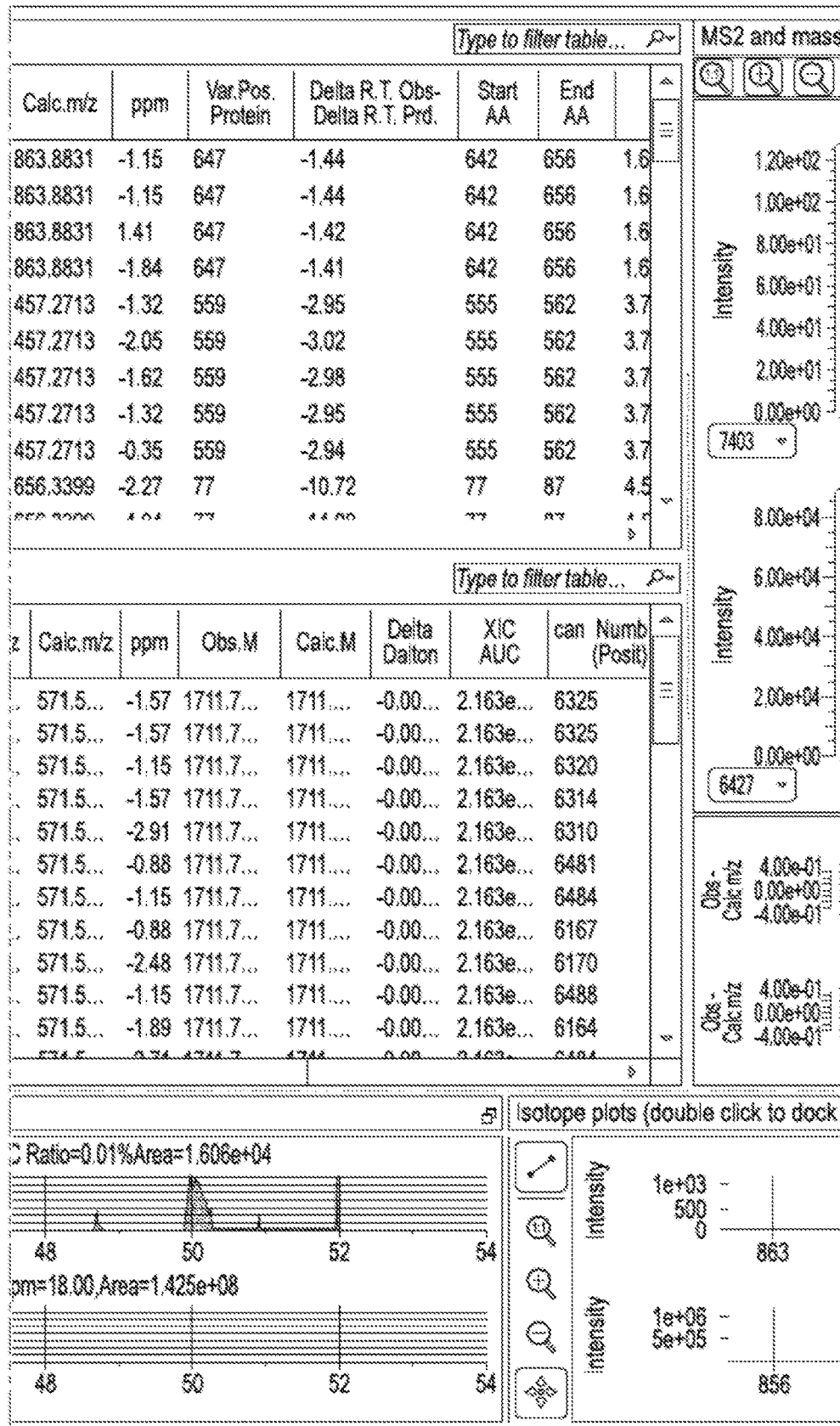
Figure 6C:
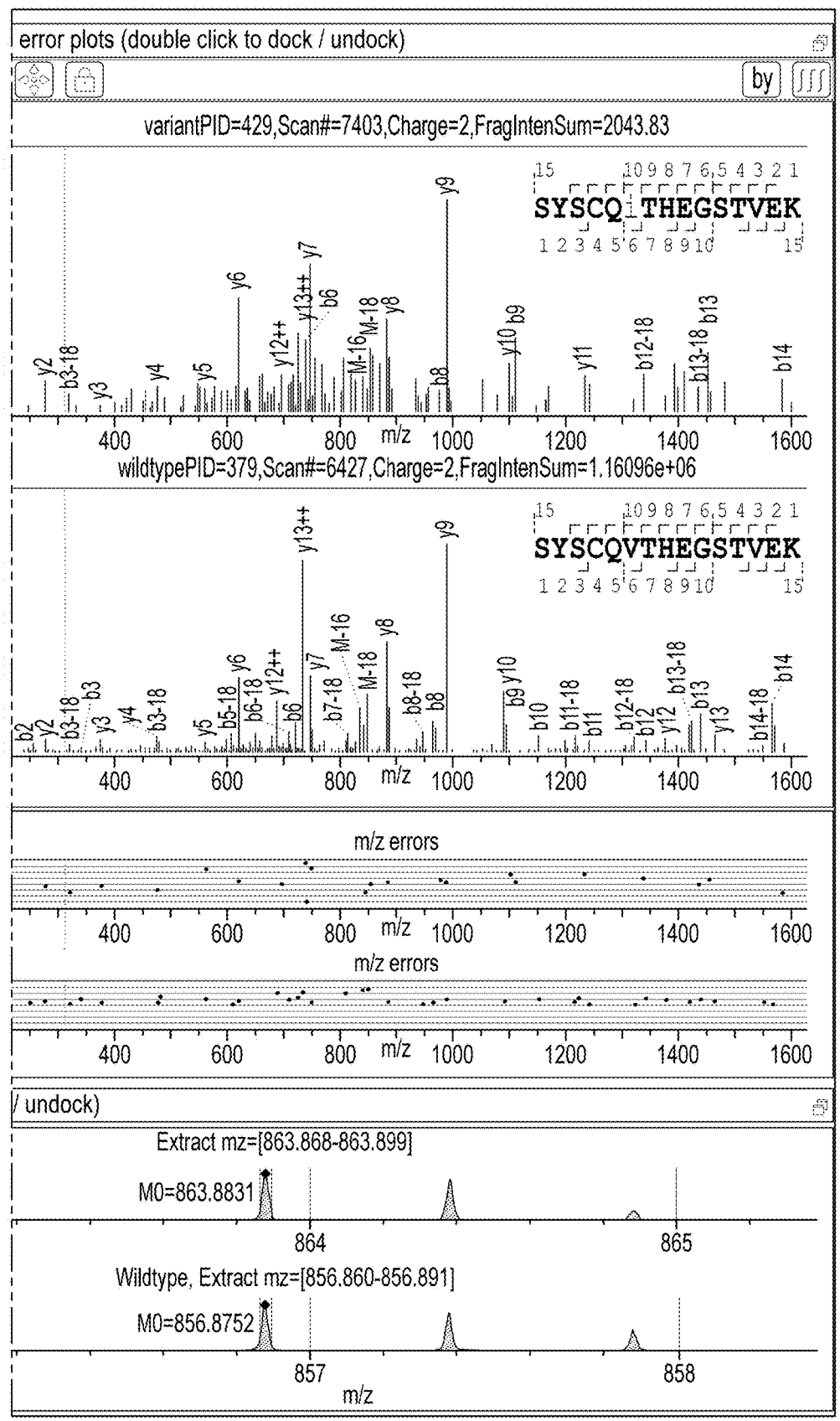
Figure 7:
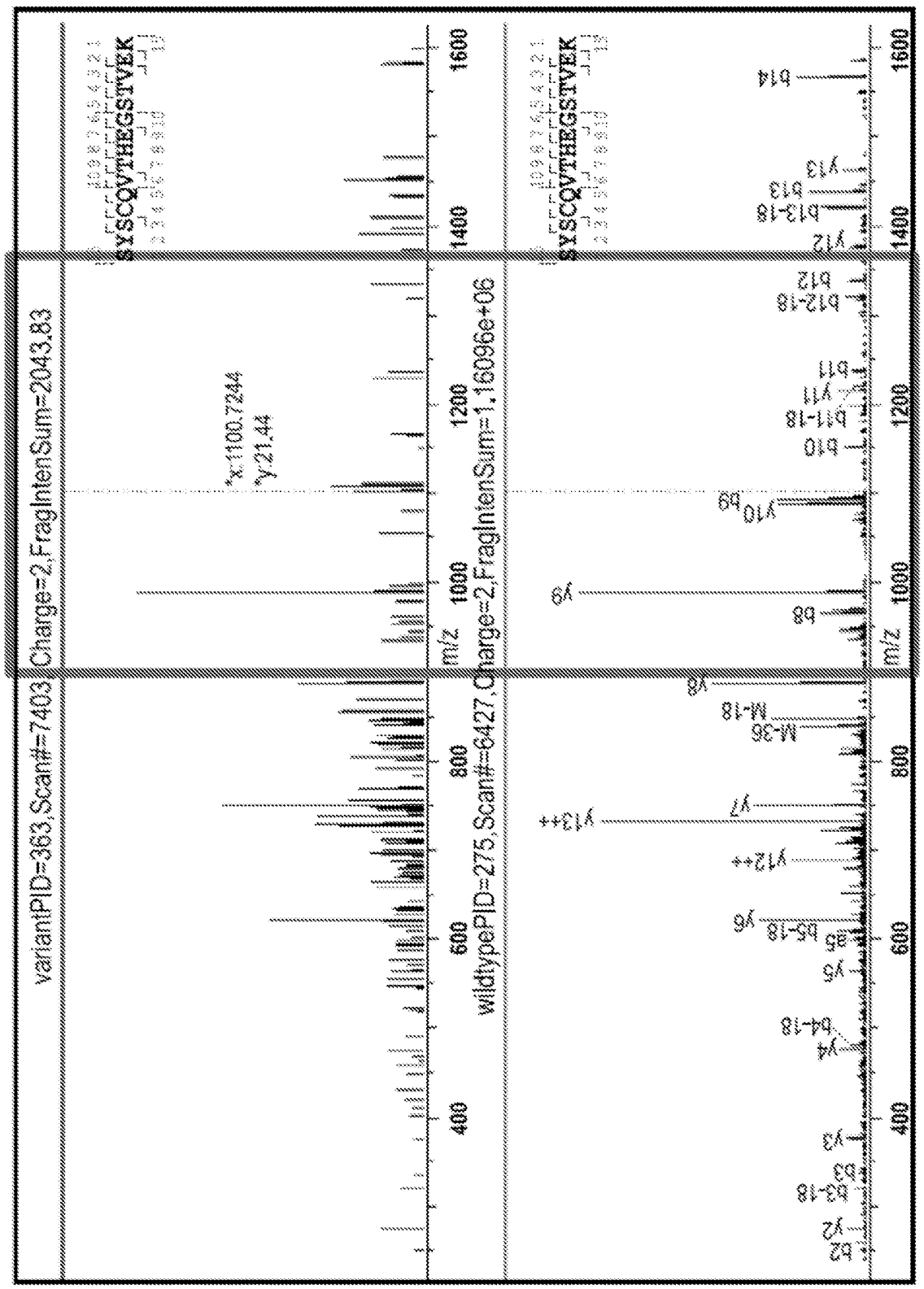
FIG. 7 provides an unzoomed view of an MS2 spectra for wild type and variant.
Figure 8:
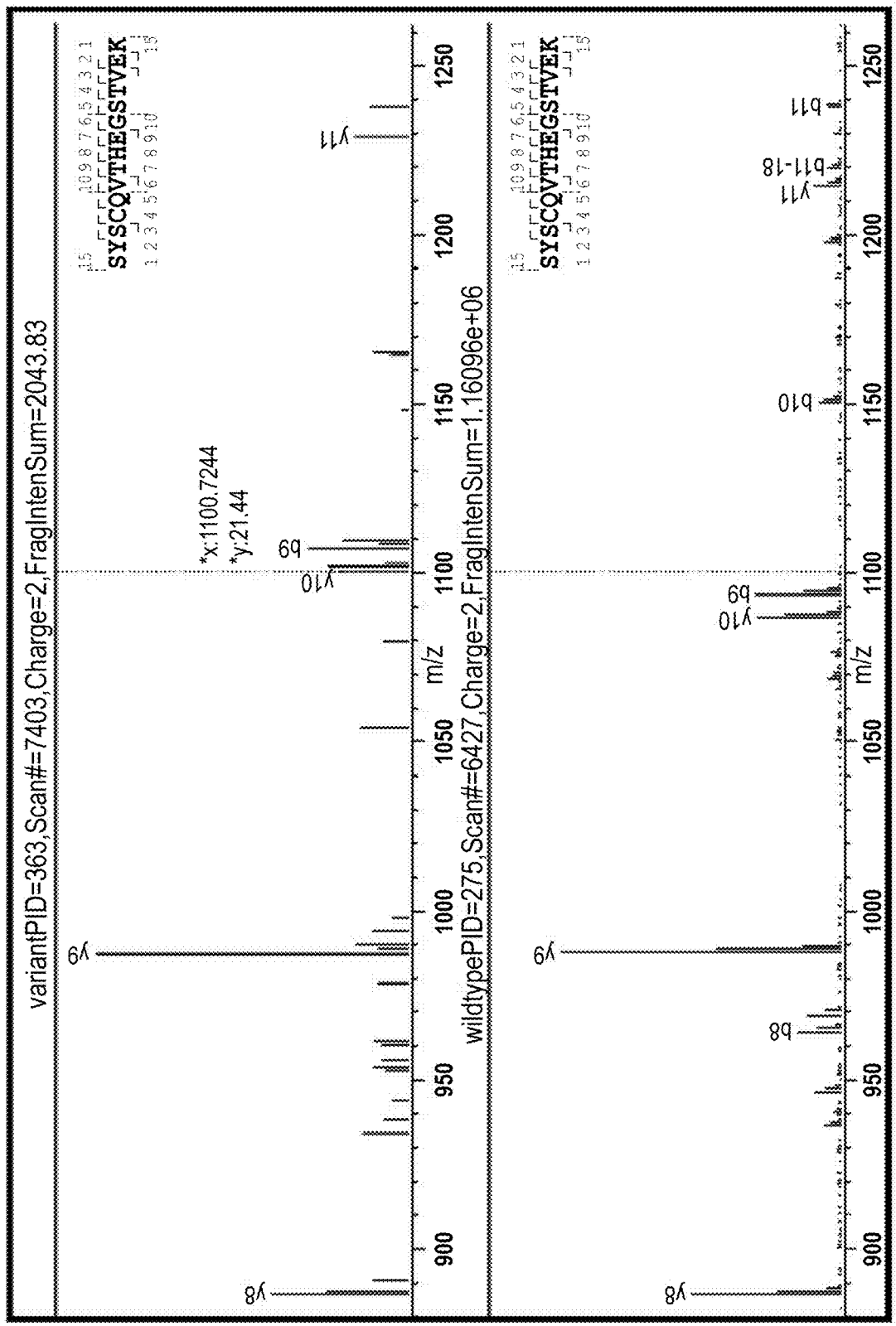
FIG. 8 zooms in on flanking peaks, which correspond to the boxed portion of the spectra in FIG. 7.
Figure 9:
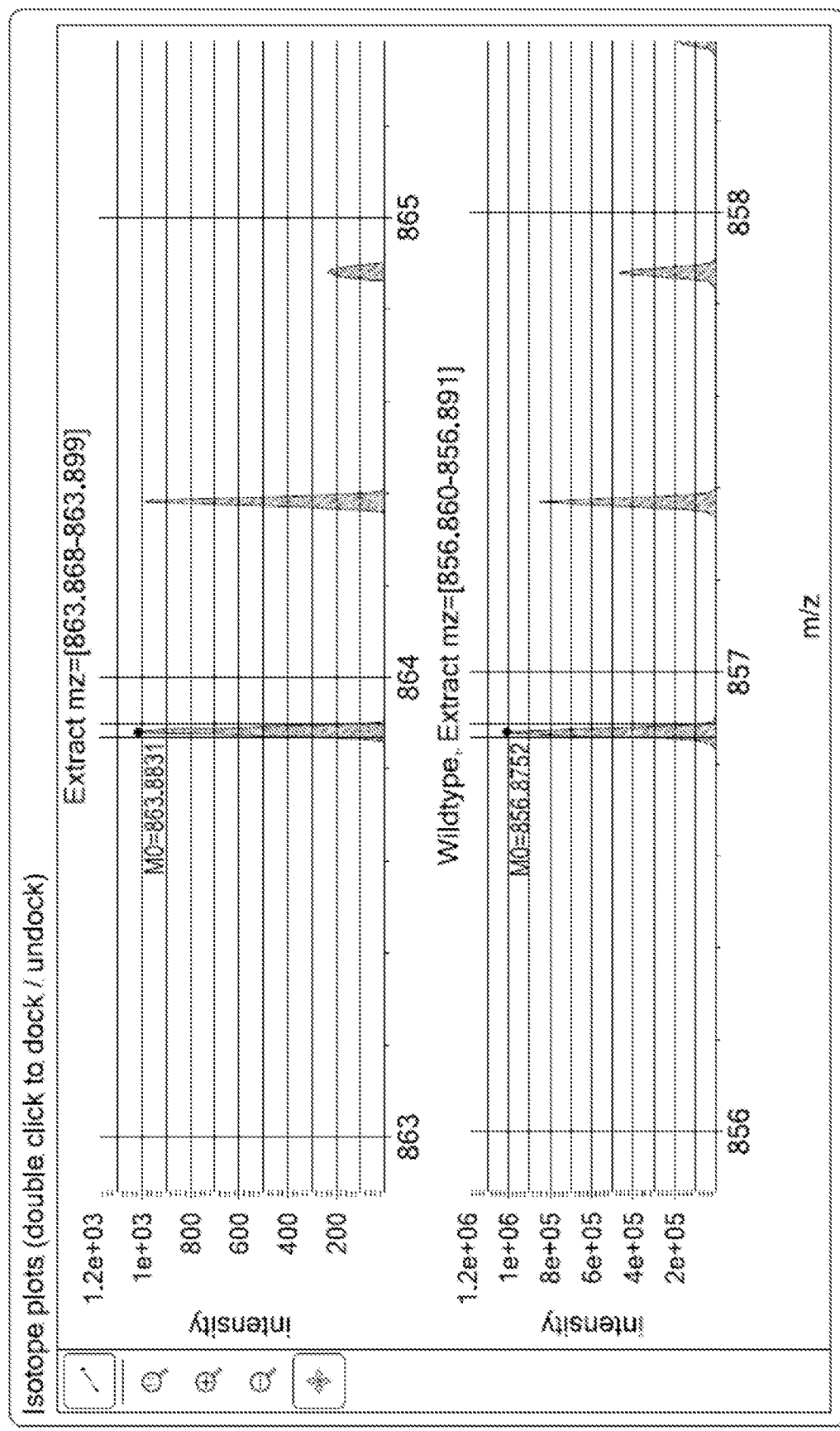
FIG. 9 provides an MS1 spectral plot view zoomed to a peak identified with a specific peptide.

Valine to isoleucine or leucine is a common substitution. FIG. 6 illustrates the dashboard (showing MS2, MS1 and XIC spectra, and Variant Peptide View, Wildtype Peptide View), with a peptide having a putative Val→Ile substitution highlighted. FIG. 7 provides an unzoomed view of the MS2 spectra for wild type and variant. FIG. 8 zooms in on flanking peaks to localize a +14.016 mass delta. The y10 (and greater) peak was shifted, while the y9 (and lower) peak was not. After identifying the putative variant, the MS1 isoptopic plot is (FIG. 9) was consulted to confirm that the monoisotopic mass corresponded to the putative variant. Finally, the XIC plot was used to confirm the putative identification and quantify the amount of variant.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

Interactive Selection and Display of Masses and Peaks

FIGS. 10A(1)-10A(3), FIGS. 11A-11C, FIGS. 12A-12C, and FIG. 13 illustrate methods and user interfaces (including non-transitory machine-readable medium that stores instructions to perform these methods) for interactively and concurrently showing the correlations between user-selected masses and/or peaks across different alternative spectral displays, such as mass, mass/charge (e.g., MS1, MS2, XIC, deconvolved mass spectrum, etc.). This correspondence may be shown by markers (e.g., colored markers, such as colored dots) that are shown directly on the data in each of these mass spectrum displays. Multiple point (masses) may be shown simultaneously.

Figure 10B:
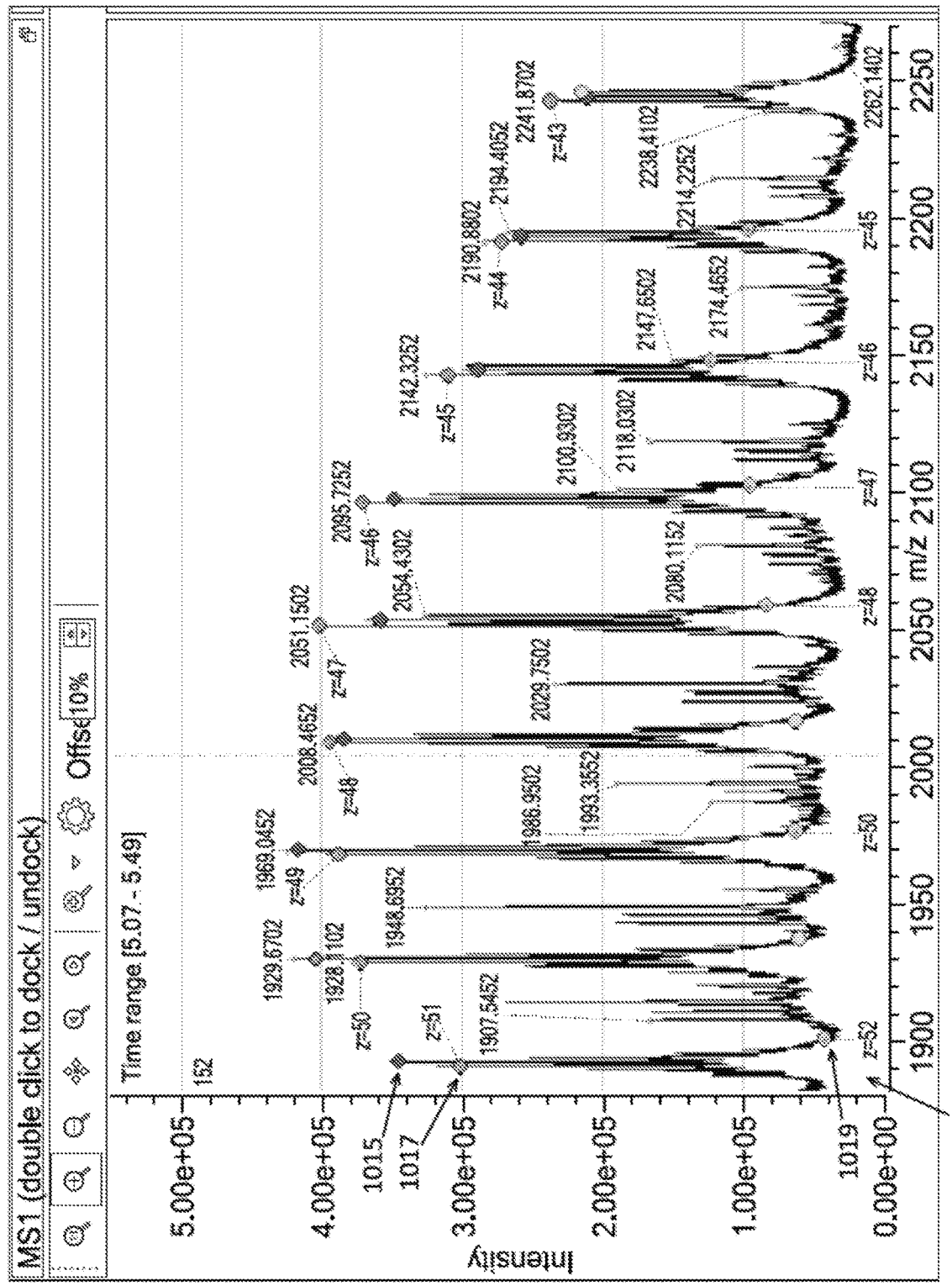
FIG. 10B shows an enlarged view of the labeled MS1 window of FIGS. 10A(1)-10A(3).

For example, FIGS. 10A(1)-10A(3) shows an example of a dashboard showing multiple windows, including a mass listing 1001, a chromatogram 1003, an MS1 plot 1005 and a deconvolved mass spectrum 1007. In the example shown in FIGS. 10A(1)-10A(3), three masses (two are visible in the mass listing 1001) have been selected. Peaks representing each of these masses (e.g., Mass ID 80 and mass ID 88) are then plotted on both the MS1 and deconvolved mass spectrum windows/plots. In the MS1 window, each mass selected results in a series of 'peaks' or values that are graphed onto the data shown. As shown in greater detail in FIG. 10B, the first series 1015 is represented by blue dots that correspond to a subset of peaks in the m/z plot. Similarly, the second series 1017 (shown by orange dots) corresponds to a second set of peaks. Finally, the third series 1019 does not consistently appear to correspond to a peak, and is likely to be erroneous. This may correspond to an "off by one" error in the resulting charge.

In FIGS. 10A(1)-10A(3), a thirty second portion of the chromatogram has also been selected, and the colored dots representing predicted peak positions using those masses are shown on the MS1 and also on the deconvolved mass spectrum windows. By interactively displaying this information in the windows as shown, a user may more easily interpret the spectroscopic data and distinguish actual signal from the noise. This analysis may be captured, saved, and/or transmitted, including for storing or transmitting as part of a report. Although the method illustrated above in reference to FIGS. 10A(1)-10A(3) refers to selecting a mass from the mass window/listing, alternatively or additionally a point (e.g., corresponding to the peak) may be selected from the MS1 window 1005, or the deconvolved mass spectrum window 1007. The corresponding mass may then be highlighted in the mass window 1001. Any of these windows may be manually or automatically rescaled, and this rescaling propagated across the other windows/spectral information.

Figure 11A:
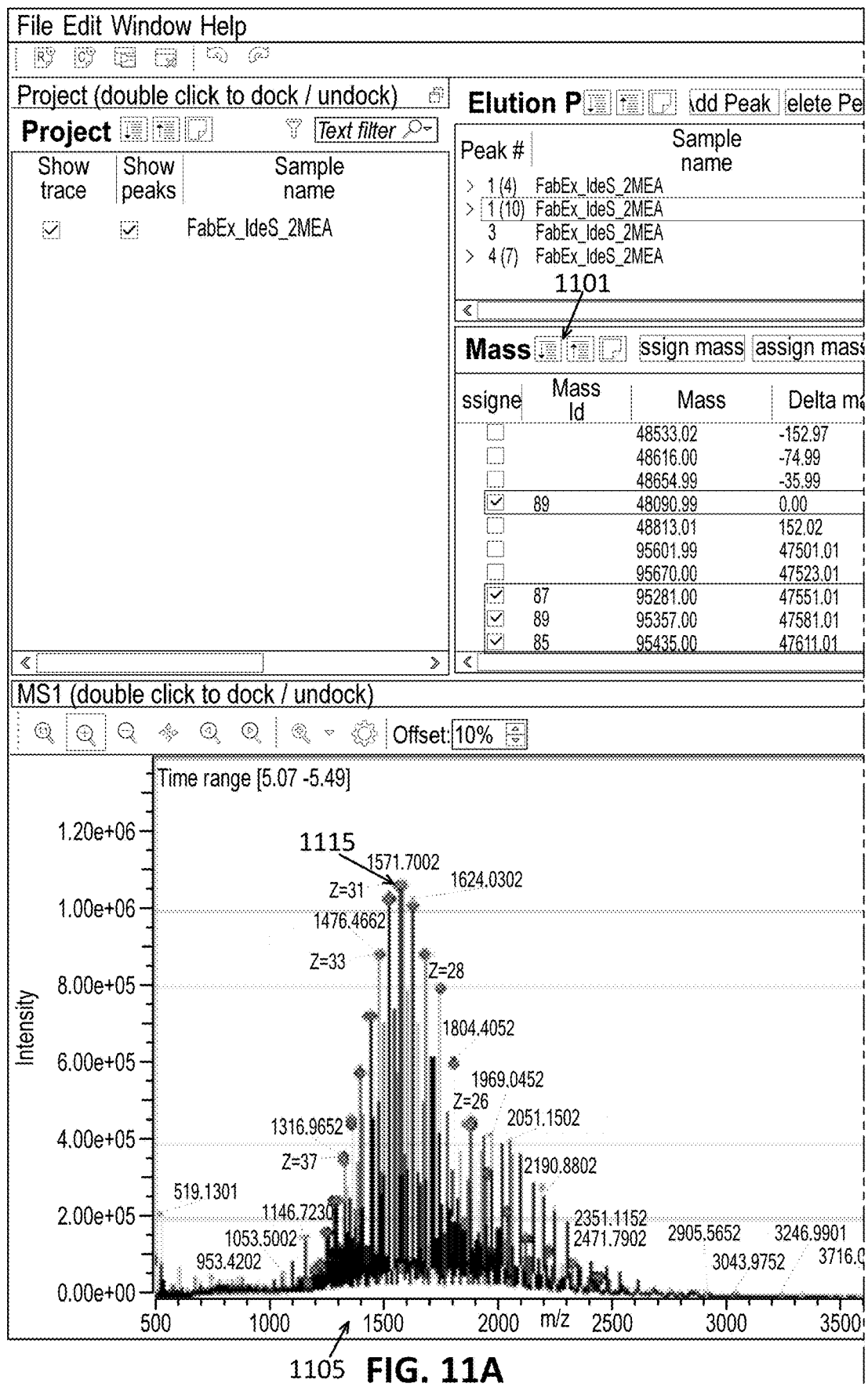
FIGS. 11A-11C is another example, similar to FIGS. 10A(1)-10A(3), showing a single selected mass, interactively shown on both the MS1 and deconvolved mass spectrum windows.
Figure 11B:
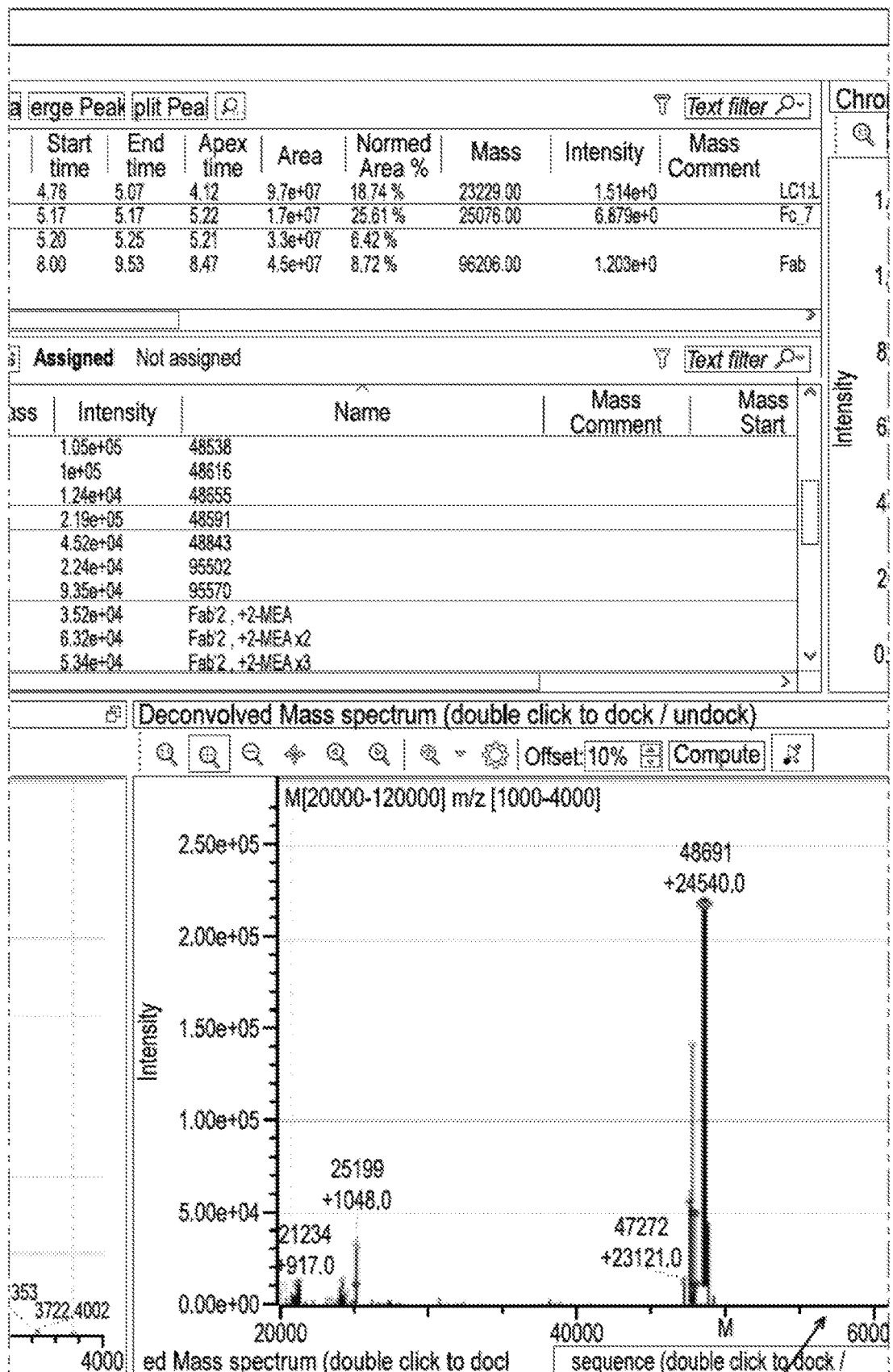
Figure 11C:
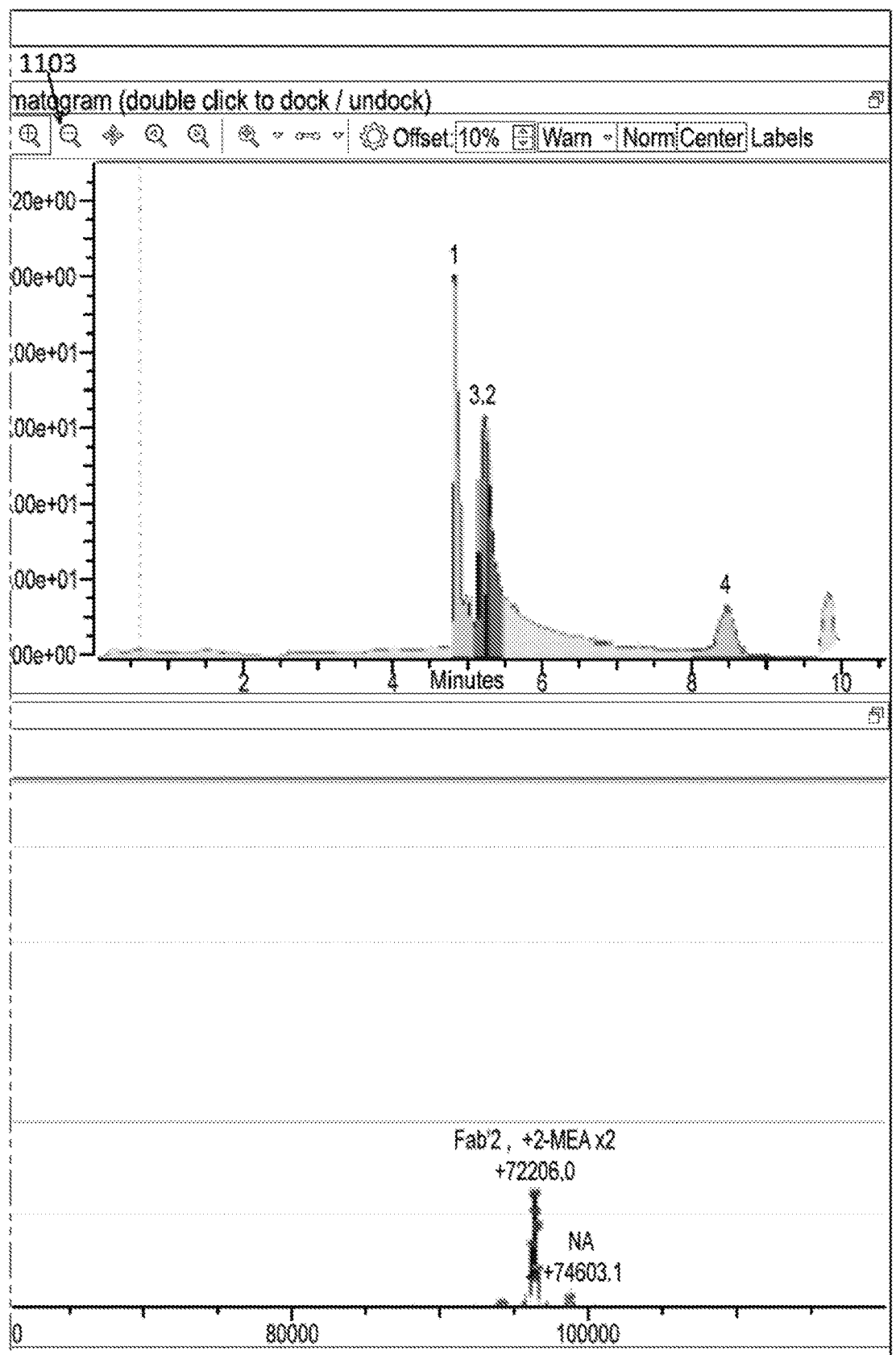

FIGS. 11A-11C show another example, similar to that shown above in FIGS. 10A(1)-10A(3), but including only a single selected mass, shown in the peaks of the MS1 window 1105 as a series of orange dots 1115. The corresponding mass is highlighted in the mass window 1101 and the deconvolved mass spectrum 1107. A chromatogram 1103 is also shown.

Figure 12A:
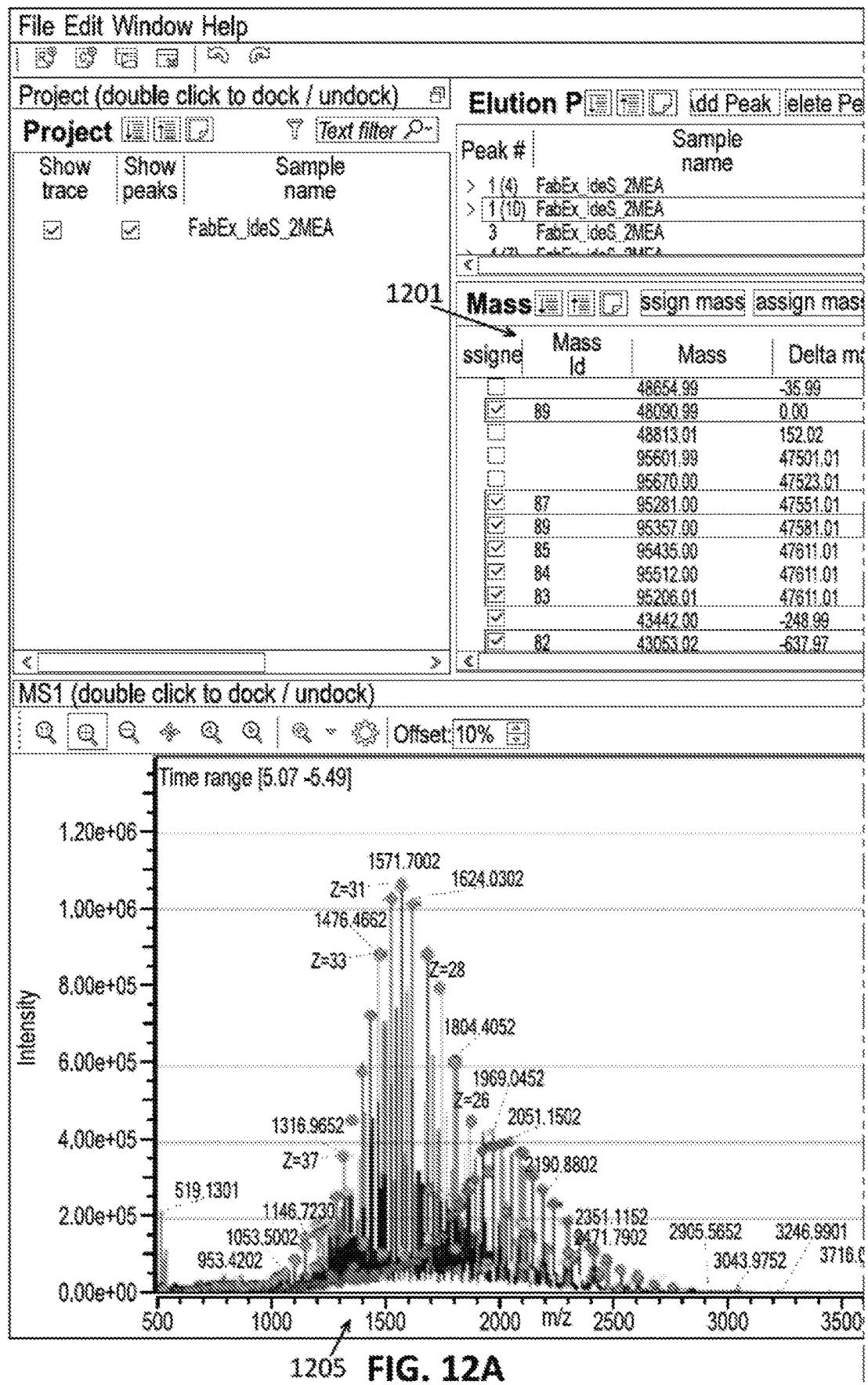
FIGS. 12A-12C is another example, similar to FIGS. 10A(1)-10A(3), showing four selected masses, each indicated by a characteristic color "dot". The mass may be selected from the mass table, or a graph (e.g., any of the windows shown) and the selected mass indicated in all of the windows, in real time.
Figure 12B:
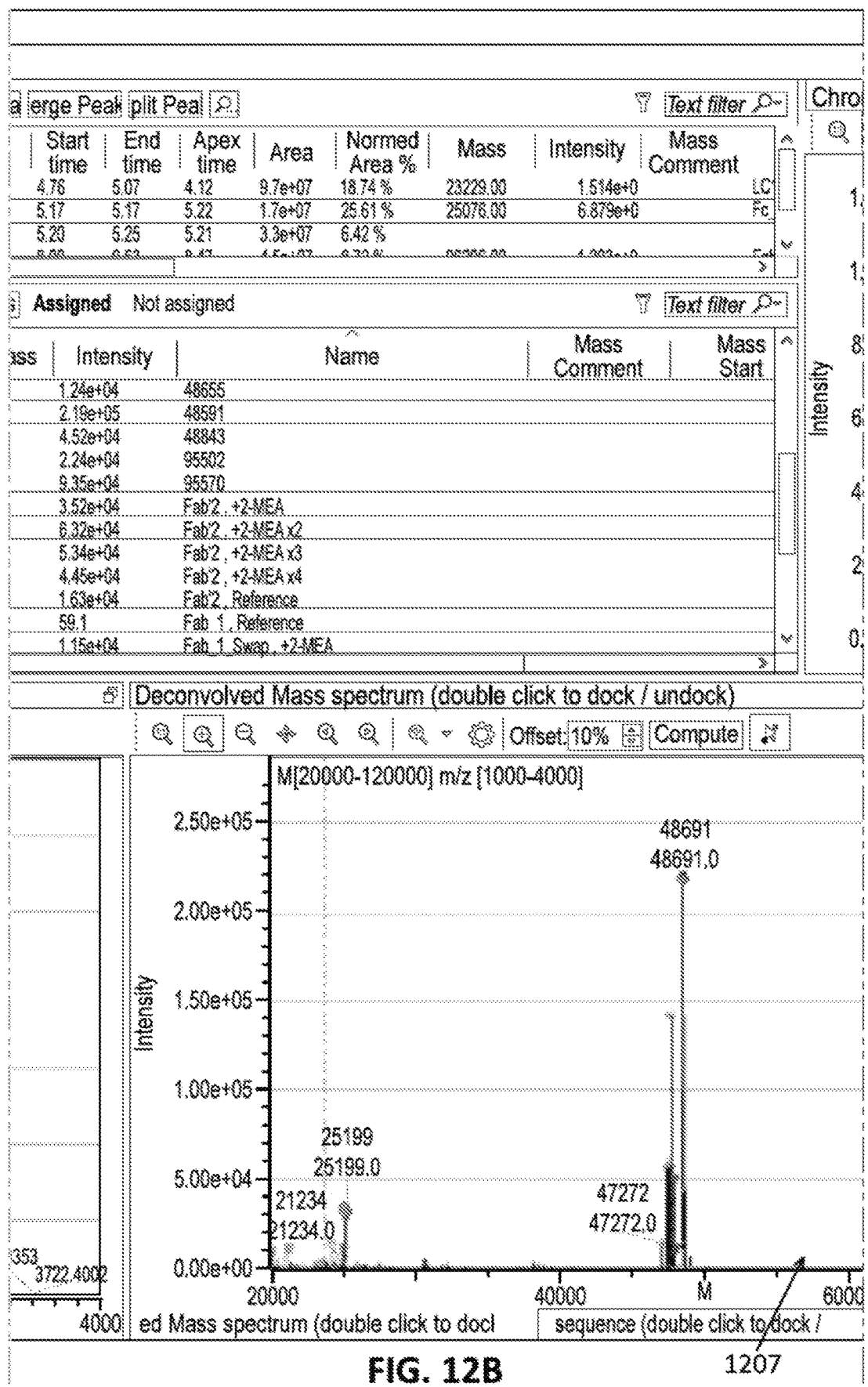
Figure 12C:
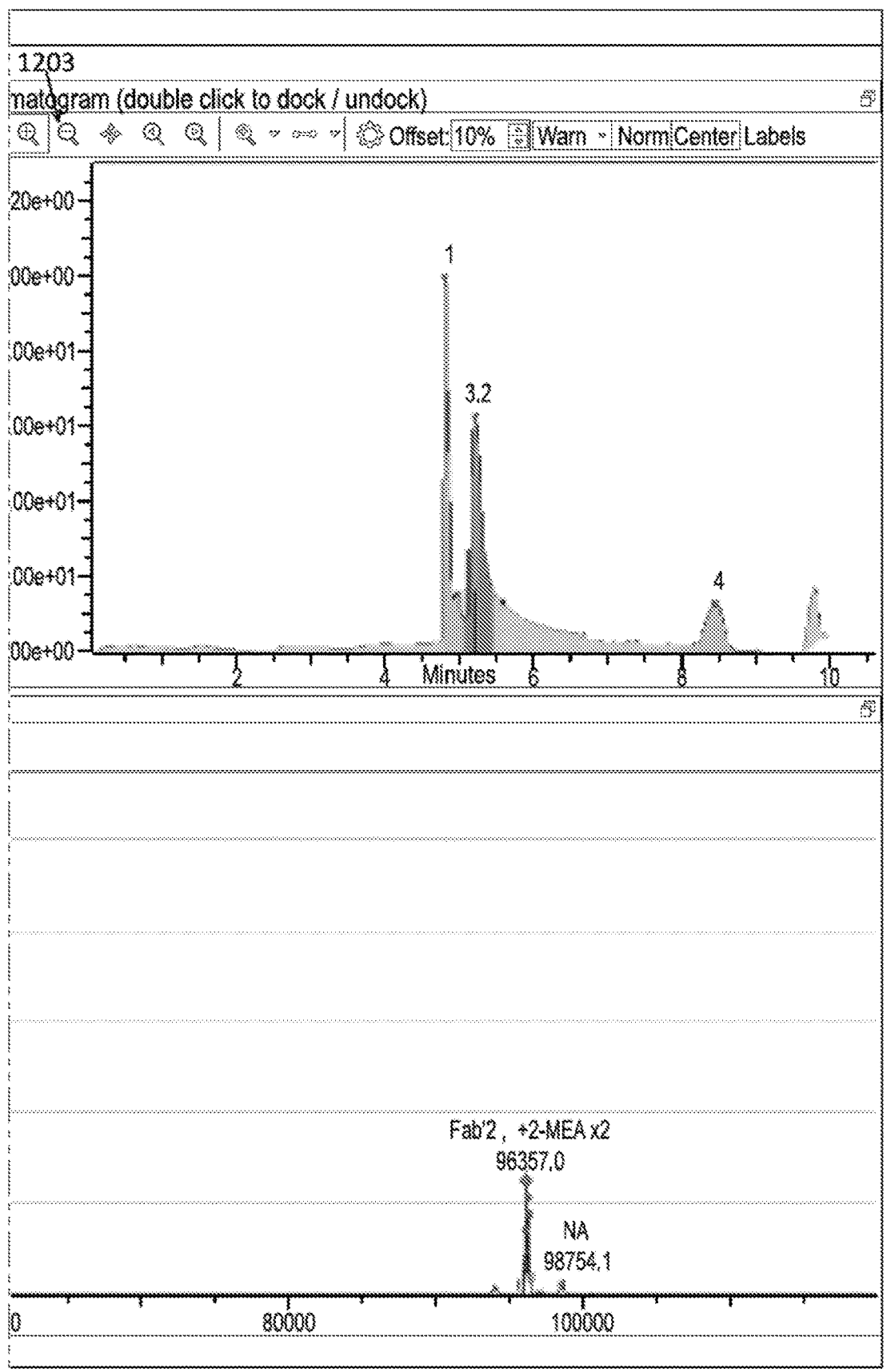

Any number of peaks/masses may be selected and shown with a unique marker (e.g., colored dot, etc.) across the different spectral displays (e.g., MS1, deconvolved mass spectrum, etc.). For example, FIGS. 12A-12C shows an example in which four selected masses, each indicated by a characteristic color "dot" are shown. A mass may be selected from the mass table, or a graph (e.g., any of the windows shown) and the selected mass indicated in all of the windows, in real time. In FIGS. 12A-12C, the dashboard includes a mass window 1201, a chromatogram window 1203, an MS1 window 1205 and a deconvolved mass spectrum window 1207.

Figure 13A:
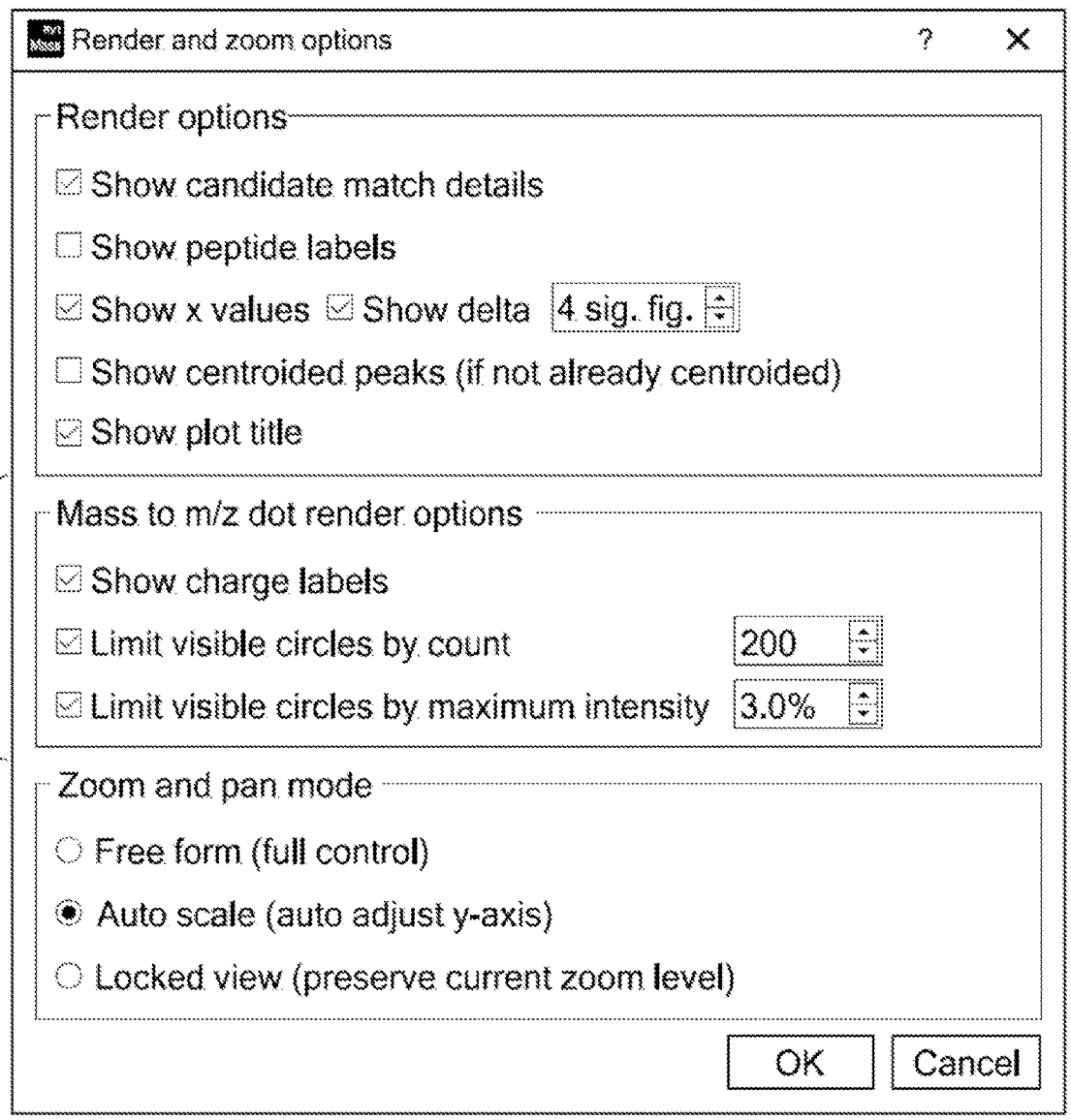
FIG. 13A illustrates a user control that may be used to control the display of the selected point(s) and corresponding values overlaid onto the data.
Figure 13B:
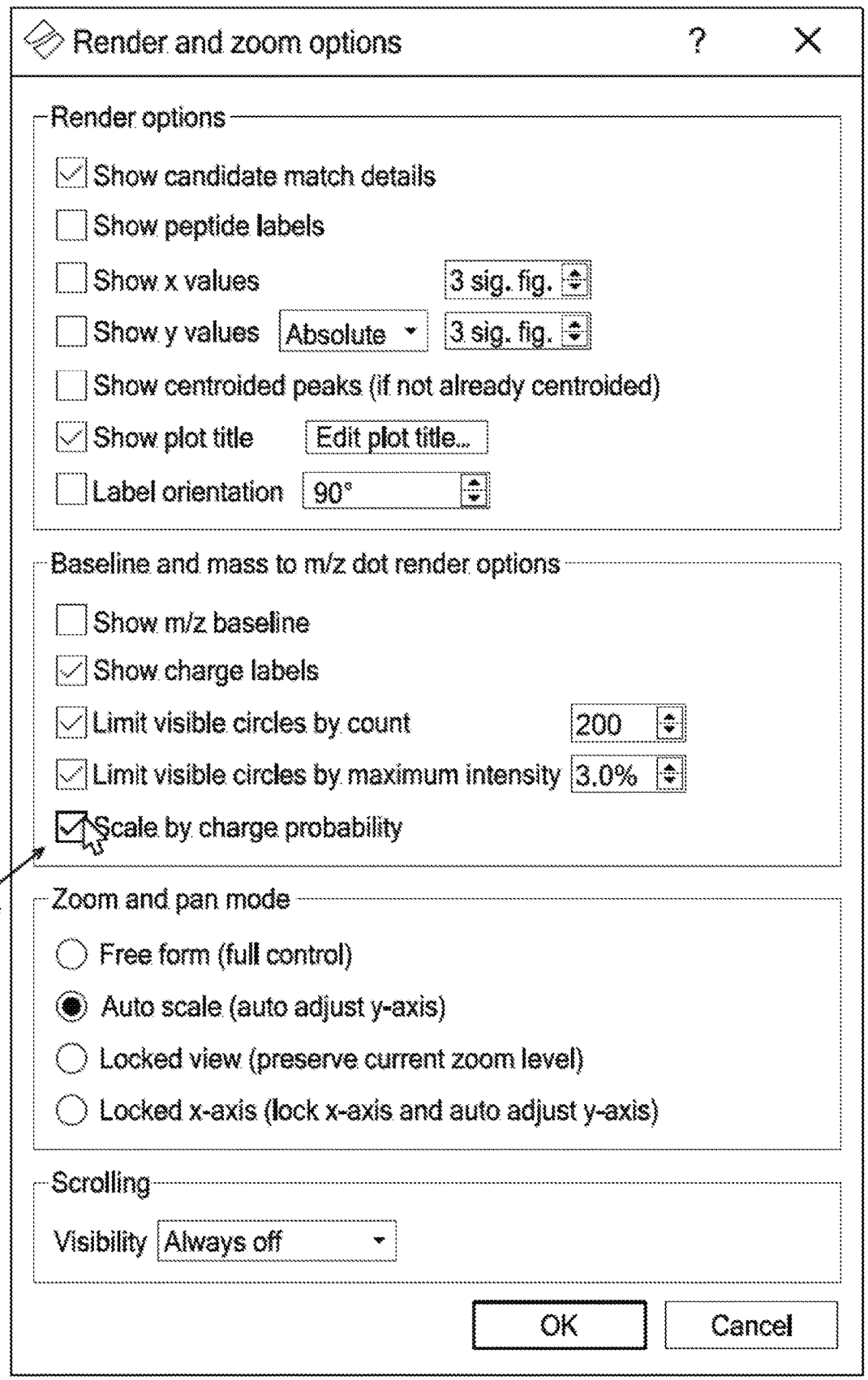
FIG. 13B illustrates another example of a user control similar to that shown in FIG. 13A.
Figure 14A:
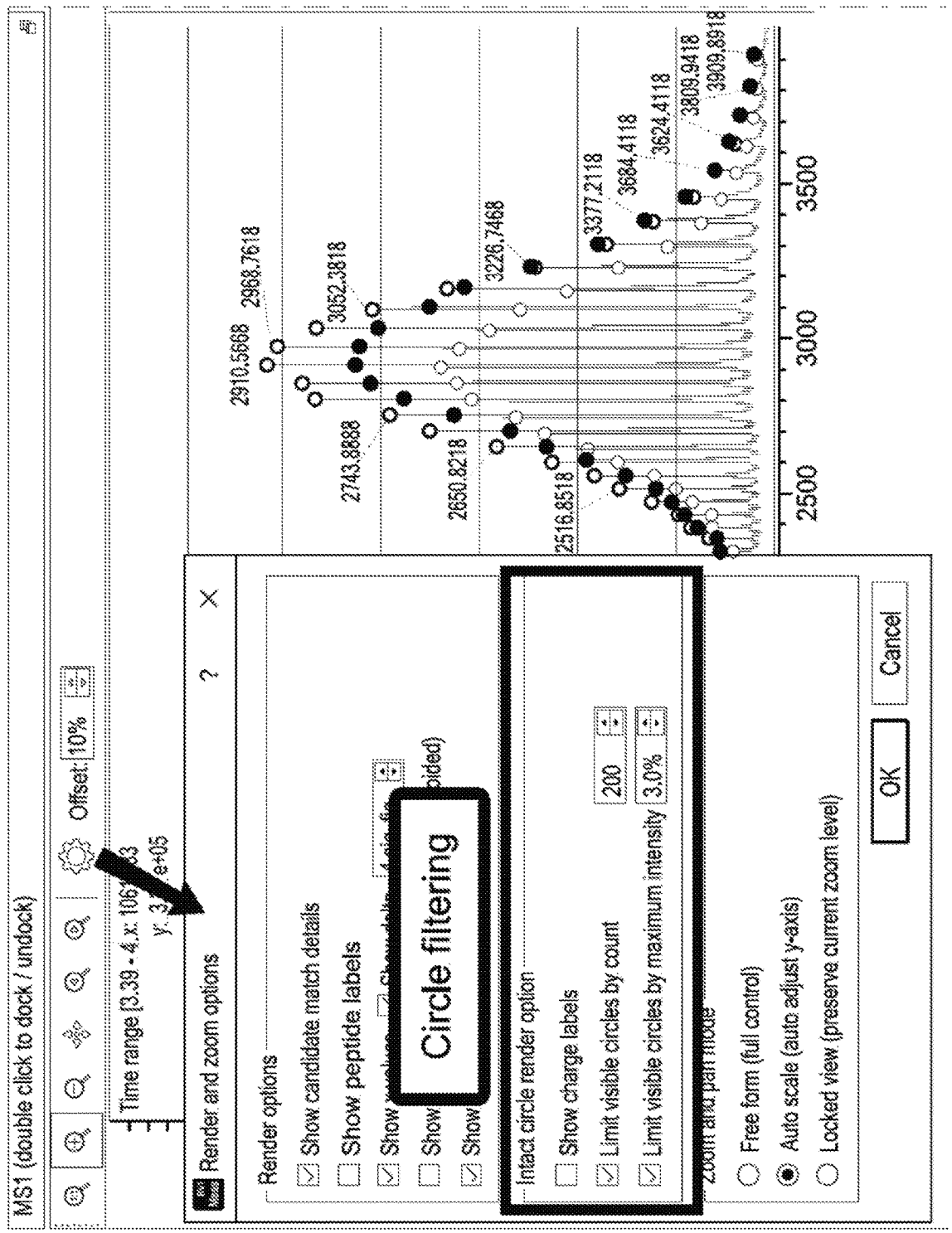
FIGS. 14A-14B illustrates the visual connection between deconvolved mass peaks with the corresponding charge states in the MS1 spectrum, as also illustrated in FIGS. 10A(1)-10A(3), FIGS. 11A-11C, and FIGS. 12A-12C, above, which may be achieved by correlating the mass peak and the charge states as described.
Figure 14B:
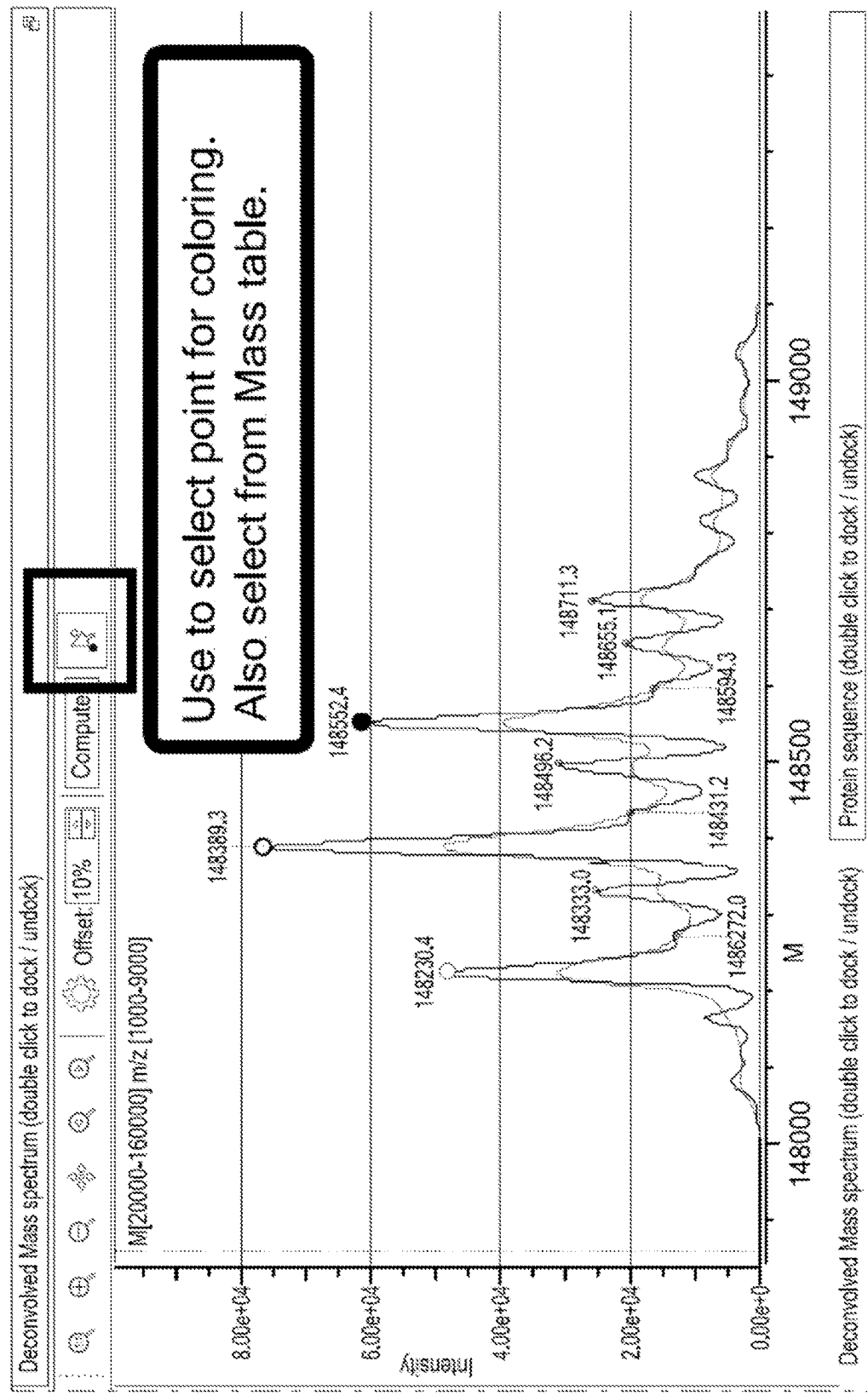

In general, the user may control the display of the marker that is overlaid onto the data in each screen. For example, FIG. 13A illustrates a user control that may be used to control the display of the selected point(s) and corresponding vales overlaid onto the data. The labels (e.g., "dots") may be labeled by text, color, or the like. In some variations, the total number of labeled points may be limited to a maximum and/or the transparency/visibility of the points may be selected and/or adjusted. In FIG. 13A the controls related to the markers 1301 are highlighted. FIG. 13B shows another example of a user control that may be used to control the display of the selected point(s) and corresponding vales overlaid onto the data. In both FIGS. 13A and 13B the control is a selectable control that will allow the system (or the user operating the system) to adjust the labeled marks based on a selectable control. For example, the selectable control may include toggling on/off the markers, charge labels, etc. The selectable control may limit the number of markers (e.g., "limit visible circles by count," where the count is selectable), may limit the intensity of the markers ("limit visible circles by maximum intensity," where the maximum intensity is selectable) and/or may scale the position of the marker (e.g., in the m/z plot) by charge probability 1305.

Figure 15:
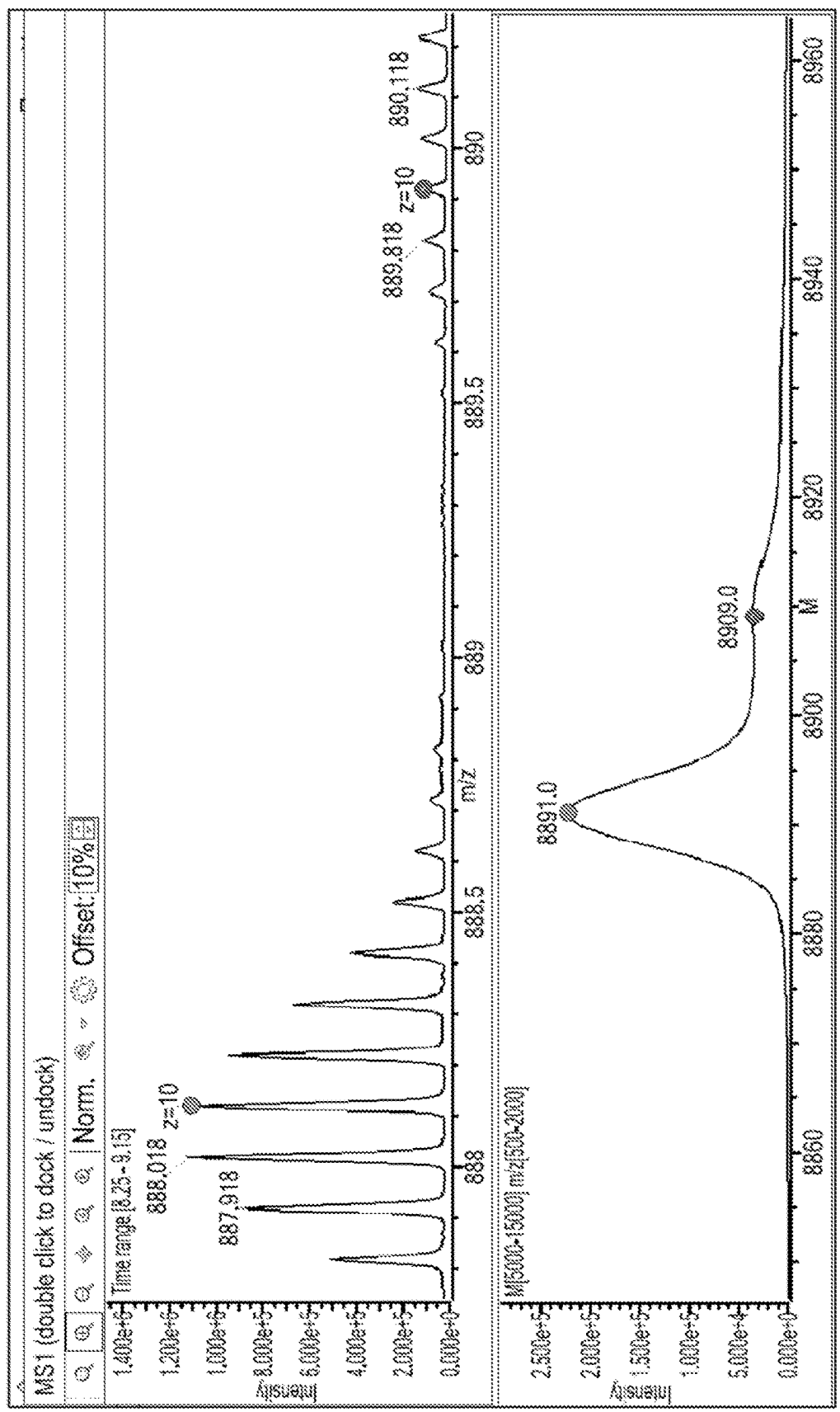
FIG. 15 illustrates one example of an adjustment of the (x-axis) position of the characteristic color "dot" x-coordinates to hit isotope peaks, rather than gaps between peaks, as described herein.

For example, FIG. 15 illustrates an example of an m/z plot portion of the display as described herein, in which the x-position of the maker (in this case, colored dots) has been adjusted so that the x-coordinate of the marker is positioned at the top of an isotope peak, rather than a gap between isotope peaks. This may be helpful when, for example, a user has smoothed the isotope peaks in a deconvoluted mass spectrum (as shown in the lower plot 1508 of FIG. 15). In this example, the value of 8891.0/10-1 (for proton)=888.1 would land to the left of the tip of the sharp peak in the upper, m/z plot 1510. The control may be set (e.g., by the user, by default, etc.) to adjust the x-coordinate position so that the position is shifted slightly to the peak, as shown in the m/z plot.

Figure 16A:
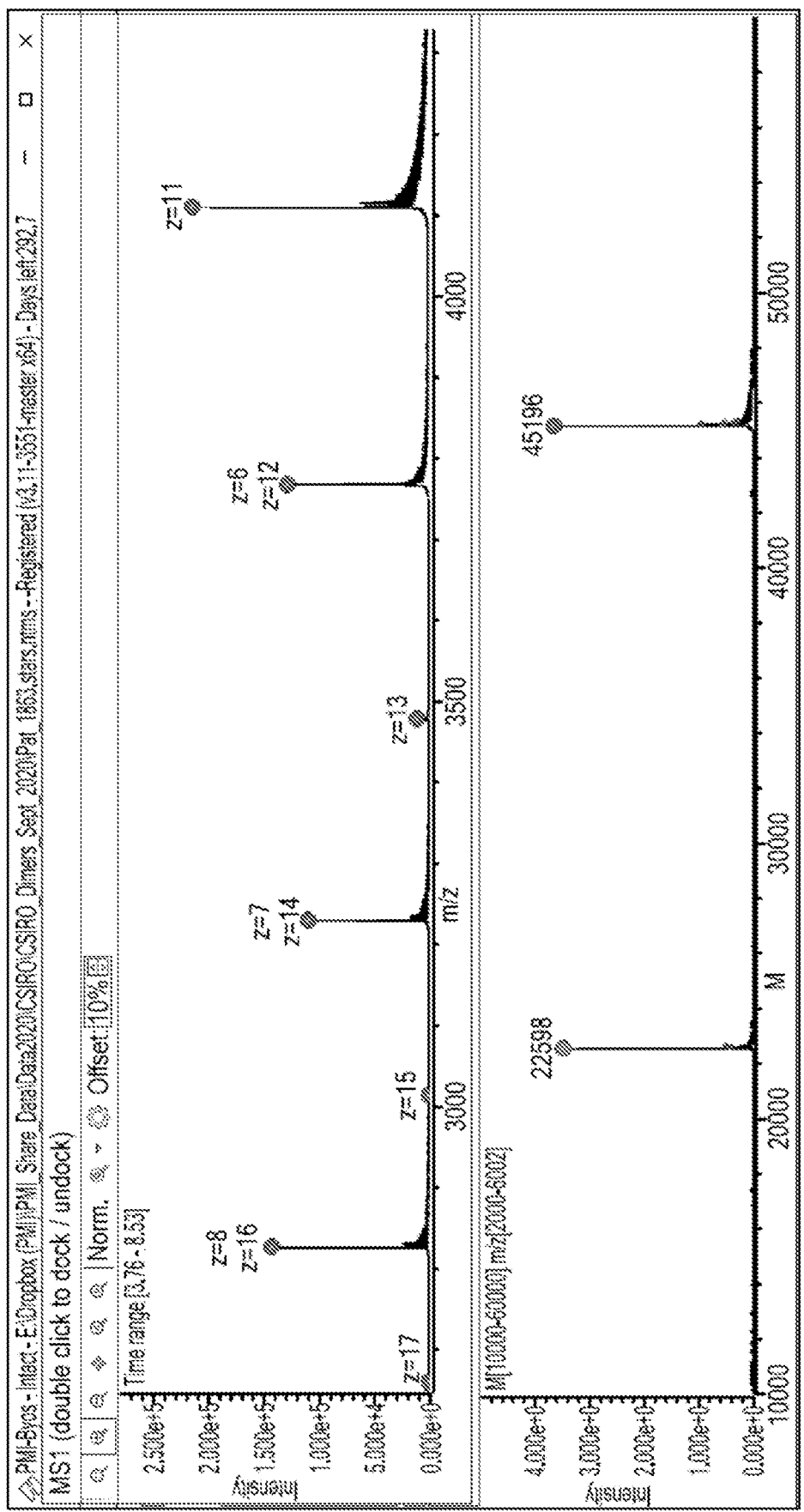
FIGS. 16A and 16B illustrate an example of adjustment of the (y-axis) position of a characteristic color "dot" y-coordinates to show another variable, e.g., fraction of peak with assigned charge, as described herein.
Figure 16B:
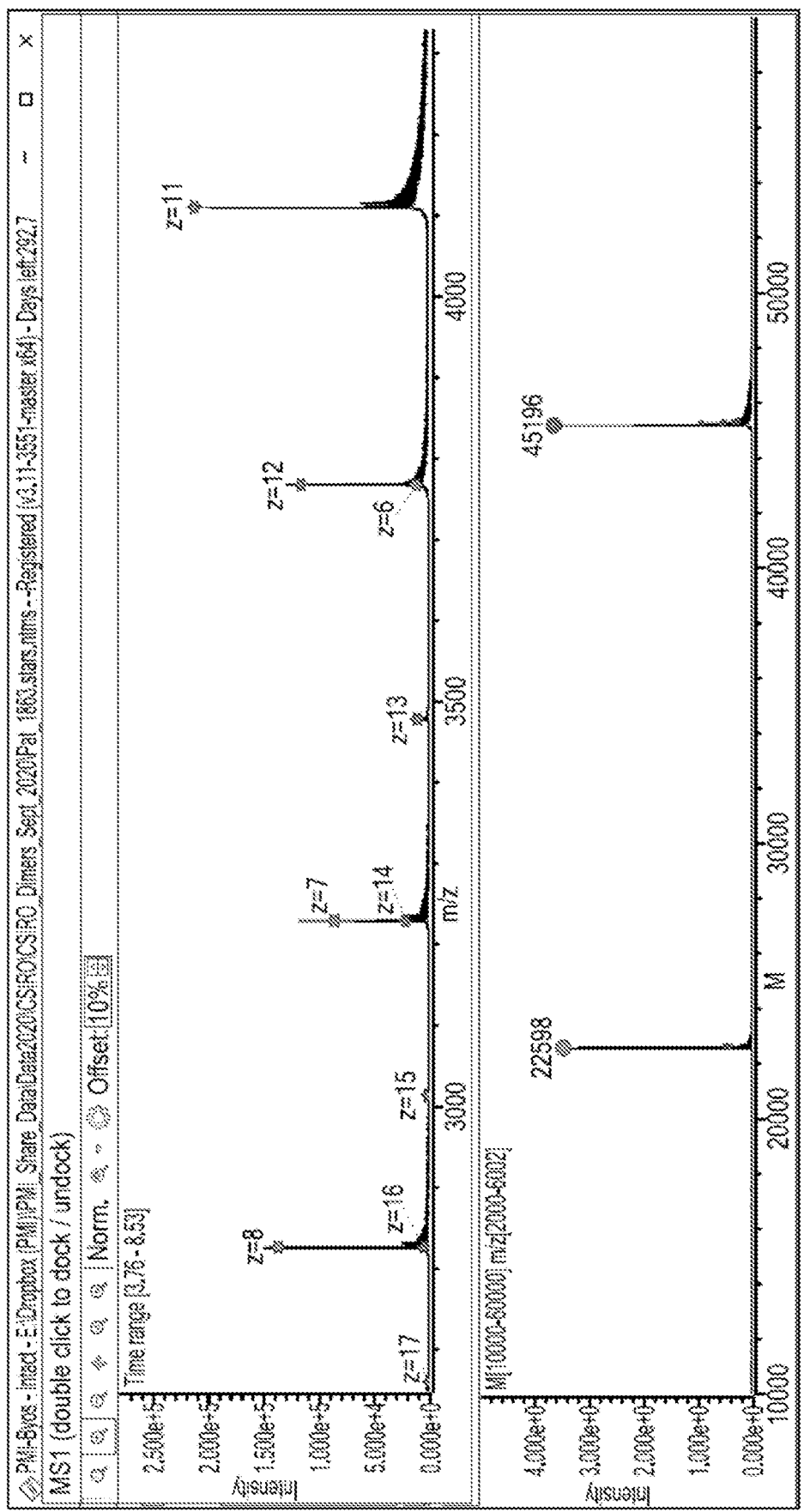

In some examples, particularly when there are multiple masses that would otherwise overlap, as shown in FIG. 16A, the y-value of the markers may be adjusted to prevent or reduce overlap. For example, in FIG. 16A, the y-coordinates of multiple markers have not been adjusted to allow non-overlapping display of multiple markers, and multiple markers are overlapping (so that only a single marker, in this example a colored dot, is shown, through the values are visible above the markers). FIG.16B shows an example in which the selectable color indicates that the markers in the m/z rendering ("Baseline and mass to m/z dot render options") should be adjusted to scale by charge probability. In FIG. 16B, the y-coordinate of the markers (colored dots) have their y-coordinates adjusted (scaled) to show another variable, in this case, the fraction of the m/z peak assigned to the m peak of the corresponding color. The selected masses which otherwise hit on exactly the same m/z peaks may be shown so that their position on the peak reflects the relative contribution of that charge state to the peak. In this example, the second marker does not indicate much charge 14 or 16 (or else it would also have a lot of charge 13 and 15) and is shown near the x-axis.

Thus, as described above, the y-coordinates of the markers (e.g., colored dots) may be adjusted to reflect charge probability at a m/z point. In any of these examples, the adjustment and/or labeling of the markers may reflect a mix of known charges at an m/z point. For example, the adjustment may reflect different, but similar cases: (a) an m/z point might be 60% charge 10 and 40% electronic noise with no actual charged molecules, or (b) an m/z point might be 60% charge 10 and 40% some other charge (e.g., charge 20 from a dimer of the charge −10 molecule).

As mentioned above, also described herein are m/z plots, mass spectrum plot, and other plots derived from the received mass spec data file. For example, FIGS. 6 shows an interactive visual representations derived from the received data file including an XIC plot (bottom left). The mass XIC shows a weighted average of the m/z peak heights over time. The fact that heavier masses have later apex elution times in the mass XIC plot is confirmatory evidence that the m spectrum is correct. In other cases, apex elution time might be more than confirmatory, and may help identify the molecule.

Thus, in some examples, the interactive display includes a mass XIC (also referred to as an extracted ion count), which shows a weighted average of the m/z peak heights over a certain elution time. FIGS. 17A(1)-17A(3) and 17E show another example dashboard showing multiple windows, including a mass listing 1701, a chromatogram 1703, an MS1 spectrum 1705, a deconvolved mass spectrum 1707, and a Mass XIC 1709. As shown in greater detail in FIG. 17C, the chromatogram 1703 may be divided into intervals (slices) that are delineated with vertical lines. In this example, the intervals each have a time of six seconds. In some examples the user may select an elution time interval range to analyze, which may include one or more of the intervals. In the example show, the user selected a twelve second range (two six second intervals). The Mass XIC 1709 shows the weighted average of the corresponding m/z peak heights over the elution time selected in the chromatogram 1703. As shown in greater detail in FIG. 17D, the Mass XIC 1709 shows four elution plots 1725, 1727, 1729, and 1731 indicating the elution time of four different masses (Mass ID 81, Mass ID 84, Mass ID 87, and Mass ID 90). The plots 1725, 1727, 1729, and 1731 are shown separately in rows so that the user can easily resolve the different elution peaks associated with each identified mass ID. Each plot 1725, 1727, 1729, and 1731 represents a height of the m/z point in each of the scans that went into the selected time range (e.g., 12 second). In addition, the peaks 1725, 1727, 1729, and 1731 may be displayed using different colors. In this example, the peak 1725 may be displayed in a first (e.g., an orange) color, peak 1727 is displayed in a second (e.g., blue) color, peak 1729 is displayed in a third (e.g., magenta) color, and peak 1731 is displayed in a fourth (e.g., yellow) color.

Figure 17B:
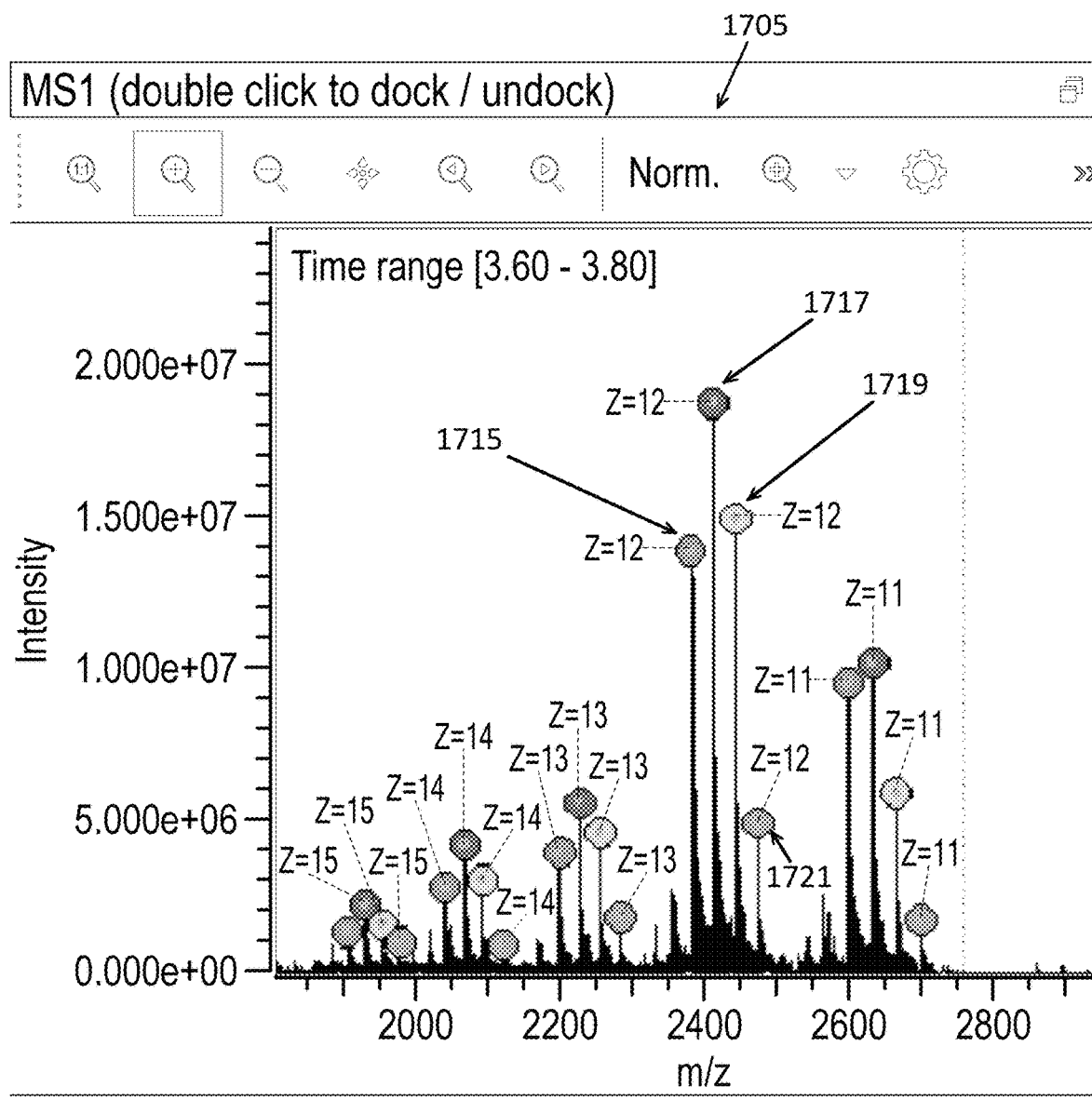
FIG. 17B illustrates an enlarged view of the labeled MS1 window of FIGS. 17A(1)-17A(3).
Figure 17C:
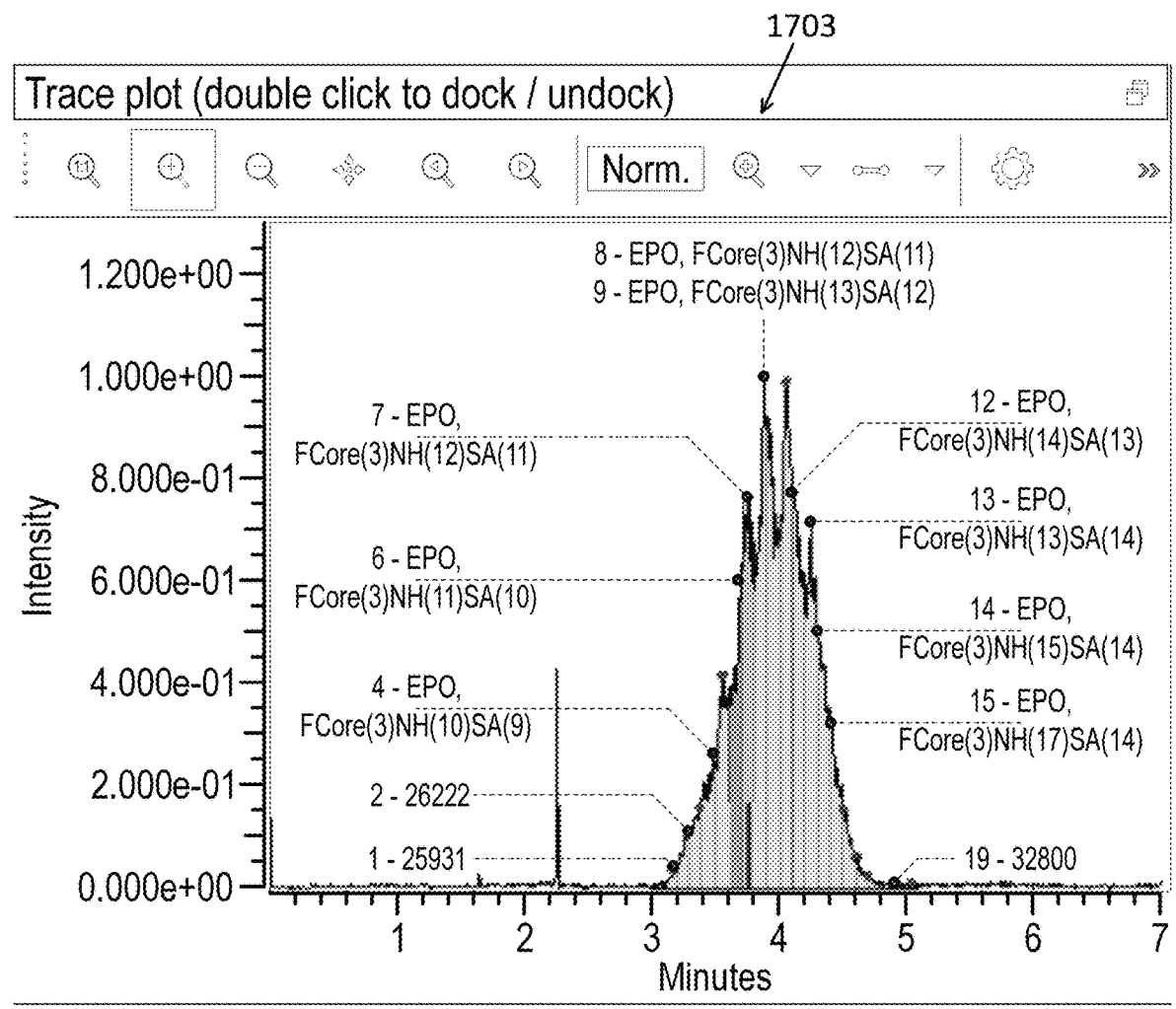
FIG. 17C illustrates an enlarged view of the chromatogram window of FIGS. 17A(1)-17A(3).
Figure 17D:
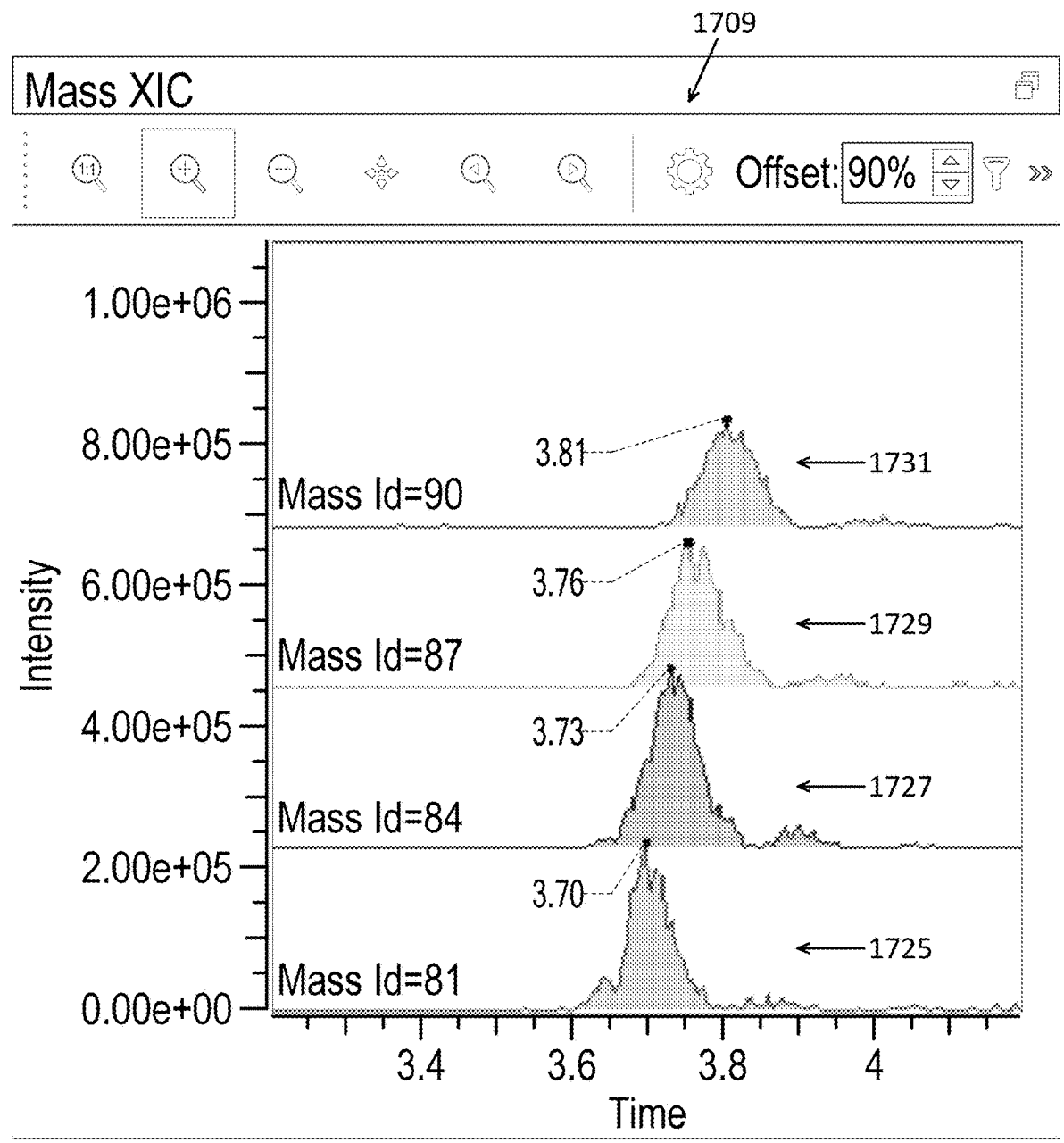
FIG. 17D illustrates an enlarged view of the mass XIC window of FIGS. 17A(1)-17A(3).

The mass listing 1701, the MS1 plot 1705, and the deconvolved mass spectrum 1707 may also be updated to reflect the species within the selected elution time range in the chromatogram 1703. For example, the mass listing 1701 shows the Mass ID 90 as highlighted, which is included in the selected elution time range of the chromatogram 1703. The MS1 spectrum 1705 and the deconvolved mass spectrum 1707 are also be updated to show the peaks (and colored dots) of associated species eluted during the selected elution time interval. For example, as shown in FIG. 17B, the MS1 spectrum 1705 includes subsets of peaks that include: a first series of peaks (represented by orange dots 1715) corresponding to Mass ID 81, a second series of peaks (represented by blue dots 1717) corresponding to Mass ID 84, a third series of peaks (represented by magenta dots 1719) corresponding to Mass ID 87, and a fourth series of peaks (represented by yellow dots 1721) corresponding Mass ID 90. The colors of the dots 1715, 1717, 1719, and 1721 match the colors of the elution peaks in the Mass XIC 1709 so that a user can track the various masses between the display windows. Note that in this example view of the MS1 spectrum 1705, the charge (z) labels of the peaks are shown but the mass labels are hidden.

Figure 17E:
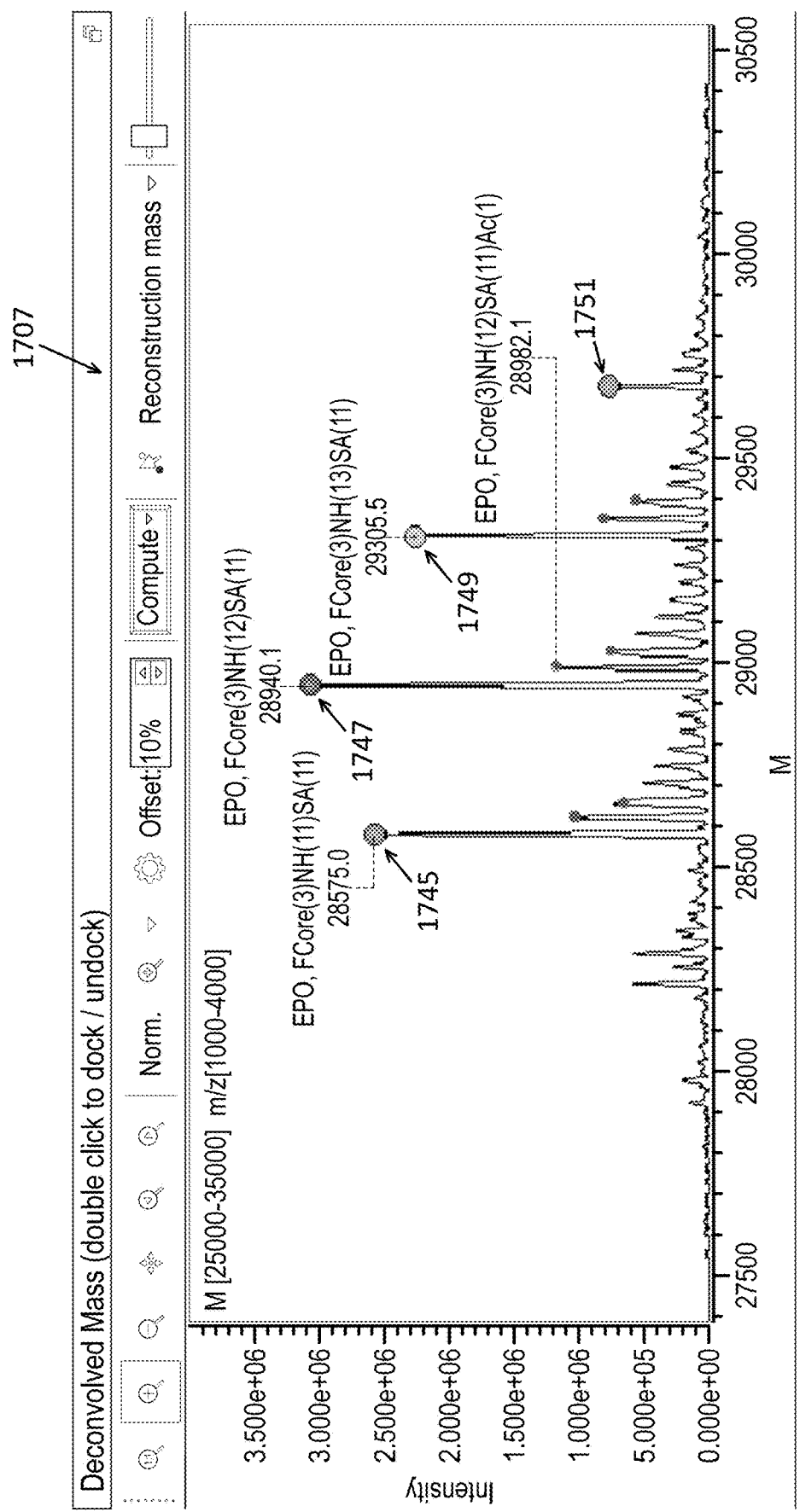
FIG. 17E illustrates an enlarged view of the deconvoluted mass spectrum window of FIGS. 17A(1)-17A(3).

As shown in FIG. 17E, the mass deconvolved mass spectrum 1707 is also updated to reflect the masses associated with the selected elution time interval ranges. In this example, the mass deconvolved mass spectrum 1707 includes a first peak (represented by an orange dot 1745) corresponding to Mass ID 81, a second peak (represented by a blue dot 1747) corresponding to Mass ID 84, a third peak (represented by magenta dots 1749) corresponding to Mass ID 87, and a fourth peak (represented by a yellow dot 1751)

corresponding Mass ID 90. As with the MS1 spectrum 1705, the colors of the dots 1745, 1747, 1749, and 1751 may match the colors (or markings) of the elution peaks in the Mass XIC 1709.

By interactively displaying this information in the windows as shown, a user may more easily interpret the spectroscopic data, distinguish actual signal from the noise, and view and compare different species based on m/z, mass, and elution time. The Mass XIC 1709 plot may be used by the user, for example, to confirm that the peaks in the MS1 spectrum 1705 are correspond to molecular species. For example, since heavier masses have later apex elution times, displaying weighted averages of the m/z peak heights may allow the user to verify that the peaks in the MS1 spectrum 1705 correspond with those in the Mass XIC 1709. In other cases, apex elution time in the Mass XIC 1709 plot may be used to identify one or more molecules in the sample.

Although the method illustrated above in reference to FIGS. 17A(1)-17A(3) and 17E refers to selecting a time range from the chromatogram 1703, features in any of the multiple windows (mass listing 1701, chromatogram 1703, MS1 plot 1705, deconvolved mass spectrum 1707, and Mass XIC 1709) may be selected and cause information in the remaining windows to update accordingly. For example, one or more dots and/or peaks may be selected in the MS1 spectrum 1705 or the deconvolved mass spectrum 1707 may be selected. Corresponding mass(es) may then be highlighted in the mass listing 1701. As discussed herein, any of the windows may be manually or automatically rescaled, and this rescaling propagated across the other windows/spectral information.

As mentioned, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A non-transitory machine-readable medium that stores instructions, which, when performed by a machine, cause the machine to perform operations comprising:
   receiving a data file comprising mass spectrometry (MS) data for a sample comprising a molecule;
   simultaneously displaying a plurality of interactive visual representations derived from the received data file, the plurality of interactive visual representations comprising: a first visual representation comprising estimated or calculated masses from the received data file, a second visual representation comprising a distribution of mass/charge (m/z) values estimated or calculated from the received data file, and a third visual representation comprising a deconvolved mass spectrum estimated or calculated from the received data file;
   receiving a plurality of user-selected regions from one or more of: the first visual representation, the second visual representation or the third visual representation;
   determining, from the plurality of user-selected regions, a plurality of user-selected mass values;
   displaying, simultaneously, a separate labeled mark corresponding to each of the user-selected mass values on one or both of the first and third visual representations, and simultaneously displaying the labeled mark corresponding the each of the user-selected mass values on each of a plurality of sites on the distribution of m/z values, wherein the labeled marks each uniquely correspond to the corresponding user-selected mass value; and
   adjusting the labeled marks based on a selectable control.

2. The non-transitory machine-readable medium of claim 1, wherein adjusting comprises adjusting an x position on the distribution of m/z values.

3. The non-transitory machine-readable medium of claim 1, wherein adjusting comprises adjusting a y position on the distribution of m/z values.

4. The non-transitory machine-readable medium of claim 1, wherein adjusting comprises adjusting a transparency on the distribution of m/z values.

5. The non-transitory machine-readable medium of claim 1, wherein each labeled mark comprises a colored dot.

6. The non-transitory machine-readable medium of claim 1, wherein each labeled mark comprises an annotated colored dot.

7. The non-transitory machine-readable medium of claim 1, wherein receiving the plurality of user-selected mass values comprises identifying mass values from a user-selected region of the second visual representation and/or the third visual representation.

8. The non-transitory machine-readable medium of claim 7, wherein identifying the mass values from the user-selected region comprises identifying a peak mass value from the user-selected region.

9. The non-transitory machine-readable medium of claim 1, wherein adjusting comprises adjusting a y position on the distribution of m/z values to scale by charge probability.

10. The non-transitory machine-readable medium of claim 1, wherein displaying each labeled mark corresponding to the selected mass values on the plurality of sites on the distribution of m/z values comprises identifying a maximum amplitude within a predetermined range in the distribution of m/z values and displaying the labeled mark on the maximum amplitude for each site of the plurality of sites.

11. A method for interactively displaying mass spectrometry data, the method comprising:
    receiving a data file comprising mass spectrometry (MS) data for a sample comprising a molecule;
    simultaneously displaying a plurality of interactive visual representations derived from the received data file, the plurality of interactive visual representations comprising: a first visual representation comprising estimated or calculated masses from the received data file, a second visual representation comprising a distribution of mass/charge (m/z) values estimated or calculated from the received data file, and a third visual representation comprising a deconvolved mass spectrum estimated or calculated from the received data file;

receiving a plurality of user-selected regions from one or more of: the first visual representation, the second visual representation or the third visual representation;

determining, from the plurality of user-selected regions, a plurality of user-selected mass values;

displaying, simultaneously, a separate labeled mark corresponding to each of the user-selected mass values on one or both of the first and third visual representations, and simultaneously displaying the labeled mark corresponding the each of the user-selected mass values on each of a plurality of sites on the distribution of m/z values, wherein the labeled marks each uniquely correspond to the corresponding user-selected mass value; and adjusting the labeled marks based on a selectable control.

12. The method of claim 11, wherein adjusting comprises adjusting an x position on the distribution of m/z values.

13. The method of claim 11, wherein adjusting comprises adjusting a y position on the distribution of m/z values.

14. The method of claim 11, wherein adjusting comprises adjusting a transparency on the distribution of m/z values.

15. The method of claim 11, wherein each labeled mark comprises a colored dot.

16. The method of claim 11, wherein receiving the plurality of user-selected mass values comprises identifying mass values from a user-selected region of the second visual representation and/or the third visual representation.

17. The method of claim 16, wherein identifying the mass values from the user-selected region comprises identifying a peak mass value from the user-selected region.

18. The method of claim 11, wherein adjusting comprises adjusting a y position on the distribution of m/z values to scale by charge probability.

19. The method of claim 11, wherein displaying each labeled mark corresponding to the selected mass values on the plurality of sites on the distribution of m/z values comprises identifying a maximum amplitude within a predetermined range in the distribution of m/z values and displaying each labeled mark on the maximum amplitude for each site of the plurality of sites.

20. A method for interactively displaying mass spectrometry data, the method comprising:

receiving a data file comprising mass spectrometry (MS) data for a sample comprising a molecule;

simultaneously displaying a plurality of interactive visual representations derived from the received data file, the plurality of interactive visual representations comprising: a first visual representation comprising estimated or calculated masses from the received data file, a second visual representation comprising a distribution of mass/charge (m/z) values estimated or calculated from the received data file, and a third visual representation comprising a deconvolved mass spectrum estimated or calculated from the received data file;

receiving a set of user-selected mass values from one or more of: the first visual representation, the second visual representation or the third visual representation, by a user selecting one or more regions of the interactive visual representations and automatically identifying a plurality of mass values from within a predetermined range;

displaying a labeled mark corresponding to each mass value of the set of user-selected of mass values on one or both of the first and third visual representations, and simultaneously displaying a set of labeled marks corresponding to each of the mass values at a plurality of sites on the distribution of mass/charge (m/z) values, wherein displaying the set of labeled marks corresponding to each of the selected mass values on the plurality of sites on the distribution of m/z values comprises identifying a maximum amplitude within the predetermined range in the distribution of m/z values and displaying the labeled mark on the maximum amplitude for each site of the plurality of sites; and adjusting one or more of an x position on the distribution of m/z values and a y position on the distribution of m/z values of the labeled mark based on a selectable control.

* * * * *